(12) United States Patent
Asokan et al.

(10) Patent No.: US 9,409,953 B2
(45) Date of Patent: Aug. 9, 2016

(54) VIRAL VECTORS WITH MODIFIED TRANSDUCTION PROFILES AND METHODS OF MAKING AND USING THE SAME

(75) Inventors: Aravind Asokan, Chapel Hill, NC (US); Nagesh Pulicherla, Hyderabad (IN)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/984,840

(22) PCT Filed: Feb. 10, 2012

(86) PCT No.: PCT/US2012/024702
§ 371 (c)(1),
(2), (4) Date: Oct. 28, 2013

(87) PCT Pub. No.: WO2012/109570
PCT Pub. Date: Aug. 16, 2012

(65) Prior Publication Data
US 2014/0056854 A1 Feb. 27, 2014

Related U.S. Application Data

(60) Provisional application No. 61/441,411, filed on Feb. 10, 2011.

(51) Int. Cl.
| | | |
|---|---|---|
| *C07K 14/005* | (2006.01) | |
| *C12N 15/86* | (2006.01) | |
| *C12N 7/00* | (2006.01) | |
| *C07K 14/015* | (2006.01) | |
| *C07K 14/01* | (2006.01) | |
| *A61K 39/23* | (2006.01) | |
| *C12N 15/35* | (2006.01) | |

(52) U.S. Cl.
CPC ............ *C07K 14/005* (2013.01); *C12N 7/00* (2013.01); *C12N 15/86* (2013.01); *C12N 2750/14121* (2013.01); *C12N 2750/14122* (2013.01); *C12N 2750/14132* (2013.01); *C12N 2750/14133* (2013.01); *C12N 2750/14143* (2013.01); *C12N 2750/14152* (2013.01)

(58) Field of Classification Search
CPC ........ C07K 14/005; C12N 15/86; C12N 7/00; C12N 2750/14145; C12N 2750/14143; C12N 2750/14122; C12N 2750/14121; C12N 2750/14132; C12N 2750/14133; C12N 2750/14152; A61K 2039/505; A61K 38/1709; A61K 2039/552; A61K 35/76; A61K 38/162
See application file for complete search history.

(56) References Cited

U.S. PATENT DOCUMENTS

| | | | |
|---|---|---|---|
| 2005/0287122 A1 | 12/2005 | Bartlett et al. | |
| 2007/0036760 A1* | 2/2007 | Wilson et al. | 424/93.2 |
| 2007/0196338 A1* | 8/2007 | Samulski et al. | 424/93.2 |
| 2009/0215879 A1* | 8/2009 | Diprimio et al. | 514/44 R |
| 2011/0104120 A1* | 5/2011 | Xiao et al. | 424/93.2 |
| 2012/0009268 A1* | 1/2012 | Asokan et al. | 424/499 |

FOREIGN PATENT DOCUMENTS

| | | |
|---|---|---|
| WO | WO 03/052052 A2 | 6/2003 |
| WO | WO 2004/111248 A2 | 12/2004 |
| WO | WO 2005/005610 A2 | 1/2005 |
| WO | WO 2005/033321 A2 | 4/2005 |
| WO | WO 2009/137006 A2 | 11/2009 |
| WO | WO 2010093784 A2 * | 8/2010 |
| WO | WO 2010/138263 A2 | 12/2010 |
| WO | WO 2012/112832 A1 | 8/2012 |

OTHER PUBLICATIONS

Li W, Zhang L, Johnson JS, Zhijian W, Grieger JC, Ping-Jie X, Drouin LM, Agbandje-McKenna M, Pickles RJ, Samulski RJ. Generation of novel AAV variants by directed evolution for improved CFTR delivery to human ciliated airway epithelium. Mol Ther. Dec. 2009;17(12):2067-77. doi: 10.1038/mt.2009.155. Epub Jul. 14, 2009.*
Bowie JU, et. al. Science. Mar. 16, 1990;247(4948):1306-10.*
Vandenberghe LH, Breous E, Nam HJ, Gao G, Xiao R, Shandu A, Johnston J, Debyser Z, Agbandje-McKenna M, Wilson JM. capsid protein VP1, partial (endogenous virus) [Adeno-associated virus]. GenBank Acc. No. ACB55317.1. Dep. Jul. 31, 2008.*
Gao G, Vandenberghe LH, Alvira MR, Lu Y, Calcedo R, Zhou X, Wilson JM. capsid protein VP1 [Adeno-associated virus]. GenBank Acc. No. AAS99239.1. Dep. Jun. 24, 2004.*
Gao G, Vandenberghe LH, Alvira MR, Lu Y, Calcedo R, Zhou X, Wilson JM. Clades of Adeno-associated viruses are widely disseminated in human tissues. J Virol. Jun. 2004;78(12):6381-8.*
Zinn E, Pacouret S, Khaychuk V, Turunen HT, Carvalho LS, Andres-Mateos E, Shah S, Shelke R, Maurer AC, Plovie E, Xiao R, Vandenberghe LH. In Silico Reconstruction of the Viral Evolutionary Lineage Yields a Potent Gene Therapy Vector. Cell Rep. Aug. 11, 2015;12(6):1056-68. Epub Jul. 30, 2015.*
Akache et al. "The 37/67-Kilodalton Laminin Receptor is a Receptor for Adeno-Associated Virus Serotypes 8, 2, 3, and 9" *Journal of Virology* 80(19):9831-9836 (2006).
Arnold et al. "The Swiss-Model workspace: a web-based environment for protein structure homology modelling" *Bioinformatics* 22(2):195-201 (2006).
Asokan et al. "Adeno-Associated Virus Type 2 Contains an Integrin α5β1 Binding Domain Essential for Viral Cell Entry" *Journal of Virology* 80(18):8961-8969 (2006).

(Continued)

*Primary Examiner* — Rachel B Gill
(74) *Attorney, Agent, or Firm* — Myers Bigel & Sibley, P.A.

(57) ABSTRACT

The present invention provides AAV capsid proteins, virus capsids comprising said capsid proteins and virus vectors comprising said capsid proteins, wherein the AAV capsid proteins have one or more mutations, wherein the mutation(s) result in a phenotype of decreased liver transduction and/or reduced glycan binding affinity as compared to a control. The invention also provides methods of administering the virus vectors and virus capsids of the invention to a cell or to a subject.

20 Claims, 16 Drawing Sheets

(56) References Cited

OTHER PUBLICATIONS

Asokan et al. "Reengineering a receptor footprint of adeno-associated virus enables selective and systemic gene transfer to muscle" *Nature Biology* 28(1):79-83 (2010).
Bish et al. "Adeno-Associated Virus (AAV) Serotype 9 Provides Global Cardiac Gene Transfer Superior to AAV1, AAV6, AAV7, and AAV8 in the Mouse and Rat" *Human Gene Therapy* 19:1359-1368 (2008).
Boecker et al. "Cardiac-Specific Gene Expression Facilitated by an Enhanced Myosin Light Chain Promoter" *Molecular Imaging* 3(2):69-75 (2004).
Brantly et al. "Sustained transgene expression despite T lymphocyte responses in a clinical trial of rAAV1-AAT gene therapy" *Proceedings of the National Academy of Sciences* 106(38):16363-16368 (2009).
Brown et al. "Exploiting and antagonizing microRNA regulation for therapeutic and experimental applications" *Nature Reviews: Genetics* 10:578-585 (2009).
Carrillo-Tripp et al. "VIPERdb$^2$: an enhanced and web API enabled relational database for structural virology" *Nucleic Acids Research* 37:D436-D442 (2009).
Excoffon et al. "Directed evolution of adeno-associated virus to an infectious respiratory virus" *Proceedings of the National Academy of Sciences* 106(10):3865-3870 (2009).
Foust et al. "Intravascular AAV9 preferentially targets neonatal neurons and adult astrocytes" *Nature Biology* 27(1):59-65 (2009).
Gao et al. "Clades of Adeno-Associated Viruses Are Widely Disseminated in Human Tissues" *Journal of Virology* 78(12):6381-6388 (2004).
Geisler et al. "microRNA122-regulated transgene expression increases specificity of cardiac gene transfer upon intravenous delivery of AAV9 vectors" *Gene Therapy* 18:199-209 (2011).
Govindasamy et al. "Structurally Mapping the Diverse Phenotype of Adeno-Associated Virus Serotype 4" *Journal of Virology* 80(23):11556-11570 (2006).
Grieger et al. "Production and characterization of adeno-associated viral vectors" *Nature Protocols* 1(3):1412-1428 (2006).
Halbert et al. "Expression of Human α1-Antitrypsin in Mice and Dogs Following AAV6 Vector-mediated Gene Transfer to the Lungs" *Molecular Therapy* 18(6):1165-1172 (2010).
Hasbrouck et al. "AAV-mediated gene transfer for the treatment of hemophilia B: problems and prospects" *Gene Therapy* 15:870-875 (2008).
Herzog et al. "Two Decades of Clinical Gene Therapy—Success Is Finally Mounting" *Discovery Medicine* 9(45):105-111 (2010).
Inagaki et al. "Robust Systemic Transduction with AAV9 Vectors in Mice: Efficient Global Cardiac Gene Transfer Superior to That of AAV8" *Molecular Therapy* 14(1):45-53 (2006).
Kalyuzhniy et al. "Adenovirus serotype 5 hexon is critical for virus infection of hepatocytes in vivo" *Proceedings of the National Academy of Sciences* 105(14):5483-5488 (2008).
Kern et al. "Identification of a Heparin-Binding Motif on Adeno-Associated Virus Type 2 Capsids" *Journal of Virology* 77(20):11072-11081 (2003).
Koerber et al. "Molecular Evolution of Adeno-associated Virus for Enhanced Glial Gene Delivery" *Molecular Therapy* 17(12):2088-2095 (2009).
Kornegay et al. "Widespread Muscle Expression of an AAV9 Human Mini-dystrophin Vector After Intravenous Injection in Neonatal Dystrophin-deficient Dogs" *Molecular Therapy* 18(8):1501-1508 (2010).
Lerch et al. "The structure of adeno-associated virus serotype 3B (AAV-3B): Insights into receptor binding and immune evasion" *Virology* 403(1):26-36 (2010).
Levy et al. "Heparin binding induces conformational changes in Adeno-associated virus serotype 2" *Journal of Structural Biology* 165(3):146-156 (2009).

Lipskaia et al. "Sarcoplasmic reticulum $Ca^{2+}$ ATPhase as a therapeutic target for heart failure" *Expert Opinion on Biological Therapy* 10(1):29-41 (2010).
Lochrie et al. "Mutations on the External Surfaces of Adeno-Associated Virus Type 2 Capsids That Affect Transduction and Neutralization" *Journal of Virology* 80(2):821-834 (2006).
Michelfelder et al. "Adeno-Associated Viral Vectors and Their Redirection to Cell-Type Specific Receptors" *Advances in Genetics* 67:29-60 (2009).
Michelfelder et al. "Successful Expansion but Not Complete Restriction of Tropism of Adeno-Associated Virus by In Vivo Biopanning of Random Virus Display Peptide Libraries" *PLoS One* 4(4):e5122 (2009).
Mitchell et al. "AAV's Anatomy: Roadmap for Optimizing Vectors for Translational Success" *Current Gene Therapy* 10(5):319-340 (2010).
Molenaar et al. "Uptake and Processing of Modified Bacteriophage M13 in Mice: Implications for Phage Display" *Virology* 293:182-191 (2002).
Nam et al. "Identification of the Sialic Acid Structures Recognized by Minute Virus of Mice and the Role of Binding Affinity in Virulence Adaptation" *The Journal of Biological Chemistry* 281(35):25670-25677 (2006).
Nam et al. "Structure of Adeno-Associated Virus Serotype 8, a Gene Therapy Vector" *Journal of Virology* 81(22):12260-12271 (2007).
Opie et al. "Identification of Amino Acid Residues in the Capsid Proteins of Adeno-Associated Virus Type 2 That Contribute to Heparan Sulfate Proteoglycan Binding" *Journal of Virology* 77(12):6995-7006 (2003).
Pacak et al. "Recombinant Adeno-Associated Virus Serotype 9 Leads to Preferential Cardiac Transduction In Vivo" *Circulation Research* 99:e3-e9 (2006).
Prasuhn et al. "Plasma Clearance of Bacteriophage Qβ Particles as a Function of Surface Charge" *Journal of the American Chemical Society* 130(4):1328-1334 (2008).
Qiao et al. "Liver-specific microRNA-122 target sequences incorporated in AAV vectors efficiently inhibits transgene expression in the liver" *Gene Therapy* 18(4):403-410 (2011).
Rubio et al. "Virulent Variants Emerging in Mice Infected with the Apathogenic Prototype Strain of the Parvovirus Minute Virus of Mice Exhibit a Capsid with Low Avidity for a Primary Receptor" *Journal of Virology* 79(17):11280-11290 (2005).
Salva et al. "Design of Tissue-specific Regulatory Cassettes for High-level rAAV-mediated Expression in Skeletal and Cardiac Muscle" *Molecular Therapy* 15(2):320-329 (2007).
Shen et al. "Characterization of the Relationship of AAV Capsid Domain Swapping to Liver Transduction Efficiency" *Molecular Therapy* 15(11):1955-1962 (2007).
Shen et al. "Glycan Binding Avidity Determines the Systematic Fate of Adeno-Associated Virus Type 9" *Journal of Virology* 86(19):10408-10417 (2012).
Shen et al. "Engraftment of a Galactose Receptor Footprint onto Adeno-associated Viral Capsids Improves Transduction Efficiency" *The Journal of Biological Chemistry* 288(40):28814-28823 (2013).
Shen et al. "Multiple Roles for Sialylated Glycans in Determining the Cardiopulmonary Tropism of Adeno-Associated Virus 4" *Journal of Virology* 87(24):13206-13213 (2013).
Wang et al. "Construction and analysis of compact muscle-specific promoters for AAV vectors" *Gene Therapy* 15:1489-1499 (2008).
Wu et al. "Single Amino Acid Changes Can Influence Titer, Heparin Binding, and Tissue Tropism in Different Adeno-Associated Virus Serotypes" *Journal of Virology* 80(22):11393-11397 (2006).
Xiao et al. "Interpretation of Electron Density with Stereographic Roadmap Projections" *Journal of Structural Biology* 158(2):182-187 (2007).
Xie et al. "The atomic structure of adeno-associated virus (AAV-2), a vector for human gene therapy" *Proceedings of the National Academy of Sciences* 99(16):10405-10410 (2002).
Yang et al. "A myocardium tropic adeno-associated virus (AAV) evolved by DNA shuffling and in vivo selection" *Proceedings of the National Academy of Sciences* 106(10):3946-3951 (2009).

(56) References Cited

OTHER PUBLICATIONS

Ying et al. "Heart-targeted adeno-associated viral vectors selected by in vivo biopanning of a random viral display peptide library" *Gene Therapy* 17:980-990 (2010).

Zhong et al. "Next generation of adeno-associated virus 2 vectors: Point mutations in tyrosines lead to high-efficiency transduction at lower doses" *Proceedings of the National Academy of Sciences* 105(22):7827-7832 (2008).

Zincarelli et al. "Analysis of AAV Serotypes 1-9 Mediated Gene Expression and Tropism in Mice After Systemic Injection" *Molecular Therapy* 16(6):1073-1080 (2008).

International Search Report and Written Opinion issued in corresponding PCT Application No. PCT/US2012/024702, mailed May 4, 2012 (7 pages).

International Preliminary Report on Patentability and Written Opinion of the International Searching Authority corresponding to International Application No. PCT/US2012/024702; Date of Mailing: Aug. 22, 2013; 6 pages.

Extended European Search Report corresponding to European Patent Application No. 12744695.3 (26 pages) (mailed Aug. 24, 2015).

Partial Supplementary European Search Report corresponding to European Patent Application No. 12744695.3 (12 pages) (mailed Apr. 28, 2015).

Petrs-Silva et al. "High-efficiency Transduction of the Mouse Retina by Tyrosine-mutant AAV Serotype Vectors" *Molecular Therapy* 17(3):463-471 (2009).

Pulicherla et al. "Engineering Liver-detargeted AAV9 Vectors for Cardiac and Musculoskeletal Gene Transfer" *Molecular Therapy* 19(6):1070-1078 (2011).

Vandenberghe et al. "Naturally occurring singleton residues in AAV capsid impact vector performance and illustrate structural constraints" *Gene Therapy* 16:1416-1428 (2009).

\* cited by examiner

| Viruses | Binding Potential |
|---------|-------------------|
| AAV9    | $4.54 \times 10^{-2}$ |
| 9.24    | $1.05 \times 10^{-2}$ |
| 9.45    | $6.95 \times 10^{-3}$ |
| 9.61    | $4.39 \times 10^{-3}$ |
| 9.98    | $2.38 \times 10^{-2}$ |

Single-Site Binding Model $$Y = B_{max} * X/(K_d' + X)$$

$$Binding\ Potential = B_{max}/K_d'$$

FIG. 10

SEQUENCE LISTING

<160> NUMBER OF SEQ ID NOS: 139

<210> SEQ ID NO 1
<211> LENGTH: 736
<212> TYPE: PRT
<213> ORGANISM: adeno-associated virus 9

<400> SEQUENCE: 1

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365
```

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 2
<211> LENGTH: 7
<212> TYPE: PRT
<213> ORGANISM: Artificial
<220> FEATURE:
<223> OTHER INFORMATION: Consensus peptide targeting sequence

```
<220> FEATURE:
<221> NAME/KEY: MISC_FEATURE
<222> LOCATION: (7)..(7)
<223> OTHER INFORMATION: Xaa can be G or S

<400> SEQUENCE: 2

Asn Ser Val Arg Asp Leu Xaa
1               5

<210> SEQ ID NO 3
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 3

Pro Arg Ser Val Thr Val Pro
1               5

<210> SEQ ID NO 4
<211> LENGTH: 7
<212> TYPE: PRT
<213> ORGANISM: Artificial
<220> FEATURE:
<223> OTHER INFORMATION: Consensus peptide targeting sequence
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be S or A

<400> SEQUENCE: 4

Asn Ser Val Ser Ser Xaa Xaa
1               5

<210> SEQ ID NO 5
<211> LENGTH: 6
<212> TYPE: PRT
<213> ORGANISM: Artificial
<220> FEATURE:
<223> OTHER INFORMATION: Consensus peptide targeting sequence

<400> SEQUENCE: 5

Asn Gly Arg Ala His Ala
1               5

<210> SEQ ID NO 6
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 6

Gln Pro Glu His Ser Ser Thr
1               5

<210> SEQ ID NO 7
<211> LENGTH: 7
<212> TYPE: PRT
<213> ORGANISM: Artificial
<220> FEATURE:
<223> OTHER INFORMATION: Consensus peptide targeting sequence
```

```
<400> SEQUENCE: 7

Val Asn Thr Ala Asn Ser Thr
1               5

<210> SEQ ID NO 8
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 8

His Gly Pro Met Gln Lys Ser
1               5

<210> SEQ ID NO 9
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 9

Pro His Lys Pro Pro Leu Ala
1               5

<210> SEQ ID NO 10
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 10

Ile Lys Asn Asn Glu Met Trp
1               5

<210> SEQ ID NO 11
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 11

Arg Asn Leu Asp Thr Pro Met
1               5

<210> SEQ ID NO 12
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 12

Val Asp Ser His Arg Gln Ser
1               5

<210> SEQ ID NO 13
<211> LENGTH: 7
<212> TYPE: PRT
<213> ORGANISM: Artificial
<220> FEATURE:
<223> OTHER INFORMATION: Consensus peptide targeting sequence
```

```
<400> SEQUENCE: 13

Tyr Asp Ser Lys Thr Lys Thr
1               5

<210> SEQ ID NO 14
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 14

Ser Gln Leu Pro His Gln Lys
1               5

<210> SEQ ID NO 15
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 15

Ser Thr Met Gln Gln Asn Thr
1               5

<210> SEQ ID NO 16
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 16

Thr Glu Arg Tyr Met Thr Gln
1               5

<210> SEQ ID NO 17
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 17

Gln Pro Glu His Ser Ser Thr
1               5

<210> SEQ ID NO 18
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 18

Asp Ala Ser Leu Ser Thr Ser
1               5

<210> SEQ ID NO 19
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 19
```

```
Asp Leu Pro Asn Lys Lys Thr
1               5

<210> SEQ ID NO 20
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 20

Asp Leu Thr Ala Ala Arg Leu
1               5

<210> SEQ ID NO 21
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 21

Glu Pro His Gln Phe Asn Tyr
1               5

<210> SEQ ID NO 22
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 22

Glu Pro Gln Ser Asn His Thr
1               5

<210> SEQ ID NO 23
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 23

Met Ser Ser Trp Pro Ser Gln
1               5

<210> SEQ ID NO 24
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 24

Asn Pro Lys His Asn Ala Thr
1               5

<210> SEQ ID NO 25
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 25
```

```
Pro Asp Gly Met Arg Thr Thr
1               5

<210> SEQ ID NO 26
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 26

Pro Asn Asn Asn Lys Thr Thr
1               5

<210> SEQ ID NO 27
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 27

Gln Ser Thr Thr His Asp Ser
1               5

<210> SEQ ID NO 28
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 28

Thr Gly Ser Lys Gln Lys Gln
1               5

<210> SEQ ID NO 29
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 29

Ser Leu Lys His Gln Ala Leu
1               5

<210> SEQ ID NO 30
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 30

Ser Pro Ile Asp Gly Glu Gln
1               5

<210> SEQ ID NO 31
<211> LENGTH: 8
<212> TYPE: PRT
<213> ORGANISM: Artificial
<220> FEATURE:
<223> OTHER INFORMATION: Consensus peptide targeting sequence

<400> SEQUENCE: 31

Trp Ile Phe Pro Trp Ile Gln Leu
```

```
1               5
```

<210> SEQ ID NO 32
<211> LENGTH: 9
<212> TYPE: PRT
<213> ORGANISM: Artificial
<220> FEATURE:
<223> OTHER INFORMATION: Consensus peptide targeting sequence

<400> SEQUENCE: 32

```
Cys Asp Cys Arg Gly Asp Cys Phe Cys
1               5
```

<210> SEQ ID NO 33
<211> LENGTH: 5
<212> TYPE: PRT
<213> ORGANISM: Artificial
<220> FEATURE:
<223> OTHER INFORMATION: Consensus peptide targeting sequence

<400> SEQUENCE: 33

```
Cys Asn Gly Arg Cys
1               5
```

<210> SEQ ID NO 34
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 34

```
Cys Pro Arg Glu Cys Glu Ser
1               5
```

<210> SEQ ID NO 35
<211> LENGTH: 10
<212> TYPE: PRT
<213> ORGANISM: Artificial
<220> FEATURE:
<223> OTHER INFORMATION: Consensus peptide targeting sequence

<400> SEQUENCE: 35

```
Cys Thr Thr His Trp Gly Phe Thr Leu Cys
1               5                   10
```

<210> SEQ ID NO 36
<211> LENGTH: 9
<212> TYPE: PRT
<213> ORGANISM: Artificial
<220> FEATURE:
<223> OTHER INFORMATION: Consensus peptide targeting sequence

<400> SEQUENCE: 36

```
Cys Gly Arg Arg Ala Gly Gly Ser Cys
1               5
```

<210> SEQ ID NO 37
<211> LENGTH: 9
<212> TYPE: PRT
<213> ORGANISM: Artificial
<220> FEATURE:
<223> OTHER INFORMATION: Consensus peptide targeting sequence

<400> SEQUENCE: 37

```
Cys Lys Gly Gly Arg Ala Lys Asp Cys
1               5
```

```
<210> SEQ ID NO 38
<211> LENGTH: 9
<212> TYPE: PRT
<213> ORGANISM: Artificial
<220> FEATURE:
<223> OTHER INFORMATION: Consensus peptide targeting sequence

<400> SEQUENCE: 38

Cys Val Pro Glu Leu Gly His Glu Cys
1               5

<210> SEQ ID NO 39
<211> LENGTH: 9
<212> TYPE: PRT
<213> ORGANISM: Artificial
<220> FEATURE:
<223> OTHER INFORMATION: Consensus peptide targeting sequence

<400> SEQUENCE: 39

Cys Arg Arg Glu Thr Ala Trp Ala Lys
1               5

<210> SEQ ID NO 40
<211> LENGTH: 14
<212> TYPE: PRT
<213> ORGANISM: Artificial
<220> FEATURE:
<223> OTHER INFORMATION: Consensus peptide targeting sequence

<400> SEQUENCE: 40

Val Ser Trp Phe Ser His Arg Tyr Ser Pro Phe Ala Val Ser
1               5                   10

<210> SEQ ID NO 41
<211> LENGTH: 13
<212> TYPE: PRT
<213> ORGANISM: Artificial
<220> FEATURE:
<223> OTHER INFORMATION: Consensus peptide targeting sequence

<400> SEQUENCE: 41

Gly Tyr Arg Asp Gly Tyr Ala Gly Pro Ile Leu Tyr Asn
1               5                   10

<210> SEQ ID NO 42
<211> LENGTH: 7
<212> TYPE: PRT
<213> ORGANISM: Artificial
<220> FEATURE:
<223> OTHER INFORMATION: Consensus peptide targeting sequence
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Y is phosphyrylated
<220> FEATURE:
<221> NAME/KEY: misc_feature
<222> LOCATION: (5)..(7)
<223> OTHER INFORMATION: Xaa can be any naturally occurring amino acid

<400> SEQUENCE: 42

Xaa Xaa Xaa Tyr Xaa Xaa Xaa
1               5
```

```
<210> SEQ ID NO 43
<211> LENGTH: 4
<212> TYPE: PRT
<213> ORGANISM: Artificial
<220> FEATURE:
<223> OTHER INFORMATION: Consensus peptide targeting sequence
<220> FEATURE:
<221> NAME/KEY: MISC_FEATURE
<222> LOCATION: (1)..(1)
<223> OTHER INFORMATION: Y is phosphorylated
<220> FEATURE:
<221> NAME/KEY: misc_feature
<222> LOCATION: (2)..(2)
<223> OTHER INFORMATION: Xaa can be any naturally occurring amino acid

<400> SEQUENCE: 43

Tyr Xaa Asn Trp
1

<210> SEQ ID NO 44
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 44

Arg Pro Leu Pro Pro Leu Pro
1               5

<210> SEQ ID NO 45
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 45

Ala Pro Pro Leu Pro Pro Arg
1               5

<210> SEQ ID NO 46
<211> LENGTH: 12
<212> TYPE: PRT
<213> ORGANISM: Artificial
<220> FEATURE:
<223> OTHER INFORMATION: Consensus peptide targeting sequence

<400> SEQUENCE: 46

Asp Val Phe Tyr Pro Tyr Pro Tyr Ala Ser Gly Ser
1               5                   10

<210> SEQ ID NO 47
<211> LENGTH: 6
<212> TYPE: PRT
<213> ORGANISM: Artificial
<220> FEATURE:
<223> OTHER INFORMATION: Consensus peptide targeting sequence

<400> SEQUENCE: 47

Met Tyr Trp Tyr Pro Tyr
1               5

<210> SEQ ID NO 48
<211> LENGTH: 12
<212> TYPE: PRT
<213> ORGANISM: Artificial
<220> FEATURE:
<223> OTHER INFORMATION: Consensus peptide targeting sequence
```

<400> SEQUENCE: 48

Asp Ile Thr Trp Asp Gln Leu Trp Asp Leu Met Lys
1               5                   10

<210> SEQ ID NO 49
<211> LENGTH: 8
<212> TYPE: PRT
<213> ORGANISM: Artificial
<220> FEATURE:
<223> OTHER INFORMATION: Consensus peptide targeting sequence
<220> FEATURE:
<221> NAME/KEY: MISC_FEATURE
<222> LOCATION: (5)..(5)
<223> OTHER INFORMATION: Xaa can be G or L

<400> SEQUENCE: 49

Cys Trp Asp Asp Xaa Trp Leu Cys
1               5

<210> SEQ ID NO 50
<211> LENGTH: 14
<212> TYPE: PRT
<213> ORGANISM: Artificial
<220> FEATURE:
<223> OTHER INFORMATION: Consensus peptide targeting sequence

<400> SEQUENCE: 50

Glu Trp Cys Glu Tyr Leu Gly Gly Tyr Leu Arg Cys Tyr Ala
1               5                   10

<210> SEQ ID NO 51
<211> LENGTH: 14
<212> TYPE: PRT
<213> ORGANISM: Artificial
<220> FEATURE:
<223> OTHER INFORMATION: Consensus peptide targeting sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 51

Tyr Xaa Cys Xaa Xaa Gly Pro Xaa Thr Trp Xaa Cys Xaa Pro
1               5                   10

<210> SEQ ID NO 52
<211> LENGTH: 14
<212> TYPE: PRT
<213> ORGANISM: Artificial
<220> FEATURE:
<223> OTHER INFORMATION: Consensus peptide targeting sequence

<400> SEQUENCE: 52

```
Ile Glu Gly Pro Thr Leu Arg Gln Trp Leu Ala Ala Arg Ala
1               5                   10

<210> SEQ ID NO 53
<211> LENGTH: 5
<212> TYPE: PRT
<213> ORGANISM: Artificial
<220> FEATURE:
<223> OTHER INFORMATION: Consensus peptide targeting sequence
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be Y, W, F or H

<400> SEQUENCE: 53

Leu Trp Xaa Xaa Xaa
1               5

<210> SEQ ID NO 54
<211> LENGTH: 7
<212> TYPE: PRT
<213> ORGANISM: Artificial
<220> FEATURE:
<223> OTHER INFORMATION: Consensus peptide targeting sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 54

Xaa Phe Xaa Xaa Tyr Leu Trp
1               5

<210> SEQ ID NO 55
<211> LENGTH: 13
<212> TYPE: PRT
<213> ORGANISM: Artificial
<220> FEATURE:
<223> OTHER INFORMATION: Consensus peptide targeting sequence

<400> SEQUENCE: 55

Ser Ser Ile Ile Ser His Phe Arg Trp Gly Leu Cys Asp
1               5                   10

<210> SEQ ID NO 56
<211> LENGTH: 13
<212> TYPE: PRT
<213> ORGANISM: Artificial
<220> FEATURE:
<223> OTHER INFORMATION: Consensus peptide targeting sequence

<400> SEQUENCE: 56

Met Ser Arg Pro Ala Cys Pro Pro Asn Asp Lys Tyr Glu
1               5                   10

<210> SEQ ID NO 57
<211> LENGTH: 8
<212> TYPE: PRT
<213> ORGANISM: Artificial
<220> FEATURE:
<223> OTHER INFORMATION: Consensus peptide targeting sequence
```

```
<400> SEQUENCE: 57

Cys Leu Arg Ser Gly Arg Gly Cys
1               5

<210> SEQ ID NO 58
<211> LENGTH: 9
<212> TYPE: PRT
<213> ORGANISM: Artificial
<220> FEATURE:
<223> OTHER INFORMATION: Consensus peptide targeting sequence

<400> SEQUENCE: 58

Cys His Trp Met Phe Ser Pro Trp Cys
1               5

<210> SEQ ID NO 59
<211> LENGTH: 4
<212> TYPE: PRT
<213> ORGANISM: Artificial
<220> FEATURE:
<223> OTHER INFORMATION: Consensus peptide targeting sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 59

Trp Xaa Xaa Phe
1

<210> SEQ ID NO 60
<211> LENGTH: 8
<212> TYPE: PRT
<213> ORGANISM: Artificial
<220> FEATURE:
<223> OTHER INFORMATION: Consensus peptide targeting sequence

<400> SEQUENCE: 60

Cys Ser Ser Arg Leu Asp Ala Cys
1               5

<210> SEQ ID NO 61
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 61

Cys Leu Pro Val Ala Ser Cys
1               5

<210> SEQ ID NO 62
<211> LENGTH: 13
<212> TYPE: PRT
<213> ORGANISM: Artificial
<220> FEATURE:
<223> OTHER INFORMATION: Consensus peptide targeting sequence

<400> SEQUENCE: 62

Cys Gly Phe Glu Cys Val Arg Gln Cys Pro Glu Arg Cys
1               5                   10

<210> SEQ ID NO 63
<211> LENGTH: 13
<212> TYPE: PRT
<213> ORGANISM: Artificial
```

```
<220> FEATURE:
<223> OTHER INFORMATION: Consensus peptide targeting sequence

<400> SEQUENCE: 63

Cys Val Ala Leu Cys Arg Glu Ala Cys Gly Glu Gly Cys
1               5                   10

<210> SEQ ID NO 64
<211> LENGTH: 9
<212> TYPE: PRT
<213> ORGANISM: Artificial
<220> FEATURE:
<223> OTHER INFORMATION: Consensus peptide targeting sequence

<400> SEQUENCE: 64

Ser Trp Cys Glu Pro Gly Trp Cys Arg
1               5

<210> SEQ ID NO 65
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 65

Tyr Ser Gly Lys Trp Gly Trp
1               5

<210> SEQ ID NO 66
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 66

Gly Leu Ser Gly Gly Arg Ser
1               5

<210> SEQ ID NO 67
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 67

Leu Met Leu Pro Arg Ala Asp
1               5

<210> SEQ ID NO 68
<211> LENGTH: 9
<212> TYPE: PRT
<213> ORGANISM: Artificial
<220> FEATURE:
<223> OTHER INFORMATION: Consensus peptide targeting sequence

<400> SEQUENCE: 68

Cys Ser Cys Phe Arg Asp Val Cys Cys
1               5

<210> SEQ ID NO 69
<211> LENGTH: 9
<212> TYPE: PRT
<213> ORGANISM: Artificial
<220> FEATURE:
```

```
<223> OTHER INFORMATION: Consensus peptide targeting sequence

<400> SEQUENCE: 69

Cys Arg Asp Val Val Ser Val Ile Cys
1               5

<210> SEQ ID NO 70
<211> LENGTH: 5
<212> TYPE: PRT
<213> ORGANISM: Artificial
<220> FEATURE:
<223> OTHER INFORMATION: Consensus peptide targeting sequence

<400> SEQUENCE: 70

Cys Asn Gly Arg Cys
1               5

<210> SEQ ID NO 71
<211> LENGTH: 6
<212> TYPE: PRT
<213> ORGANISM: Artificial
<220> FEATURE:
<223> OTHER INFORMATION: Consensus peptide targeting sequence

<400> SEQUENCE: 71

Met Ala Arg Ser Gly Leu
1               5

<210> SEQ ID NO 72
<211> LENGTH: 6
<212> TYPE: PRT
<213> ORGANISM: Artificial
<220> FEATURE:
<223> OTHER INFORMATION: Consensus peptide targeting sequence

<400> SEQUENCE: 72

Met Ala Arg Ala Lys Glu
1               5

<210> SEQ ID NO 73
<211> LENGTH: 6
<212> TYPE: PRT
<213> ORGANISM: Artificial
<220> FEATURE:
<223> OTHER INFORMATION: Consensus peptide targeting sequence

<400> SEQUENCE: 73

Met Ser Arg Thr Met Ser
1               5

<210> SEQ ID NO 74
<211> LENGTH: 6
<212> TYPE: PRT
<213> ORGANISM: Artificial
<220> FEATURE:
<223> OTHER INFORMATION: Consensus peptide targeting sequence

<400> SEQUENCE: 74

Lys Cys Cys Tyr Ser Leu
1               5

<210> SEQ ID NO 75
<211> LENGTH: 14
<212> TYPE: PRT
<213> ORGANISM: Artificial
<220> FEATURE:
<223> OTHER INFORMATION: Consensus peptide targeting sequence
```

<400> SEQUENCE: 75

Met Tyr Trp Gly Asp Ser His Trp Leu Gln Tyr Trp Tyr Glu
1               5                   10

<210> SEQ ID NO 76
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 76

Met Gln Leu Pro Leu Ala Thr
1               5

<210> SEQ ID NO 77
<211> LENGTH: 4
<212> TYPE: PRT
<213> ORGANISM: Artificial
<220> FEATURE:
<223> OTHER INFORMATION: Consensus peptide targeting sequence

<400> SEQUENCE: 77

Glu Trp Leu Ser
1

<210> SEQ ID NO 78
<211> LENGTH: 4
<212> TYPE: PRT
<213> ORGANISM: Artificial
<220> FEATURE:
<223> OTHER INFORMATION: Consensus peptide targeting sequence

<400> SEQUENCE: 78

Ser Asn Glu Trp
1

<210> SEQ ID NO 79
<211> LENGTH: 4
<212> TYPE: PRT
<213> ORGANISM: Artificial
<220> FEATURE:
<223> OTHER INFORMATION: Consensus peptide targeting sequence

<400> SEQUENCE: 79

Thr Asn Tyr Leu
1

<210> SEQ ID NO 80
<211> LENGTH: 8
<212> TYPE: PRT
<213> ORGANISM: Artificial
<220> FEATURE:
<223> OTHER INFORMATION: Consensus peptide targeting sequence

<400> SEQUENCE: 80

Trp Ile Phe Pro Trp Ile Gln Leu
1               5

<210> SEQ ID NO 81
<211> LENGTH: 12
<212> TYPE: PRT
<213> ORGANISM: Artificial
<220> FEATURE:
<223> OTHER INFORMATION: Consensus peptide targeting sequence

```
<400> SEQUENCE: 81

Trp Asp Leu Ala Trp Met Phe Arg Leu Pro Val Gly
1               5                   10

<210> SEQ ID NO 82
<211> LENGTH: 13
<212> TYPE: PRT
<213> ORGANISM: Artificial
<220> FEATURE:
<223> OTHER INFORMATION: Consensus peptide targeting sequence

<400> SEQUENCE: 82

Cys Thr Val Ala Leu Pro Gly Gly Tyr Val Arg Val Cys
1               5                   10

<210> SEQ ID NO 83
<211> LENGTH: 9
<212> TYPE: PRT
<213> ORGANISM: Artificial
<220> FEATURE:
<223> OTHER INFORMATION: Consensus peptide targeting sequence

<400> SEQUENCE: 83

Cys Val Pro Glu Leu Gly His Glu Cys
1               5

<210> SEQ ID NO 84
<211> LENGTH: 9
<212> TYPE: PRT
<213> ORGANISM: Artificial
<220> FEATURE:
<223> OTHER INFORMATION: Consensus peptide targeting sequence

<400> SEQUENCE: 84

Cys Gly Arg Arg Ala Gly Gly Ser Cys
1               5

<210> SEQ ID NO 85
<211> LENGTH: 13
<212> TYPE: PRT
<213> ORGANISM: Artificial
<220> FEATURE:
<223> OTHER INFORMATION: Consensus peptide targeting sequence

<400> SEQUENCE: 85

Cys Val Ala Tyr Cys Ile Glu His His Cys Trp Thr Cys
1               5                   10

<210> SEQ ID NO 86
<211> LENGTH: 12
<212> TYPE: PRT
<213> ORGANISM: Artificial
<220> FEATURE:
<223> OTHER INFORMATION: Consensus peptide targeting sequence

<400> SEQUENCE: 86

Cys Val Phe Ala His Asn Tyr Asp Tyr Leu Val Cys
1               5                   10

<210> SEQ ID NO 87
<211> LENGTH: 10
<212> TYPE: PRT
<213> ORGANISM: Artificial
<220> FEATURE:
<223> OTHER INFORMATION: Consensus peptide targeting sequence

<400> SEQUENCE: 87
```

```
Cys Val Phe Thr Ser Asn Tyr Ala Phe Cys
1               5                   10

<210> SEQ ID NO 88
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 88

Val His Ser Pro Asn Lys Lys
1               5

<210> SEQ ID NO 89
<211> LENGTH: 9
<212> TYPE: PRT
<213> ORGANISM: Artificial
<220> FEATURE:
<223> OTHER INFORMATION: Consensus peptide targeting sequence

<400> SEQUENCE: 89

Cys Asp Cys Arg Gly Asp Cys Phe Cys
1               5

<210> SEQ ID NO 90
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 90

Cys Arg Gly Asp Gly Trp Cys
1               5

<210> SEQ ID NO 91
<211> LENGTH: 6
<212> TYPE: PRT
<213> ORGANISM: Artificial
<220> FEATURE:
<223> OTHER INFORMATION: Consensus peptide targeting sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 91

Xaa Arg Gly Cys Asp Xaa
1               5

<210> SEQ ID NO 92
<211> LENGTH: 4
<212> TYPE: PRT
<213> ORGANISM: Artificial
<220> FEATURE:
<223> OTHER INFORMATION: Consensus peptide targeting sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa is S or T
```

```
<400> SEQUENCE: 92

Pro Xaa Xaa Xaa
1

<210> SEQ ID NO 93
<211> LENGTH: 10
<212> TYPE: PRT
<213> ORGANISM: Artificial
<220> FEATURE:
<223> OTHER INFORMATION: Consensus peptide targeting sequence

<400> SEQUENCE: 93

Cys Thr Thr His Trp Gly Phe Thr Leu Cys
1               5                   10

<210> SEQ ID NO 94
<211> LENGTH: 11
<212> TYPE: PRT
<213> ORGANISM: Artificial
<220> FEATURE:
<223> OTHER INFORMATION: Consensus peptide targeting sequence

<400> SEQUENCE: 94

Ser Gly Lys Gly Pro Arg Gln Ile Thr Ala Leu
1               5                   10

<210> SEQ ID NO 95
<211> LENGTH: 6
<212> TYPE: PRT
<213> ORGANISM: Artificial
<220> FEATURE:
<223> OTHER INFORMATION: Consensus peptide targeting sequence
<220> FEATURE:
<221> NAME/KEY: MISC_FEATURE
<222> LOCATION: (2)..(2)
<223> OTHER INFORMATION: Xaa can be A or Q
<220> FEATURE:
<221> NAME/KEY: MISC_FEATURE
<222> LOCATION: (3)..(3)
<223> OTHER INFORMATION: Xaa can be N or A
<220> FEATURE:
<221> NAME/KEY: MISC_FEATURE
<222> LOCATION: (4)..(4)
<223> OTHER INFORMATION: Xaa can be L or Y
<220> FEATURE:
<221> NAME/KEY: MISC_FEATURE
<222> LOCATION: (5)..(5)
<223> OTHER INFORMATION: Xaa can be T, V, M or R
<220> FEATURE:
<221> NAME/KEY: MISC_FEATURE
<222> LOCATION: (6)..(6)
<223> OTHER INFORMATION: Xaa can be R or K

<400> SEQUENCE: 95

Ala Xaa Xaa Xaa Xaa Xaa
1               5

<210> SEQ ID NO 96
<211> LENGTH: 6
<212> TYPE: PRT
<213> ORGANISM: Artificial
<220> FEATURE:
<223> OTHER INFORMATION: Consensus peptide targeting sequence

<400> SEQUENCE: 96

Val Tyr Met Ser Pro Phe
1               5
```

```
<210> SEQ ID NO 97
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 97

Met Gln Leu Pro Leu Ala Thr
1               5

<210> SEQ ID NO 98
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 98

Ala Thr Trp Leu Pro Pro Arg
1               5

<210> SEQ ID NO 99
<211> LENGTH: 12
<212> TYPE: PRT
<213> ORGANISM: Artificial
<220> FEATURE:
<223> OTHER INFORMATION: Consensus peptide targeting sequence

<400> SEQUENCE: 99

His Thr Met Tyr Tyr His His Tyr Gln His His Leu
1               5                   10

<210> SEQ ID NO 100
<211> LENGTH: 19
<212> TYPE: PRT
<213> ORGANISM: Artificial
<220> FEATURE:
<223> OTHER INFORMATION: Consensus peptide targeting sequence

<400> SEQUENCE: 100

Ser Glu Val Gly Cys Arg Ala Gly Pro Leu Gln Trp Leu Cys Glu Lys
1               5                   10                  15

Tyr Phe Gly

<210> SEQ ID NO 101
<211> LENGTH: 18
<212> TYPE: PRT
<213> ORGANISM: Artificial
<220> FEATURE:
<223> OTHER INFORMATION: Consensus peptide targeting sequence

<400> SEQUENCE: 101

Cys Gly Leu Leu Pro Val Gly Arg Pro Asp Arg Asn Val Trp Arg Trp
1               5                   10                  15

Leu Cys

<210> SEQ ID NO 102
<211> LENGTH: 15
<212> TYPE: PRT
<213> ORGANISM: Artificial
<220> FEATURE:
<223> OTHER INFORMATION: Consensus peptide targeting sequence

<400> SEQUENCE: 102

Cys Lys Gly Gln Cys Asp Arg Phe Lys Gly Leu Pro Trp Glu Cys
```

```
                  1               5              10              15

<210> SEQ ID NO 103
<211> LENGTH: 5
<212> TYPE: PRT
<213> ORGANISM: Artificial
<220> FEATURE:
<223> OTHER INFORMATION: Consensus peptide targeting sequence

<400> SEQUENCE: 103

Ser Gly Arg Ser Ala
1               5

<210> SEQ ID NO 104
<211> LENGTH: 4
<212> TYPE: PRT
<213> ORGANISM: Artificial
<220> FEATURE:
<223> OTHER INFORMATION: Consensus peptide targeting sequence

<400> SEQUENCE: 104

Trp Gly Phe Pro
1

<210> SEQ ID NO 105
<211> LENGTH: 7
<212> TYPE: PRT
<213> ORGANISM: Artificial
<220> FEATURE:
<223> OTHER INFORMATION: Consensus peptide targeting sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 105

Xaa Phe Xaa Xaa Tyr Leu Trp
1               5

<210> SEQ ID NO 106
<211> LENGTH: 17
<212> TYPE: PRT
<213> ORGANISM: Artificial
<220> FEATURE:
<223> OTHER INFORMATION: Consensus peptide targeting sequence

<400> SEQUENCE: 106

Ala Glu Pro Met Pro His Ser Leu Asn Phe Ser Gln Tyr Leu Trp Tyr
1               5                   10                  15

Thr

<210> SEQ ID NO 107
<211> LENGTH: 6
<212> TYPE: PRT
<213> ORGANISM: Artificial
<220> FEATURE:
<223> OTHER INFORMATION: Consensus peptide targeting sequence
<220> FEATURE:
<221> NAME/KEY: MISC_FEATURE
<222> LOCATION: (4)..(4)
<223> OTHER INFORMATION: Xaa can be W or F

<400> SEQUENCE: 107

Trp Ala Tyr Xaa Ser Pro
```

<210> SEQ ID NO 108
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 108

Ile Glu Leu Leu Gln Ala Arg
1               5

<210> SEQ ID NO 109
<211> LENGTH: 12
<212> TYPE: PRT
<213> ORGANISM: Artificial
<220> FEATURE:
<223> OTHER INFORMATION: Consensus peptide targeting sequence

<400> SEQUENCE: 109

Asp Ile Thr Trp Asp Gln Leu Trp Asp Leu Met Lys
1               5                   10

<210> SEQ ID NO 110
<211> LENGTH: 16
<212> TYPE: PRT
<213> ORGANISM: Artificial
<220> FEATURE:
<223> OTHER INFORMATION: Consensus peptide targeting sequence

<400> SEQUENCE: 110

Ala Tyr Thr Lys Cys Ser Arg Gln Trp Arg Thr Cys Met Thr Thr His
1               5                   10                  15

<210> SEQ ID NO 111
<211> LENGTH: 15
<212> TYPE: PRT
<213> ORGANISM: Artificial
<220> FEATURE:
<223> OTHER INFORMATION: Consensus peptide targeting sequence

<400> SEQUENCE: 111

Pro Gln Asn Ser Lys Ile Pro Gly Pro Thr Phe Leu Asp Pro His
1               5                   10                  15

<210> SEQ ID NO 112
<211> LENGTH: 15
<212> TYPE: PRT
<213> ORGANISM: Artificial
<220> FEATURE:
<223> OTHER INFORMATION: Consensus peptide targeting sequence

<400> SEQUENCE: 112

Ser Met Glu Pro Ala Leu Pro Asp Trp Trp Trp Lys Met Phe Lys
1               5                   10                  15

<210> SEQ ID NO 113
<211> LENGTH: 16
<212> TYPE: PRT
<213> ORGANISM: Artificial
<220> FEATURE:
<223> OTHER INFORMATION: Consensus peptide targeting sequence

<400> SEQUENCE: 113

Ala Asn Thr Pro Cys Gly Pro Tyr Thr His Asp Cys Pro Val Lys Arg
1               5                   10                  15

<210> SEQ ID NO 114
<211> LENGTH: 12
<212> TYPE: PRT
<213> ORGANISM: Artificial
<220> FEATURE:
<223> OTHER INFORMATION: Consensus peptide targeting sequence

<400> SEQUENCE: 114

Thr Ala Cys His Gln His Val Arg Met Val Arg Pro
1               5                   10

<210> SEQ ID NO 115
<211> LENGTH: 12
<212> TYPE: PRT
<213> ORGANISM: Artificial
<220> FEATURE:
<223> OTHER INFORMATION: Consensus peptide targeting sequence

<400> SEQUENCE: 115

Val Pro Trp Met Glu Pro Ala Tyr Gln Arg Phe Leu
1               5                   10

<210> SEQ ID NO 116
<211> LENGTH: 8
<212> TYPE: PRT
<213> ORGANISM: Artificial
<220> FEATURE:
<223> OTHER INFORMATION: Consensus peptide targeting sequence

<400> SEQUENCE: 116

Asp Pro Arg Ala Thr Pro Gly Ser
1               5

<210> SEQ ID NO 117
<211> LENGTH: 12
<212> TYPE: PRT
<213> ORGANISM: Artificial
<220> FEATURE:
<223> OTHER INFORMATION: Consensus peptide targeting sequence

<400> SEQUENCE: 117

Phe Arg Pro Asn Arg Ala Gln Asp Tyr Asn Thr Asn
1               5                   10

<210> SEQ ID NO 118
<211> LENGTH: 9
<212> TYPE: PRT
<213> ORGANISM: Artificial
<220> FEATURE:
<223> OTHER INFORMATION: Consensus peptide targeting sequence

<400> SEQUENCE: 118

Cys Thr Lys Asn Ser Tyr Leu Met Cys
1               5

<210> SEQ ID NO 119
<211> LENGTH: 11
<212> TYPE: PRT
<213> ORGANISM: Artificial
<220> FEATURE:
<223> OTHER INFORMATION: Consensus peptide targeting sequence
<220> FEATURE:
<221> NAME/KEY: MISC_FEATURE
<222> LOCATION: (2)..(2)
<223> OTHER INFORMATION: Xaa can be R or Q
<220> FEATURE:
<221> NAME/KEY: MISC_FEATURE

```
<222> LOCATION: (3)..(3)
<223> OTHER INFORMATION: Xaa can be L or R
<220> FEATURE:
<221> NAME/KEY: MISC_FEATURE
<222> LOCATION: (5)..(5)
<223> OTHER INFORMATION: Xaa can be G or N
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be A or V

<400> SEQUENCE: 119

Cys Xaa Xaa Thr Xaa Xaa Xaa Gly Xaa Gly Cys
1               5                   10

<210> SEQ ID NO 120
<211> LENGTH: 9
<212> TYPE: PRT
<213> ORGANISM: Artificial
<220> FEATURE:
<223> OTHER INFORMATION: Consensus peptide targeting sequence

<400> SEQUENCE: 120

Cys Pro Ile Glu Asp Arg Pro Met Cys
1               5

<210> SEQ ID NO 121
<211> LENGTH: 12
<212> TYPE: PRT
<213> ORGANISM: Artificial
<220> FEATURE:
<223> OTHER INFORMATION: Consensus peptide targeting sequence

<400> SEQUENCE: 121

His Glu Trp Ser Tyr Leu Ala Pro Tyr Pro Trp Phe
1               5                   10

<210> SEQ ID NO 122
<211> LENGTH: 9
<212> TYPE: PRT
<213> ORGANISM: Artificial
<220> FEATURE:
<223> OTHER INFORMATION: Consensus peptide targeting sequence

<400> SEQUENCE: 122

Met Cys Pro Lys His Pro Leu Gly Cys
1               5

<210> SEQ ID NO 123
<211> LENGTH: 15
<212> TYPE: PRT
<213> ORGANISM: Artificial
<220> FEATURE:
<223> OTHER INFORMATION: Consensus peptide targeting sequence

<400> SEQUENCE: 123

Arg Met Trp Pro Ser Ser Thr Val Asn Leu Ser Ala Gly Arg Arg
1               5                   10                  15

<210> SEQ ID NO 124
<211> LENGTH: 20
<212> TYPE: PRT
<213> ORGANISM: Artificial
<220> FEATURE:
<223> OTHER INFORMATION: Consensus peptide targeting sequence
```

<400> SEQUENCE: 124

Ser Ala Lys Thr Ala Val Ser Gln Arg Val Trp Leu Pro Ser His Arg
1               5                   10                  15

Gly Gly Glu Pro
            20

<210> SEQ ID NO 125
<211> LENGTH: 20
<212> TYPE: PRT
<213> ORGANISM: Artificial
<220> FEATURE:
<223> OTHER INFORMATION: Consensus peptide targeting sequence

<400> SEQUENCE: 125

Lys Ser Arg Glu His Val Asn Asn Ser Ala Cys Pro Ser Lys Arg Ile
1               5                   10                  15

Thr Ala Ala Leu
            20

<210> SEQ ID NO 126
<211> LENGTH: 4
<212> TYPE: PRT
<213> ORGANISM: Artificial
<220> FEATURE:
<223> OTHER INFORMATION: Consensus peptide targeting sequence

<400> SEQUENCE: 126

Glu Gly Phe Arg
1

<210> SEQ ID NO 127
<211> LENGTH: 6
<212> TYPE: PRT
<213> ORGANISM: Artificial
<220> FEATURE:
<223> OTHER INFORMATION: Consensus peptide targeting sequence

<400> SEQUENCE: 127

Ala Gly Leu Gly Val Arg
1               5

<210> SEQ ID NO 128
<211> LENGTH: 15
<212> TYPE: PRT
<213> ORGANISM: Artificial
<220> FEATURE:
<223> OTHER INFORMATION: Consensus peptide targeting sequence

<400> SEQUENCE: 128

Gly Thr Arg Gln Gly His Thr Met Arg Leu Gly Val Ser Asp Gly
1               5                   10                  15

<210> SEQ ID NO 129
<211> LENGTH: 15
<212> TYPE: PRT
<213> ORGANISM: Artificial
<220> FEATURE:
<223> OTHER INFORMATION: Consensus peptide targeting sequence

<400> SEQUENCE: 129

Ile Ala Gly Leu Ala Thr Pro Gly Trp Ser His Trp Leu Ala Leu
1               5                   10                  15

<210> SEQ ID NO 130

```
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 130

Ser Met Ser Ile Ala Arg Leu
1               5

<210> SEQ ID NO 131
<211> LENGTH: 7
<212> TYPE: PRT
<213> ORGANISM: Artificial
<220> FEATURE:
<223> OTHER INFORMATION: Consensus peptide targeting sequence

<400> SEQUENCE: 131

His Thr Phe Glu Pro Gly Val
1               5

<210> SEQ ID NO 132
<211> LENGTH: 15
<212> TYPE: PRT
<213> ORGANISM: Artificial
<220> FEATURE:
<223> OTHER INFORMATION: Consensus peptide targeting sequence

<400> SEQUENCE: 132

Asn Thr Ser Leu Lys Arg Ile Ser Asn Lys Arg Ile Arg Arg Lys
1               5                   10                  15

<210> SEQ ID NO 133
<211> LENGTH: 15
<212> TYPE: PRT
<213> ORGANISM: Artificial
<220> FEATURE:
<223> OTHER INFORMATION: Consensus peptide targeting sequence

<400> SEQUENCE: 133

Leu Arg Ile Lys Arg Lys Arg Arg Lys Arg Lys Lys Thr Arg Lys
1               5                   10                  15

<210> SEQ ID NO 134
<211> LENGTH: 27
<212> TYPE: DNA
<213> ORGANISM: Artificial
<220> FEATURE:
<223> OTHER INFORMATION: PCR primer sequence

<400> SEQUENCE: 134
ggtcgttcgt cctttactg cctggaa                                           27

<210> SEQ ID NO 135
<211> LENGTH: 27
<212> TYPE: DNA
<213> ORGANISM: Artificial
<220> FEATURE:
<223> OTHER INFORMATION: PCR primer sequence

<400> SEQUENCE: 135
gccgtccgtg tgaggaattt tggccca                                          27

<210> SEQ ID NO 136
<211> LENGTH: 20
<212> TYPE: DNA
<213> ORGANISM: Artificial
```

```
<220> FEATURE:
<223> OTHER INFORMATION: qPCR primer sequence

<400> SEQUENCE: 136
cgtcaatggg tggagtattt                                              20

<210> SEQ ID NO 137
<211> LENGTH: 21
<212> TYPE: DNA
<213> ORGANISM: Artificial
<220> FEATURE:
<223> OTHER INFORMATION: qPCR primer sequence

<400> SEQUENCE: 137
gcgatgacta atacgtagat g                                            21

<210> SEQ ID NO 138
<211> LENGTH: 24
<212> TYPE: DNA
<213> ORGANISM: Artificial
<220> FEATURE:
<223> OTHER INFORMATION: qPCR primer sequence

<400> SEQUENCE: 138
aaaagcactc tgattgacaa atac                                         24

<210> SEQ ID NO 139
<211> LENGTH: 22
<212> TYPE: DNA
<213> ORGANISM: Artificial
<220> FEATURE:
<223> OTHER INFORMATION: qPCR primer sequence

<400> SEQUENCE: 139
ccttcgcttc aaaaaatgga ac                                           22
```

VIRAL VECTORS WITH MODIFIED TRANSDUCTION PROFILES AND METHODS OF MAKING AND USING THE SAME

STATEMENT OF PRIORITY

This application is a 35 U.S.C. §371 national phase application of International Application Serial No. PCT/US2012/024702, filed Feb. 10, 2012, which claims the benefit, under 35 U.S.C. §119(e), of U.S. Provisional Application No. 61/441,411, filed Feb. 10, 2011, the entire contents of each of which are incorporated herein by reference.

STATEMENT OF GOVERNMENT SUPPORT

This invention was made with government support under Grant No. HL089221 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. §1.821, entitled 5470-587WO_ST25.txt, 37,855 bytes in size, generated on Aug. 8, 2013 and filed via EFS-Web, is provided in lieu of a paper copy. This Sequence Listing is hereby incorporated by reference into the specification for its disclosures.

FIELD OF THE INVENTION

The present invention relates to modified capsid proteins from adeno-associated virus (AAV) and virus capsids and virus vectors comprising the same. In particular, the invention relates to modified AAV capsid proteins and capsids comprising the same that can be incorporated into virus vectors to confer a desirable transduction profile with respect to a target tissue(s) of interest.

BACKGROUND OF THE INVENTION

Clinical gene transfer with adeno-associated viral (AAV) vectors has rapidly gained momentum in recent years. The ongoing translation from bench-to-bedside has been spurred in part by the availability of a versatile AAV toolkit displaying diverse tissue tropisms across multiple species [1,2]. Amongst numerous AAV isolates, AAV9 vectors display a systemic, multi-organ transduction profile following intravenous administration [3]. Rapid onset of gene expression and high transgene expression levels mediated by AAV9 vectors in heart and liver have been reported [4,5,6]. In addition, efficient transduction of neurons in neonatal mice as well as skeletal muscle in neonatal dogs following intravascular administration has been observed [7, 8]. These attributes make AAV9 a viable candidate for therapeutic gene transfer in systemic diseases such as lysosomal storage disorders.

Paradoxically, a wide range of clinically relevant applications benefit from vector targeting to specific tissues rather than multi-organ gene expression. For instance, gene therapy of cardiac disease or muscular dystrophies would be facilitated by vectors capable of efficient and selective gene transfer to heart and/or skeletal muscle [6,8,9]. Therapeutic approaches targeting the liver or skeletal muscle are preferred for treatment of hemophilic disorders [10], while the lung is considered a target organ for gene therapy of alpha-1 antitrypsin (AAT) deficiency [11,12].

The present inventor addresses a need in the art for nucleic acid delivery vectors with desirable features, e.g., with respect to transduction profiles.

SUMMARY OF THE INVENTION

In one aspect, the present invention provides an adeno-associated virus serotype 9 (AAV9) or a Clade F adeno-associated virus (AAV) capsid protein, wherein the capsid protein comprises a mutation in one or more amino acids in amino acid regions 498-504, 590-595 and/or 582-587, wherein the mutation(s) result in a phenotype of decreased liver transduction as compared to a control (e.g., an AAV9 or Clade F AAV capsid protein lacking said mutation(s)).

In an additional aspect, the present invention provides an adeno-associated virus serotype 9 (AAV9) or a Clade F adeno-associated virus (AAV) capsid protein, wherein the capsid protein comprises a mutation in one or more amino acids in amino acid regions 498-504, 590-595 and/or 582-587, wherein the mutation(s) result in a phenotype of reduced glycan binding affinity as compared to a control (e.g., an AAV9 or Clade F AAV capsid protein lacking said mutation(s)).

In a further aspect, the present invention provides a virus capsid (e.g., an AAV capsid) comprising the AAV9 or Clade F AAV capsid protein of this invention.

Additionally provided herein is a virus vector comprising a virus capsid (e.g., an AAV capsid) of this invention; and a nucleic acid comprising at least one terminal repeat sequence, wherein the nucleic acid is encapsidated by the AAV capsid.

The present invention also provides a composition comprising the virus vector of this invention in a pharmaceutically acceptable carrier.

In further aspects, the present invention provides a method of introducing a nucleic acid into a cell, comprising contacting the cell with a virus vector and/or a composition of this invention.

Also provided herein is a method of delivering a nucleic acid to a subject (e.g., a human subject), comprising administering to the subject a virus vector of this invention and/or a composition of this invention.

These and other aspects of the invention are addressed in more detail in the description of the invention set forth below.

BRIEF DESCRIPTION OF THE DRAWINGS

FIG. 10. Binding potentials of AAV9 mutants on Lec2 cell surface.

DETAILED DESCRIPTION OF THE INVENTION

Figure 1A:
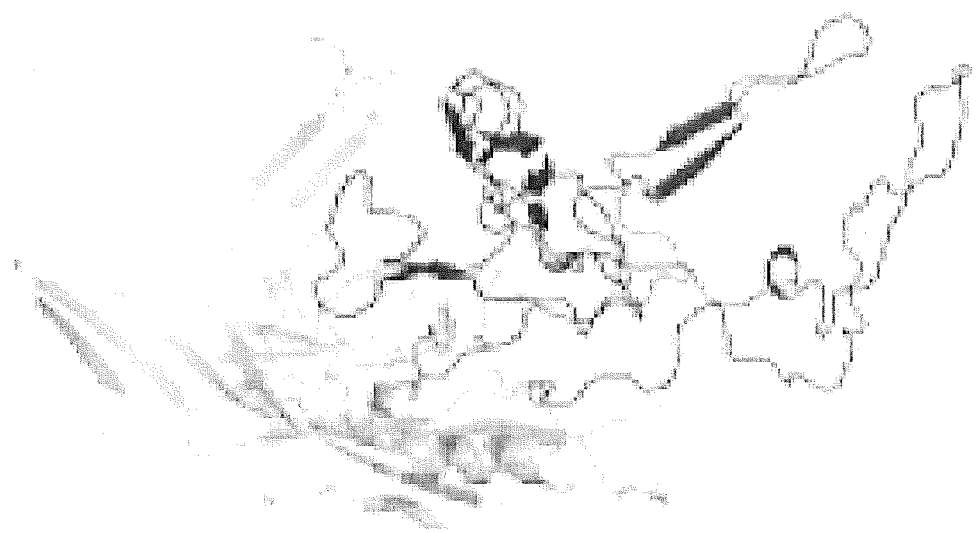
FIGS. 1A-E. Structural analysis of the AAV9 capsid library. (A) Cartoon representation of the AAV9 VP3 subunit monomer obtained using SWISS-MODEL with crystal structure of AAV8 serving as template (pdb id: 2QA0). The GH loop containing amino acids 390-627 (VP1 numbering) is colored in red. (B) Surface rendering of an AAV9 capsid model with 60 VP3 subunits generated using T=1 icosahedral symmetry coordinates on VIPERdb. GH loop regions from different VP3 subunits, surrounding the icosahedral five-fold pore and interdigitating at the three-fold symmetry axis are highlighted in red. (C) Cartoon of AAV9 VP3 subunit trimer generated on VIPERdb with point mutations of 43 representative clones from the AAV9 library depicted by red spheres. (D) Side view of capsid trimer (90° rotation) showing a majority of point mutations (red spheres) clustered on the outer loops. (E) Spherical roadmap projection of surface residues within the capsid trimer region. Residues highlighted in red represent a subset of ten AAV9 variants containing altered residues prominently located on the capsid surface.
Figure 1B:
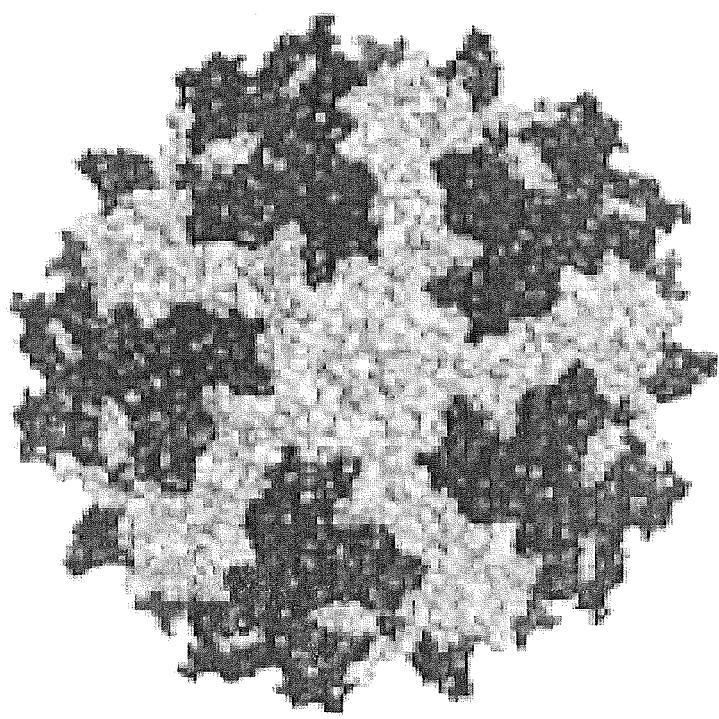

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference herein in their entirety.

The designation of all amino acid positions in the AAV capsid proteins in the description of the invention and the appended claims is with respect to AAV9 VP1 capsid subunit numbering (AAV9 VP1 capsid protein; GenBank® Database Accession No. AY530579.1; GenBank® Database Accession No. AAS99264.1). It will be understood by those skilled in the art that the modifications described herein if inserted into the AAV cap gene may result in modifications in the VP1, VP2 and/or VP3 capsid subunits. Alternatively, the capsid subunits can be expressed independently to achieve modification in only one or two of the capsid subunits (VP1, VP2, VP3, VP1+VP2, VP1+VP3, or VP2+VP3). The amino acid sequence of AAV9 VP1 capsid protein (SEQ ID NO:1) is provided below. Amino acids 498-504, 582-587 and 590-595 are shown in upper case.

```
  1 maadgylpdw lednlsegir ewwalkpgap qpkanqqhqd narglvlpgy kylgpgngld
 61 kgepvnaada aalehdkayd qqlkagdnpy lkynhadaef qerlkedtsf ggnlgravfq
121 akkrlleplg lveeaaktap gkkrpveqsp qepdssagig ksgaqpakkr lnfgqtgdte
181 svpdpqpige ppaapsgvgs ltmasgggap vadnnegadg vgsssgnwhc dsqwlgdrvi
```

```
-continued
241 ttstrtwalp  tynnhlykqi  snstsggssn  dnayfgystp  wgyfdfnrfh  chfsprdwqr 301 linnnwgfrp  krlnfklfni  qvkevtdnng  vktiannlts  tvqvftdsdy  qlpyvlgsah 361 egclppfpad  vfmipqygyl  tlndgsqavg  rssfycleyf  psqmlrtgnn  fqfsyefenv 421 pfhssyahsq  sldrlmnpli  dqylyylskt  ingsgqnqqt  lkfsvagpsn  mavqgrnyip 481 gpsyrqqrvs  ttvtqnnNSE  FAWPgasswa  lngrnslmnp  gpamashkeg  edrffplsgs 541 lifgkqgtgr  dnvdadkvmi  tneeeikttn  pvatesygqv  aTNHQSAqaQ  AQTGWvqnqg 601 ilpgmvwqdr  dvylqgpiwa  kiphtdgnfh  psplmggfgm  khpppqilik  ntpvpadppt 661 afnkdklnsf  itgystgqvs  veiewelqke  nskrwnpeiq  ytsnyyksnn  vefavntegv 721 yseprpigtr  yltrnl
```

DEFINITIONS

The singular forms "a," "an" and "the" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

As used herein, the terms "reduce," "reduces," "reduction" and similar terms mean a decrease of at least about 5%, 10%, 15%, 20%, 25%, 35%, 50%, 75%, 80%, 85%, 90%, 95%, 97%, 98%, 99%, 100% or more.

As used herein, the terms "enhance," "enhances," "enhancement" and similar terms indicate an increase of at least about 10%, 20%, 25%, 50%, 75%, 100%, 150%, 200%, 300%, 400%, 500% or more.

The term "parvovirus" as used herein encompasses the family Parvoviridae, including autonomously replicating parvoviruses and dependoviruses. The autonomous parvoviruses include members of the genera Parvovirus, Bythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., BERNARD N. FIELDS et al., VIROLOGY, volume 2, chapter 69 (4th ed., Lippincott-Raven Publishers).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, ovine AAV, Clade F AAV (Table 1) and any other AAV now known or later discovered. See, e.g., BERNARD N. FIELDS et al., VIROLOGY, volume 2, chapter 69 (4th ed., Lippincott-Raven Publishers). A number of relatively new AAV serotypes and clades have been identified (see, e.g., Gao et al. (2004) J. Virology 78:6381-6388; Moris et al. (2004) Virology 33:375-383; and Table 1).

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as GenBank® Database. See, e.g., GenBank® Database Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al. (1983) J. Virology 45:555; Chiorini et al. (1998) J. Virology 71:6823; Chiorini et al. (1999) J. Virology 73:1309; Bantel-Schaal et al. (1999) J. Virology 73:939; Xiao et al. (1999) J. Virology 73:3994; Muramatsu et al. (1996) Virology 221:208; Shade et al. (1986) J. Virol. 58:921; Gao et al. (2002) Proc. Nat. Acad. Sci. USA 99:11854; Moris et al. (2004) Virology 33:375-383; international patent publications WO 00/28061, WO 99/6160 and WO 98/11244; and U.S. Pat. No. 6,156,303; the disclosures of which are incorporated by reference herein for teaching parvovirus and AAV nucleic acid and amino acid sequences. See also Table 1.

The capsid structures of autonomous parvoviruses and AAV are described in more detail in BERNARD N. FIELDS et al., Virology, Volume 2, Chapters 69 & 70 (4th ed., Lippincott-Raven Publishers). See also, description of the crystal structure of AAV2 (Xie et al. (2002) Proc. Nat. Acad. Sci. 99:10405-10), AAV4 (Padron et al. (2005) J. Virol. 79: 5047-58), AAV5 (Walters et al. (2004) J. Virol. 78: 3361-71) and CPV (Xie et al. (1996) *J. Mol. Biol.* 6:497-520 and Tsao et al. (1991) *Science* 251: 1456-64).

The term "tropism" as used herein refers to preferential or selective entry of the virus into certain cells or tissues, optionally followed by expression (e.g., transcription and, optionally, translation) of a sequence(s) carried by the viral genome in the cell, e.g., for a recombinant virus, expression of a heterologous nucleotide sequence of interest. Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus, from a non-integrated episome, as well as any other form in which the virus may take within the cell.

As used here, "systemic tropism" and "systemic transduction" (and equivalent terms) indicate that the virus capsid or virus vector of the invention exhibits tropism for or transduces, respectively, tissues throughout the body (e.g., brain, lung, skeletal muscle, heart, liver, kidney and/or pancreas). In embodiments of the invention, systemic transduction of muscle tissues (e.g., skeletal muscle, diaphragm and cardiac muscle) is observed. In other embodiments, systemic transduction of skeletal muscle tissues achieved. For example, in particular embodiments, essentially all skeletal muscles throughout the body are transduced (although the efficiency of transduction may vary by muscle type). In particular embodiments, systemic transduction of limb muscles, cardiac muscle and diaphragm muscle is achieved. Optionally, the virus capsid or virus vector is administered via a systemic route (e.g., systemic route such as intravenously, intra-articularly or intra-lymphatically). Alternatively, in other embodiments, the capsid or virus vector is delivered locally (e.g., to the footpad, intramuscularly, intradermally, subcutaneously, topically).

Unless indicated otherwise, "efficient transduction" or "efficient tropism," or similar terms, can be determined by reference to a suitable control (e.g., at least about 25%, 50%, 60%, 70%, 80%, 85%, 90%, 95%, 100%, 125%, 150%, 200%, 250%, 300%, 350%, 400%, 500% or more of the transduction or tropism, respectively, of the control). In particular embodiments, the virus vector efficiently transduces or has efficient tropism for skeletal muscle, cardiac muscle, diaphragm muscle, pancreas (including (β-islet cells), spleen, the gastrointestinal tract (e.g., epithelium and/or smooth muscle), cells of the central nervous system, lung, joint cells, and/or kidney. Suitable controls will depend on a variety of factors including the desired tropism profile. For example, AAV8 and AAV9 are highly efficient in transducing skeletal muscle, cardiac muscle and diaphragm muscle, but have the disadvantage of also transducing liver with high efficiency. Thus, the invention can be practiced to identify viral vectors of the invention that demonstrate the efficient transduction of skeletal, cardiac and/or diaphragm muscle of AAV8 or AAV9, but with a much lower transduction efficiency for liver. Further, because the tropism profile of interest may reflect tropism toward multiple target tissues, it will be appreciated that a suitable vector may represent some tradeoffs. To illustrate, a virus vector of the invention may be less efficient than native AAV8 or AAV9 in transducing skeletal muscle, cardiac muscle and/or diaphragm muscle, but because of low level transduction of liver, may nonetheless be very desirable.

Similarly, it can be determined if a virus "does not efficiently transduce" or "does not have efficient tropism" for a target tissue, or similar terms, by reference to a suitable control. In particular embodiments, the virus vector does not efficiently transduce (i.e., has does not have efficient tropism) for liver, kidney, gonads and/or germ cells. In particular embodiments, undesirable transduction of tissue(s) (e.g., liver) is 20% or less, 10% or less, 5% or less, 1% or less, 0.1% or less of the level of transduction of the desired target tissue(s) (e.g., skeletal muscle, diaphragm muscle, cardiac muscle and/or cells of the central nervous system) as compared with a suitable control.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), but in representative embodiments are either single or double stranded DNA sequences.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide. In representative embodiments an "isolated" nucleotide is enriched by at least about 10-fold, 100-fold, 1000-fold, 10,000-fold or more as compared with the starting material.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In representative embodiments an "isolated" polypeptide is enriched by at least about 10-fold, 100-fold, 1000-fold, 10,000-fold or more as compared with the starting material.

As used herein, by "isolate" or "purify" (or grammatical equivalents) a virus vector, it is meant that the virus vector is at least partially separated from at least some of the other components in the starting material. In representative embodiments an "isolated" or "purified" virus vector is enriched by at least about 10-fold, 100-fold, 1000-fold, 10,000-fold or more as compared with the starting material.

A "therapeutic polypeptide" is a polypeptide that can alleviate, reduce, prevent, delay and/or stabilize symptoms that result from an absence or defect in a protein in a cell or subject and/or is a polypeptide that otherwise confers a benefit to a subject, e.g., anti-cancer effects or improvement in transplant survivability.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" or "effective" amount as used herein is an amount that is sufficient to provide some improvement or benefit to the subject. Alternatively stated, a "treatment effective" or "effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. Generally, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

A "rAAV vector genome" or "rAAV genome" is an AAV genome (i.e., vDNA) that comprises one or more heterologous nucleic acid sequences. rAAV vectors generally require only the terminal repeat(s) (TR(s)) in cis to generate virus. All other viral sequences are dispensable and may be supplied in trans (Muzyczka (1992) Curr. Topics Microbiol. Immunol. 158:97). Typically, the rAAV vector genome will only retain the one or more TR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In some embodiments of the invention, the rAAV vector genome comprises at least one TR sequence (e.g., AAV TR sequence), optionally two TRs (e.g., two AAV TRs), which typically will be at the 5' and 3' ends of the vector genome and flank the heterologous nucleic acid, but need not be contiguous thereto. The TRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or any other suitable virus sequence (e.g., the SV40 hairpin that serves as the origin of SV40 replication) can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10, 11, Clade F, or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The virus vectors of the invention can further be "targeted" virus vectors (e.g., having a directed tropism) and/or a "hybrid" parvovirus (i.e., in which the viral TRs and viral capsid are from different parvoviruses) as described in international patent publication WO 00/28004 and Chao et al., (2000) *Molecular Therapy* 2:619.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention.

Further, the viral capsid or genomic elements can contain other modifications, including insertions, deletions and/or substitutions.

As used herein, the term "amino acid" encompasses any naturally occurring amino acid, modified forms thereof, and synthetic amino acids.

Naturally occurring, levorotatory (L-) amino acids are shown in Table 2). Alternatively, the amino acid can be a modified amino acid residue (nonlimiting examples are shown in Table 3) and/or can be an amino acid that is modified by post-translation modification (e.g., acetylation, amidation, formylation, hydroxylation, methylation, phosphorylation or sulfatation).

Further, the non-naturally occurring amino acid can be an "unnatural" amino acid as described, e.g., by Wang et al. *Annu Rev Biophys Biomol Struct.* 35:225-49 (2006)). These unnatural amino acids can advantageously be used to chemically link molecules of interest to the AAV capsid protein.

Modified AAV Capsid Proteins and Virus Capsids and Virus Vectors Comprising the Same.

The present invention is based on the unexpected discovery that modifications in the capsid protein of an MV (e.g., AAV9 or Clade F AAV) can confer one or more desirable properties to virus vectors comprising the modified AAV capsid protein including without limitation, reduced transduction of liver. Thus, the present invention addresses some of the limitations associated with conventional AAV vectors. For example, vectors based on AAV8 and rAAV9 vectors are attractive for systemic nucleic acid delivery because they readily cross the endothelial cell barrier; however, systemic administration of rAAV8 or rAAV9 results in most of the vector being delivered to the liver, thereby reducing transduction of other important target tissues such as skeletal muscle.

Thus, in some embodiments, the present invention provides an adeno-associated virus serotype 9 (AAV9) or Clade F AAV (Table 1) capsid protein, wherein the capsid protein comprises a mutation in one or more amino acids in amino acid regions 498-504, 590-595 and/or 582-587, inclusive (according to AAV9 VP1 numbering), wherein the mutation(s) result in a phenotype of decreased liver transduction and/or reduced glycan binding affinity as compared to a suitable control (e.g., an AAV9 or Clade F VP1 capsid protein lacking said mutation(s), which can be but is not limited to a wild type VP1 capsid protein).

As used herein, a "mutation" or "modification" in an amino acid sequence includes substitutions, insertions and/or deletions, each of which can involve one, two, three, four, five, six, seven, eight, nine, ten or more amino acids. In particular embodiments, the modification is a substitution. For example, in some embodiments, 1, 2, 3, 4, 5, 6, 7, 8, 9, 10, 11, 12, 13, 14, 15, 16, 17, 18, 19, 20, 21, 22, 23, 24, 25 or more amino acids from the equivalent region from one AAV can be substituted into amino acid positions of the native AAV9 or Clade F AAV capsid protein or the corresponding positions of the capsid protein from another AAV, as would be known to one of ordinary skill in the art. However, the modified virus capsids of the invention are not limited to AAV capsids in which amino acids from one AAV capsid are substituted into another AAV capsid, and the substituted and/or inserted amino acids can be from any source, and can further be naturally occurring or partially or completely synthetic.

It will be understood by those skilled in the art that the modified capsid proteins, virus capsids and virus vectors of the invention exclude those capsid proteins, capsids and virus vectors that have the indicated amino acids at the specified positions in their native state (i.e., are not mutants).

As described herein, the nucleic acid and amino acid sequences of the capsid proteins from a number of AAV are known in the art. Thus, the amino acids "corresponding" to amino acid positions 498-504, 590-595 and/or 582-587 (inclusive) of the native AAV9 or a Clade F AAV capsid protein can be readily determined for any other AAV (e.g., by using sequence alignments).

The invention contemplates that the modified capsid proteins of the invention can be produced by modifying the capsid protein of any AAV now known or later discovered. Further, the AAV capsid protein that is to be modified can be a naturally occurring AAV capsid protein (e.g., an AAV2, AAV3a or 3b, AAV4, AAV5, AAV8, AAV9, AAV10 or AAV11 capsid protein or any of the AAV shown in Table 1) but is not so limited. Those skilled in the art will understand that a variety of manipulations to the AAV capsid proteins are known in the art and the invention is not limited to modifications of naturally occurring AAV capsid proteins. For example, the capsid protein to be modified may already have alterations as compared with naturally occurring AAV (e.g., is derived from a naturally occurring AAV capsid protein, e.g., AAV2, AAV3a, AAV3b, AAV4, AAV5, AAV6, AAV7, AAV8, AAV9, AAV10 and/or AAV11 or any other AAV now known or later discovered). Such AAV capsid proteins are also within the scope of the present invention.

In certain embodiments, the present invention provides an AAV9 or Clade F AAV capsid protein comprising, consisting essentially of, or consisting of a mutation at W595, a mutation at Q592, a mutation at W503, a mutation at N498, a mutation at E500 (according to AAV9 VP1 numbering) and any combination thereof, wherein the mutation results in a phenotype of decreased liver transduction and/or reduced glycan binding affinity as compared to a control. The present invention further provides an AAV9 or Clade F AAV capsid protein comprising, consisting essentially of, or consisting of a mutation at N498, S499, E500, F501, A502, W503, P504, T582, N583, H584, Q585, S586, A587, Q590, A591, Q592, T593, G594, W595, singly or in any combination. The mutation at N498, S499, E500, F501, A502, W503, P504, T582, N583, H584, Q585, S586, A587, Q590, A591, Q592, T593, G594, W595 can be a substitution with any other amino acid. As used herein, the term "amino acid" encompasses any naturally occurring amino acid, modified forms thereof, and synthetic amino acids.

Naturally occurring, levorotatory (L-) amino acids are shown in Table 2). Alternatively, the amino acid can be a modified amino acid residue (nonlimiting examples are shown in Table 3) and/or can be an amino acid that is modified by post-translation modification (e.g., acetylation, amidation, formylation, hydroxylation, methylation, phosphorylation or sulfatation).

Further, the non-naturally occurring amino acid can be an "unnatural" amino acid as described, e.g., by Wang et al. *Annu Rev Biophys Biomol Struct.* 35:225-49 (2006)).

In particular embodiments, the capsid protein can comprise, consist essentially of or consist of a W595C mutation, a Q592L mutation, a W503R mutation, a N498Y mutation, a E500D mutation and any combination thereof, wherein the mutation results in a phenotype of decreased liver transduction and/or reduced glycan binding affinity as compared to a control. It is to be understood that these particular mutations are exemplary and that the amino acids at these positions can be substituted with any other amino acid, e.g., as set forth in Tables 2 and 3, wherein the resulting capsid protein has a phenotype of decreased liver transduction and/or reduced glycan binding affinity as compared to control.

In further embodiments, the present invention provides an AAV9 or Clade F AAV capsid protein comprising, consisting essentially of, or consisting of a W595C mutation (AAV9 VP1 numbering), wherein the mutation results in a phenotype of decreased liver transduction and/or reduced glycan binding affinity as compared to a control.

Also provided herein is an AAV9 or Clade F AAV capsid protein comprising a Q592L mutation (AAV9 VP1 numbering), wherein the mutation results in a phenotype of decreased liver transduction and/or reduced glycan binding affinity as compared to a control.

The present invention further provides an AAV9 or Clade F AAV capsid protein comprising, consisting essentially of, or consisting of a W503R mutation (AAV9 VP1 numbering), wherein the mutation results in a phenotype of decreased liver transduction and/or reduced glycan binding affinity as compared to a control.

In further embodiments, the present invention provides an AAV9 or Clade F AAV capsid protein comprising, consisting essentially of, of consisting of a N498Y mutation (AAV9 VP1 numbering), wherein the mutation results in a phenotype of decreased liver transduction and/or reduced glycan binding affinity as compared to a control. In some embodiments, this AAV9 or Clade F AAV capsid protein can further comprise, consist essentially of, or consist of a L602F mutation (AAV9 VP1 numbering).

Additionally provided herein is an AAV9 or Clade F AAV capsid protein comprising, consisting essentially of, or consisting of a N498I mutation (AAV9 VP1 numbering), wherein the mutation results in a phenotype of decreased liver transduction and/or reduced glycan binding affinity as compared to control.

Further embodiments of this invention include an AAV9 or Clade F AAV capsid protein comprising, consisting essentially of, or consisting of a P468T mutation (AAV9 VP1 numbering), wherein the mutation results in a phenotype of decreased liver transduction and/or reduced glycan binding affinity as compared to control. This AAV9 or Clade F capsid protein can further comprise, consist essentially of, or consist of a E500D mutation (AAV9 VP1 numbering).

In some embodiments, certain mutated AAV9 or Clade F AAV capsid proteins described herein can be employed in virus vectors for direct delivery of a heterologous nucleotide sequence of interest to the central nervous system (CNS). Particular examples of these mutated capsid proteins include variants 9.24, 9.45 and 9.47 as defined in Table 5 herein. Studies with these mutants have demonstrated that virus particles with these mutations are as infectious as parent or control particles (i.e., particles lacking these mutations) when injected directly into the brain. However the parent particles leak out of the brain and can be delivered to the liver. In contrast, particles comprising mutated capsid proteins that are the variants 9.24, 9.45 or 9.47 as described herein are not delivered to the liver in the same manner that parent particles are. It is to be understood that mutations at equivalent amino acid residues in other AAV serotypes are included within this invention to produce capsid proteins that can be employed in the virus vectors of this invention. For example, Table 8 shows mutations in the capsid protein of AAV variants 9.24, 9.45 and 9.47, with the corresponding amino acid residue in other AAV serotypes identified that could be mutated to produce a capsid protein according to the present invention (e.g., having a phenotype of decreased liver transduction and/or reduced glycan binding affinity relative to control). It would be well understood to one of ordinary skill in the art that the present invention includes these mutated capsid proteins of serotypes other than AAV9 or Clade F AAV having the desired phenotype and it would be well within the skill of such an artisan to produce, test and employ such mutants of other AAV serotypes according to the teachings provided herein and as are known in the art.

As noted in the particular embodiments described above, the mutations described can be in an AAV9 or Clade F AAV capsid protein. It would be well known to one of skill in the art what the equivalent amino acids are in other AAV serotypes and the present invention encompasses such other AAV serotypes, comprising, consisting essentially of, or consisting of the mutation(s) of this invention at such equivalent amino acid positions, wherein said mutation(s) result in a phenotype of reduced liver transduction and/or reduced glycan binding affinity as compared to a control.

In some embodiments of this invention, the AAV capsid protein to be mutated or modified can be an AAV with an altered HI loop as described in PCT Publication No. WO 2009/108274 and/or can be an AAV that is modified to contain a poly-His sequence to facilitate purification. As another illustrative example, the AAV capsid protein of this invention can have a peptide targeting sequence incorporated therein as an insertion or substitution. Further, the AAV capsid protein can comprise a large domain from another AAV that has been substituted and/or inserted into the capsid protein.

Thus, in particular embodiments, the AAV capsid protein to be modified can be derived from a naturally occurring AAV but further comprise one or more foreign sequences (e.g., that are exogenous to the native virus) that are inserted and/or substituted into the capsid protein and/or has been altered by deletion of one or more amino acids.

Accordingly, when referring herein to a specific AAV capsid protein (e.g., an AAV2, AAV3, AAV4, AAV5, AAV6, AAV7, AAV8, AAV9, AAV10 or AAV11 capsid protein or a capsid protein from any of the AAV shown in Table 1, etc.), it is intended to encompass the native capsid protein as well as capsid proteins that have alterations other than the modifications of the invention. Such alterations include substitutions, insertions and/or deletions. In particular embodiments, the capsid protein comprises 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acids inserted therein (other than the insertions of the present invention) as compared with the native AAV capsid protein sequence. In embodiments of the invention, the capsid protein comprises 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acid substitutions (other than the amino acid substitutions according to the present invention) as compared with the native AAV capsid protein sequence. In embodiments of the invention, the capsid protein comprises a deletion of 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acids (other than the amino acid deletions of the invention) as compared with the native AAV capsid protein sequence.

Thus, for example, the term "AAV9 capsid protein" includes AAV capsid proteins having the native AAV9 capsid protein sequence (see, e.g., GenBank® Database Accession Nos. AY530579 (Hu14); AY530596 (Hu31); AY530597 (Hu32)), as well as those comprising substitutions, insertions and/or deletions (as described in the preceding paragraph) in the native AAV9 or Hu.31 or Hu.32 capsid protein sequence.

The term "Clade F AAV capsid protein" includes AAV capsid proteins having the native capsid protein sequence of a Clade F AAV, for example, as shown in Table 1 (see GenBank® Database Accession No. AY530579, as well as those comprising substitutions, insertions and/or deletions (as described in the preceding paragraph) in the native AAV9 capsid protein sequence.

In particular embodiments, the AAV capsid protein has the native AAV capsid protein sequence or has an amino acid sequence that is at least about 90%, 95%, 97%, 98% or 99% similar or identical to a native AAV capsid protein sequence. For example, in particular embodiments, an "AAV9" capsid protein encompasses the native AAV9 capsid protein sequence as well as sequences that are at least about 90%, 95%, 97%, 98% or 99% similar or identical to the native AAV9 capsid protein sequence. As a further example, in particular embodiments, a "Glade F" capsid protein encompasses the native capsid protein sequence of a Clade F AAV (see Table 1) as well as sequences that are at least about 90%, 95%, 97%, 98% or 99% similar or identical to the native capsid protein sequence of a Clade F AAV.

Methods of determining sequence similarity or identity between two or more amino acid sequences are known in the art. Sequence similarity or identity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), and/or the Best Fit sequence program described by Devereux et al., *Nucl. Acid Res.* 12:387-395 (1984), as well as by inspection.

Another suitable algorithm is the BLAST algorithm, described in Altschul et al., *J. Mol. Biol.* 215:403-410, (1990) and Karlin et al., *Proc. Natl. Acad. Sci. USA* 90:5873-5787 (1993). A particularly useful BLAST program is the WU-BLAST-2 program which was obtained from Altschul et al., *Methods in Enzymology*, 266:460-480 (1996). WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al., (1997) *Nucleic Acids Res.* 25:3389-3402.

In representative embodiments of the invention, a modification is made in the region of amino acid positions 498-504, 590-595 and/or 582-587 (inclusive) of the native AAV9 or Clade F AAV capsid protein (using AAV9 VP1 numbering) or the corresponding positions of other AAV, i.e., at the amino acids corresponding to amino acid positions 498-504, 590-595 and/or 582-587 (AAV9 VP1 numbering) of the native capsid protein of any other AAV serotype. The amino acid positions in other AAV serotypes or modified AAV capsids that "correspond to" positions 498-504, 590-595 and/or 582-587 of the native AAV9 or Clade F AAV capsid protein will be apparent to those skilled in the art and can be readily determined using sequence alignment techniques (see, e.g., FIG. 7 of WO 2006/066066) and/or crystal structure analysis (Padron et al., (2005) *J. Virol.* 79:5047-58).

In further embodiments, the mutation or modification of this invention can be introduced into an AAV capsid protein that already contains insertions and/or deletions such that the position of all downstream sequences is shifted. In this situation, the amino acid positions corresponding to amino acid positions 498-504, 590-595 and/or 582-587 in the AAV9 capsid protein would still be readily identifiable to those skilled in the art.

In embodiments of this invention, transduction of cardiac muscle and/or skeletal muscle (determined on the basis of an individual skeletal muscle, multiple skeletal muscles, or the whole range of skeletal muscles) with the AAV vectors of this invention is at least about one-fold, two-fold, three-fold, four-fold, five-fold, ten-fold, 50-fold, 100-fold, 1000-fold or higher than transduction levels in liver. In some embodiments, transduction of cardiac muscle and/or skeletal muscle (determined on the basis of an individual skeletal muscle, multiple skeletal muscles, or the whole range of skeletal muscles) with the AAV vectors of this invention is at least about 5%, 10%, 15%, 20%, 25%, 30%, 35%, 40%, 45%, 50%, 60%, 70%, 80%, 90%, 100%, 125%, 150%, 175%, 200%, 300%, 400%, 500%, 750%, 1000% or higher than transduction levels in liver.

The invention also provides a virus capsid comprising, consisting essentially of, or consisting of the modified AAV capsid protein of the invention. In particular embodiments, the virus capsid is a parvovirus capsid, which may further be an autonomous parvovirus capsid or a dependovirus capsid. Optionally, the virus capsid is an AAV capsid. In particular embodiments, the AAV capsid is an AAV1, AAV2, AAV3a, AAV3b, AAV4, AAV5, AAV6, AAV7, AAV8, AAV9, AAV10, AAV11 or any other AAV shown in Table 1 or is derived from any of the foregoing by one or more insertions, substitutions and/or deletions.

The modified virus capsids can be used as "capsid vehicles," as has been described, for example, in U.S. Pat. No. 5,863,541. Molecules that can be packaged by the modified virus capsid and transferred into a cell include heterologous DNA, RNA, polypeptides, small organic molecules, metals, or combinations of the same.

Heterologous molecules are defined as those that are not naturally found in an AAV infection, e.g., those not encoded by a wild-type AAV genome. Further, therapeutically useful molecules can be associated with the outside of the chimeric virus capsid for transfer of the molecules into host target cells. Such associated molecules can include DNA, RNA, small organic molecules, metals, carbohydrates, lipids and/or polypeptides. In one embodiment of the invention the therapeutically useful molecule is covalently linked (i.e., conjugated or chemically coupled) to the capsid proteins. Methods of covalently linking molecules are known by those skilled in the art.

The modified virus capsids of the invention also find use in raising antibodies against the novel capsid structures. As a further alternative, an exogenous amino acid sequence may be inserted into the modified virus capsid for antigen presentation to a cell, e.g., for administration to a subject to produce an immune response to the exogenous amino acid sequence.

In other embodiments, the virus capsids can be administered to block certain cellular sites prior to and/or concurrently with (e.g., within minutes or hours of each other) administration of a virus vector delivering a nucleic acid encoding a polypeptide or functional RNA of interest. For example, the inventive capsids can be delivered to block cellular receptors on liver cells and a delivery vector can be administered subsequently or concurrently, which may reduce transduction of liver cells, and enhance transduction of other targets (e.g., skeletal, cardiac and/or diaphragm muscle).

According to representative embodiments, modified virus capsids can be administered to a subject prior to and/or concurrently with a modified virus vector according to the present invention. Further, the invention provides compositions and pharmaceutical formulations comprising the inventive modified virus capsids; optionally, the composition also comprises a modified virus vector of the invention.

The invention also provides nucleic acids (optionally, isolated nucleic acids) encoding the mutated or modified virus capsids and capsid proteins of the invention. Further provided are vectors comprising the nucleic acids, and cells (in vivo or in culture) comprising the nucleic acids and/or vectors of the invention. Suitable vectors include without limitation viral vectors (e.g., adenovirus, AAV, herpesvirus, vaccinia, poxviruses, baculoviruses, and the like), plasmids, phage, YACs, BACs, and the like as are well known in the art. Such nucleic acids, vectors and cells can be used, for example, as reagents (e.g., helper packaging constructs or packaging cells) for the production of modified virus capsids or virus vectors as described herein.

Virus capsids according to the invention can be produced using any method known in the art, e.g., by expression from a baculovirus (Brown et al., (1994) *Virology* 198:477-488).

The modifications to the AAV capsid protein according to the present invention are "selective" modifications. This approach is in contrast to previous work with whole subunit or large domain swaps between AAV serotypes (see, e.g., international patent publication WO 00/28004 and Hauck et al., (2003) *J. Virology* 77:2768-2774). In particular embodiments, a "selective" modification results in the insertion and/or substitution and/or deletion of less than about 50, 40, 30, 20, 18, 15, 12, 10, 9, 8, 7, 6, 5, 4, 3 or 2 contiguous amino acids.

The modified capsid proteins and capsids of the invention can further comprise any other mutation or modification, now known or later identified.

For example, the AAV capsid proteins and virus capsids of the invention can be chimeric in that they can comprise all or a portion of a capsid subunit from another virus, optionally another parvovirus or AAV, e.g., as described in PCT Publication No. WO 00/28004.

The virus capsid can be a targeted virus capsid comprising a targeting sequence (e.g., substituted or inserted in the viral capsid) that directs the virus capsid to interact with cell-surface molecules present on desired target tissue(s) (see, e.g., PCT Publication No. WO 00/28004 and Hauck et al., (2003) *J. Virology* 77:2768-2774); Shi et al., *Human Gene Therapy* 17:353-361 (2006) [describing insertion of the integrin receptor binding motif RGD at positions 520 and/or 584 of the AAV capsid subunit]; and U.S. Pat. No. 7,314,912 [describing insertion of the P1 peptide containing an RGD motif following amino acid positions 447, 534, 573 and 587 of the AAV2 capsid subunit]). Other positions within the AAV capsid subunit that tolerate insertions are known in the art (e.g., positions 449 and 588 described by Grifman et al., *Molecular Therapy* 3:964-975 (2001)).

For example, some of the virus capsids of the invention have relatively inefficient tropism toward most target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the virus capsid a desired tropism and, optionally, selective tropism for particular tissue(s). AAV capsid proteins, capsids and vectors comprising targeting sequences are described, for example in PCT Publication No. WO 00/28004. As another possibility one or more non-naturally occurring amino acids as described by Wang et al., *Annu Rev Biophys Biomol Struct.* 35:225-49 (2006)) can be incorporated into the AAV capsid subunit at an orthogonal site as a means of redirecting a low-transduction vector to a desired target tissue(s). These unnatural amino acids can advantageously be used to chemically link molecules of interest to the AAV capsid protein including without limitation: glycans (mannose—dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like. Methods of chemically modifying amino acids are known in the art (see, e.g., Greg T. Hermanson, *Bioconjugate Techniques*, 1$^{st}$ edition, Academic Press, 1996).

In representative embodiments, the targeting sequence may be a virus capsid sequence (e.g., an autonomous parvovirus capsid sequence, AAV capsid sequence, or any other viral capsid sequence) that directs infection to a particular cell type(s).

As another nonlimiting example, a heparin binding domain (e.g., the respiratory syncytial virus heparin binding domain) may be inserted or substituted into a capsid subunit that does not typically bind HS receptors (e.g., AAV 4, AAV5) to confer heparin binding to the resulting mutant.

B19 infects primary erythroid progenitor cells using globoside as its receptor (Brown et al. (1993) *Science* 262:114). The structure of B19 has been determined to 8 Å resolution (Agbandje-McKenna et al. (1994) *Virology* 203:106). The region of the B19 capsid that binds to globoside has been mapped between amino acids 399-406 (Chapman et al. (1993) *Virology* 194:419), a looped out region between β-barrel structures E and F (Chipman et al. (1996) *Proc. Nat. Acad. Sci. USA* 93:7502). Accordingly, the globoside receptor binding domain of the B19 capsid may be substituted into the AAV capsid protein to target a virus capsid or virus vector comprising the same to erythroid cells.

In representative embodiments, the exogenous targeting sequence may be any amino acid sequence encoding a peptide that alters the tropism of a virus capsid or virus vector comprising the modified AAV capsid protein. In particular embodiments, the targeting peptide or protein may be naturally occurring or alternately, completely or partially synthetic. Exemplary targeting sequences include ligands and other peptides that bind to cell surface receptors and glycoproteins, such as RGD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., α, β or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadoliberin, corticostatin, β-endorphin, leu-enkephalin, rimorphin, α-neo-enkephalin, angiotensin, pneumadin, vasoactive intestinal peptide, neurotensin, motilin, and fragments thereof as described herein. As yet a further alternative, the binding domain from a toxin (e.g., tetanus toxin or snake toxins, such as α-bungarotoxin, and the like) can be substituted into the capsid protein as a targeting sequence. In a yet further representative embodiment, the AAV capsid protein can be modified by substitution of a "nonclassical" import/export signal peptide (e.g., fibroblast growth factor-1 and -2, interleukin 1, HIV-1 Tat protein, herpes virus VP22 protein, and the like) as described by Cleves (*Current Biology* 7:R318 (1997)) into the AAV capsid protein.

Phage display techniques, as well as other techniques known in the art, may be used to identify peptides that recognize any cell type of interest.

The targeting sequence may encode any peptide that targets to a cell surface binding site, including receptors (e.g., protein, carbohydrate, glycoprotein or proteoglycan). Examples of cell surface binding sites include, but are not limited to, heparan sulfate, chondroitin sulfate, and other glycosaminoglycans, sialic acid moieties found on mucins, glycoproteins, and gangliosides, MHC I glycoproteins, carbohydrate components found on membrane glycoproteins, including mannose, N-acetyl-galactosamine, N-acetyl-glucosamine, fucose, galactose, and the like.

In particular embodiments, a heparan sulfate (HS) or heparin binding domain is substituted into the virus capsid (for example, in an AAV that otherwise does not bind to HS or heparin). It is known in the art that HS/heparin binding is mediated by a "basic patch" that is rich in arginines and/or lysines. An exemplary embodiment is a sequence following the motif BXXB, where "B" is a basic residue and X is neutral and/or hydrophobic. As one nonlimiting example, BXXB is RGNR. In particular embodiments, BXXB is substituted for amino acid positions 262 through 265 in the native AAV2 capsid protein or the corresponding position in the capsid protein of another AAV.

Other nonlimiting examples of suitable targeting sequences include the peptides targeting coronary artery endothelial cells identified by MUller et al. *Nature Biotechnology* 21:1040-1046 (2003) (consensus sequences NSVRDLLG/S) (SEQ ID NO:2), PRSVTVP (SEQ ID NO:3), NSVSSX(S/A) (SEQ ID NO:4)); tumor-targeting peptides as described by Grifman et al. *Molecular Therapy* 3:964-975 (2001) (e.g., NGR, NGRAHA (SEQ ID NO:5)); lung or brain targeting sequences as described by Work et al. *Molecular Therapy* 13:683-693 (2006) (QPEHSST (SEQ ID NO:6), VNTANST (SEQ ID NO:7), HGPMQKS (SEQ ID NO:8), PHKPPLA (SEQ ID NO:9), IKNNEMW (SEQ ID NO:10), RNLDTPM (SEQ ID NO:11), VDSHRQS (SEQ ID NO:12), YDSKTKT (SEQ ID NO:13), SQLPHQK (SEQ ID NO:14), STMQQNT (SEQ ID NO:15), TERYMTQ (SEQ ID NO:16), QPEHSST (SEQ ID NO:17), DASLSTS (SEQ ID NO:18), DLPNKKT (SEQ ID NO:19), DLTAARL (SEQ ID NO:20), EPHQFNY (SEQ ID NO:21), EPQSNHT (SEQ ID NO:22), MSSWPSQ (SEQ ID NO:23), NPKHNAT (SEQ ID NO:24), PDGMRTT (SEQ ID NO:25), PNNNKTT (SEQ ID NO:26), QSTTHDS (SEQ ID NO:27), TGSKQKQ (SEQ ID NO:28), SLKHQAL (SEQ ID NO:29) and SPIDGEQ (SEQ ID NO:30)); vascular targeting sequences described by Hajitou et al., *TCM* 16:80-88 (2006) (WIFPWIQL (SEQ ID NO:31), CDCRGDCFC (SEQ ID NO:32), CNGRC (SEQ ID NO:33), CPRECES (SEQ ID NO:34), GSL, CTTHWGFTLC (SEQ ID NO:35), CGRRAGGSC (SEQ ID NO:36), CKGRAKDC (SEQ ID NO:37) and CVPELGHEC (SEQ ID NO:38)); targeting peptides as described by Koivunen et al. *J. Nucl. Med.* 40:883-888 (1999) (CRRETAWAK (SEQ ID NO:39), KGD, VSWFSHRYSPFAVS (SEQ ID NO:40), GYRDGYAGPILYN (SEQ ID NO:41), XXXY*XXX [where Y* is phospho-Tyr] (SEQ ID NO:42), Y*(E/M)NW (SEQ ID NO:43), RPLPPLP (SEQ ID NO:44), APPLPPR (SEQ ID NO:45), DVFYPYPYASGS (SEQ ID NO:46), MYWYPY (SEQ ID NO:47), DITWDQLWDLMK (SEQ ID NO:48), CWDDG/LWLC (SEQ ID NO:49), EWCEYLGGYLRCYA (SEQ ID NO:50), YXCXXGPXTWXCXP (SEQ ID NO:51), IEGPTLRQWLAARA (SEQ ID NO:52), LWXX (Y/W/F/H) (SEQ ID NO:53), XFXXYLW (SEQ ID NO:54), SSIISHFRWGLCD (SEQ ID NO:55), MSRPACPPNDKYE (SEQ ID NO:56), CLRSGRGC (SEQ ID NO:57), CHWMFSPWC (SEQ ID NO:58), WXXF (SEQ ID NO:59), CSSRLDAC (SEQ ID NO:60), CLPVASC (SEQ ID NO:61), CGFECVRQCPERC (SEQ ID NO:62), CVALCREACGEGC (SEQ ID NO:63), SWCEPGWCR (SEQ ID NO:64), YSGKWGW (SEQ ID NO:65), GLSGGRS (SEQ ID NO:66), LMLPRAD (SEQ ID NO:67), CSCFRDVCC (SEQ ID NO:68), CRDWSVIC (SEQ ID NO:69), CNGRC (SEQ ID NO:70) and GSL); and tumor targeting peptides as described by Newton & Deutscher, "Phage Peptide Display" in Handbook of Experimental Pharmacology, pages 145-163, Springer-Verlag, Berlin (2008) (MARSGL (SEQ ID NO:71), MARAKE (SEQ ID NO:72), MSRTMS (SEQ ID NO:73), KCCYSL (SEQ ID NO:74), WRR, WKR, WVR, WVK, WIK, WTR, WVL, WLL, WRT, WRG, WVS, WVA, MYWGDSHWLQYWYE (SEQ ID NO:75), MQLPLAT (SEQ ID NO:76), EWLS (SEQ ID NO:77), SNEW (SEQ ID NO:78), TNYL (SEQ ID NO:79), WIFPWIQL (SEQ ID NO:80), WDLAWMFRLPVG (SEQ ID NO:81), CTVALPGGYVRVC (SEQ ID NO:82), CVPELGHEC (SEQ ID NO:83), CGRRAGGSC (SEQ ID NO:84), CVAYCIEHHCWTC (SEQ ID NO:85), CVFAHNYDYLVC (SEQ ID NO:86), and CVFTSNYAFC (SEQ ID NO:87), VHSPNKK (SEQ ID NO:88), CDCRGDCFC (SEQ ID NO:89), CRGDGWC (SEQ ID NO:90), XRGCDX (SEQ ID NO:91), PXX(S/T) (SEQ ID NO:92), CTTHWGFTLC (SEQ ID NO:93), SGKGPRQITAL (SEQ ID NO:94), A(A/Q)(N/A)(L/Y)(TN/M/R)(R/K) (SEQ ID NO:95), VYMSPF (SEQ ID NO:96), MQLPLAT (SEQ ID NO:97), ATWLPPR (SEQ ID NO:98), HTMYYHHYQHHL (SEQ ID NO:99), SEVGCRAGPLQWLCEKYFG (SEQ ID NO:100), CGLLPVGRPDRNVWRWLC (SEQ ID NO:101), CKGQCDRFKGLPWEC (SEQ ID NO:102), SGRSA (SEQ ID NO:103), WGFP (SEQ ID NO:104), LWXXAr [Ar=Y, W, F, H] (SEQ ID NO:53), XFXXYLW (SEQ ID NO:105), AEPMPHSLNFSQYLWYT (SEQ ID NO:106), WAY(W/F)SP (SEQ ID NO:107), IELLQAR (SEQ ID NO:108), DITWDQLWDLMK (SEQ ID NO:109), AYTKCSRQWRTCMTTH (SEQ ID NO:110), PQNSKIPGPTFLDPH (SEQ ID NO:111), SMEPALPDWWWKMFK (SEQ ID NO:112), ANTPCGPYTHDCPVKR (SEQ ID NO:113), TACHQHVRMVRP (SEQ ID NO:114), VPWMEPAYQRFL (SEQ ID NO:115), DPRATPGS (SEQ ID NO:116), FRPNRAQDYNTN (SEQ ID NO:117), CTKNSYLMC (SEQ ID NO:118), C(R/Q)(L/R)T(G/N)XXG(AN)GC (SEQ ID NO:119), CPIEDRPMC (SEQ ID NO:120), HEWSYLAPYPWF (SEQ ID NO:121), MCPKHPLGC (SEQ ID NO:122), RMWPSSTVNLSAGRR (SEQ ID NO:123), SAKTAVSQRVWLPSHRGGEP (SEQ ID NO:124), KSREHVNNSACPSKRITAAL (SEQ ID NO:125), EGFR (SEQ ID NO:126), RVS, AGS, AGLGVR (SEQ ID NO:127), GGR, GGL, GSV, GVS, GTRQGHTMRLGVSDG (SEQ ID NO:128), IAGLATPGWSHWLAL (SEQ ID NO:129), SMSIARL (SEQ ID NO:130), HTFEPGV (SEQ ID NO:131), NTSLKRISNKRIRRK (SEQ ID NO:132), LRIKRKRRKRKKTRK (SEQ ID NO:133), GGG, GFS, LWS, EGG, LLV, LSP, LBS, AGG, GRR, GGH and GTV).

As yet a further alternative, the targeting sequence may be a peptide that can be used for chemical coupling (e.g., can comprise arginine and/or lysine residues that can be chemically coupled through their R groups) to another molecule that targets entry into a cell.

As another option, the AAV capsid protein or virus capsid of the invention can comprise a mutation as described in WO 2006/066066. For example, the capsid protein can comprise a selective amino acid substitution at amino acid position 263, 705, 708 and/or 716 of the native AAV2 capsid protein or a corresponding change(s) in a capsid protein from another AAV. Additionally, or alternatively, in representative embodiments, the capsid protein, virus capsid or vector comprises a selective amino acid insertion directly following amino acid position 264 of the AAV2 capsid protein or a corresponding change in the capsid protein from other AAV. By "directly following amino acid position X" it is intended that the insertion immediately follows the indicated amino acid position (for example, "following amino acid position 264" indicates a point insertion at position 265 or a larger insertion, e.g., from positions 265 to 268, etc.).

The foregoing embodiments of the invention can be used to deliver a heterologous nucleic acid to a cell or subject as described herein. For example, the modified vector can be used to treat a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase) as described herein.

Those skilled in the art will appreciate that for some AAV capsid proteins the corresponding modification will be an insertion and/or a substitution, depending on whether the corresponding amino acid positions are partially or completely present in the virus or, alternatively, are completely absent. Likewise, when modifying AAV other than AAV9, the specific amino acid position(s) may be different than the position in AAV9 (see, e.g., Tables 4 and 8). As discussed elsewhere herein, the corresponding amino acid position(s) will be readily apparent to those skilled in the art using well-known techniques.

In other representative embodiments, the modified capsid proteins or virus capsids of the invention further comprise one or more mutations as described in WO 2007/089632 (e.g., an E→K mutation at amino acid position 531 of the AAV9 capsid protein or the corresponding position of the capsid protein from another AAV).

In further embodiments, the modified capsid protein or capsid can comprise a mutation as described in PCT Publication No. WO 2009/108274.

As another embodiment, the AAV capsid protein of this invention can comprise a mutation as described by Zhong et al. (*Virology* 381:194-202 (2008); *Proc. Nat. Acad. Sci.* 105:

7827-32 (2008)). For example, the AAV capsid protein can comprise a Y→F mutation at amino acid position 730.

The modifications described above can be incorporated into the capsid proteins or capsids of the invention in combination with each other and/or with any other modification now known or later discovered.

The invention also encompasses virus vectors comprising the modified capsid proteins and capsids of the invention. In particular embodiments, the virus vector is a parvovirus vector (e.g., comprising a parvovirus capsid and/or vector genome), for example, an AAV vector (e.g., comprising an AAV capsid and/or vector genome). In representative embodiments, the virus vector comprises a modified AAV capsid comprising a modified capsid subunit of the invention and a vector genome.

For example, in representative embodiments, the virus vector comprises: (a) a modified virus capsid (e.g., a modified AAV capsid) comprising a modified capsid protein of the invention; and (b) a nucleic acid comprising a terminal repeat sequence (e.g., an AAV TR), wherein the nucleic acid comprising the terminal repeat sequence is encapsidated by the modified virus capsid. The nucleic acid can optionally comprise two terminal repeats (e.g., two AAV TRs).

In representative embodiments, the virus vector is a recombinant virus vector comprising a heterologous nucleic acid encoding a polypeptide or functional RNA of interest. Recombinant virus vectors are described in more detail below.

In particular embodiments, the virus vectors of the invention have reduced transduction of liver as compared with the level of transduction by a virus vector without the modified capsid protein. In particular embodiments, the virus vector has systemic transduction toward muscle, e.g., the vector transduces multiple skeletal muscle groups throughout the body and optionally transduces cardiac muscle and/or diaphragm muscle.

It will be understood by those skilled in the art that the modified capsid proteins, virus capsids and virus vectors of the invention exclude those capsid proteins, capsids and virus vectors that have the indicated amino acids at the specified positions in their native state (i.e., are not mutants).

Methods of Producing Virus Vectors.

The present invention further provides methods of producing the inventive virus vectors. In one representative embodiment, the present invention provides a method of producing a virus vector, the method comprising providing to a cell: (a) a nucleic acid template comprising at least one TR sequence (e.g., AAV TR sequence), and (b) AAV sequences sufficient for replication of the nucleic acid template and encapsidation into AAV capsids (e.g., AAV rep sequences and AAV cap sequences encoding the AAV capsids of the invention). Optionally, the nucleic acid template further comprises at least one heterologous nucleic acid sequence. In particular embodiments, the nucleic acid template comprises two AAV ITR sequences, which are located 5' and 3' to the heterologous nucleic acid sequence (if present), although they need not be directly contiguous thereto.

The nucleic acid template and AAV rep and cap sequences are provided under conditions such that virus vector comprising the nucleic acid template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell. As another option, the cell can be a trans-complementing packaging cell line that provides functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski (1992) *Curr. Top. MicrobioL Immun.* 158:67).

As a further alternative, the rep/cap sequences may be stably incorporated into a cell.

Typically the AAV rep/cap sequences will not be flanked by the TRs, to prevent rescue and/or packaging of these sequences.

The nucleic acid template can be provided to the cell using any method known in the art. For example, the template can be supplied by a non-viral (e.g., plasmid) or viral vector. In particular embodiments, the nucleic acid template is supplied by a herpesvirus or adenovirus vector (e.g., inserted into the E1a or E3 regions of a deleted adenovirus). As another illustration, Palombo et al. (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the nucleic acid template is provided by a replicating rAAV virus. In still other embodiments, an AAV provirus comprising the nucleic acid template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al. (1997) *Nature Med.* 3:1295; and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by TRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector can further comprise the nucleic acid template. The AAV rep/cap sequences and/or the rAAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the rAAV template can be provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The rAAV template can be provided as a separate replicating viral vector. For example, the rAAV template can be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by TRs so that these sequences are not packaged into the AAV virions.

Zhang et al. ((2001) *Gene Ther.* 18:704-12) describes a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al. (1999) *Gene Therapy* 6:986 and PCT Publication No. WO 00/17377.

As a further alternative, the virus vectors of the invention can be produced in insect cells using baculovirus vectors to deliver the rep/cap genes and rAAV template as described, for example, in Urabe et al. (2002) *Human Gene Therapy* 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

Recombinant Virus Vectors.

The virus vectors of the present invention are useful for the delivery of nucleic acids to cells in vitro, ex vivo, and in vivo. In particular, the virus vectors can be advantageously employed to deliver or transfer nucleic acids to animal cells, including e.g., mammalian cells.

Any heterologous nucleic acid sequence(s) of interest may be delivered in the virus vectors of the present invention. Nucleic acids of interest include nucleic acids encoding polypeptides, including therapeutic (e.g., for medical or veterinary uses) or immunogenic (e.g., for vaccines) polypeptides.

Therapeutic polypeptides include, but are not limited to, cystic fibrosis transmembrane regulator protein (CFTR), dystrophin (including mini- and micro-dystrophins, see, e.g., Vincent et al. (1993) *Nature Genetics* 5:130; U.S. Patent Publication No. 2003017131; PCT Publication No. WO/2008/088895, Wang et al. *Proc. Natl. Acad. Sci. USA* 97:13714-13719 (2000); and Gregorevic et al. *Mol. Ther.* 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al. (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $α_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), lysosomal acid α-glucosidase, α-galactosidase A, receptors (e.g., the tumor necrosis growth factorα soluble receptor), S100A1, parvalbumin, adenylyl cyclase type 6, a molecule that modulates calcium handling (e.g., $SERCA_{2A}$, Inhibitor 1 of PP1 and fragments thereof [e.g., PCT Publication Nos. WO 2006/029319 and WO 2007/100465]), a molecule that effects G-protein coupled receptor kinase type 2 knockdown such as a truncated constitutively active bARKct, anti-inflammatory factors such as RAP, anti-myostatin proteins, aspartoacylase, monoclonal antibodies (including single chain monoclonal antibodies; an exemplary Mab being the Herceptin® Mab), neuropeptides and fragments thereof (e.g., galanin, Neuropeptide Y (see U.S. Pat. No. 7,071,172), angiogenesis inhibitors such as Vasohibins and other VEGF inhibitors (e.g., Vasohibin 2 [see PCT Publication WO JP2006/073052]). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. AAV vectors can also be used to deliver monoclonal antibodies and antibody fragments, for example, an antibody or antibody fragment directed against myostatin (see, e.g., Fang et al. *Nature Biotechnology* 23:584-590 (2005)).

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Optionally, the heterologous nucleic acid encodes a secreted polypeptide (e.g., a polypeptide that is a secreted polypeptide in its native state or that has been engineered to be secreted, for example, by operable association with a secretory signal sequence as is known in the art).

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al. (1999) *Nature Biotech.* 17:246; U.S. Pat. No. 6,013,487; U.S. Pat. No. 6,083,702), interfering RNAs (RNAi) including siRNA, shRNA or miRNA that mediate gene silencing (see, Sharp et al. (2000) *Science* 287: 2431), and other non-translated RNAs, such as "guide" RNAs (Gorman et al. (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see e.g., Andino et al. *J. Gene Med.* 10:132-142 (2008) and Li et al. *Acta Pharmacol Sin.* 26:51-55 (2005)); phospholamban inhibitory or dominant-negative molecules such as phospholamban S16E (e.g., to treat cardiovascular disease, see e.g., Hoshijima et al. *Nat. Med.* 8:864-871 (2002)), RNAi to adenosine kinase (e.g., for epilepsy), and RNAi directed against pathogenic organisms and viruses (e.g., hepatitis B and/or C virus, human immunodeficiency virus, CMV, herpes simplex virus, human papilloma virus, etc.).

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn) RNA promoter to induce skipping of this exon. For example, a DNA sequence comprising a U1 or U7 snRNA promoter located 5' to the antisense/inhibitory sequence(s) can be packaged and delivered in a modified capsid of the invention.

The virus vector may also comprise a heterologous nucleic acid that shares homology with and recombines with a locus on a host chromosome. This approach can be utilized, for example, to correct a genetic defect in the host cell.

The present invention also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura et al., (1994) *Proc. Nat. Acad. Sci USA* 91:8507; U.S. Pat. No. 5,916,563 to Young et al., U.S. Pat. No. 5,905,040 to Mazzara et al., U.S. Pat. No. 5,882,652, U.S. Pat. No. 5,863,541 to Samulski et al.). The antigen may be presented in the parvovirus capsid. Alternatively, the antigen may be expressed from a heterologous nucleic acid introduced into a recombinant vector genome. Any immunogen of interest as described herein and/or as is known in the art can be provided by the virus vector of the present invention.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env gene products). The immunogenic polypeptide can also be an arenavirus immunogen (e.g., Lassa fever virus immunogen, such as the Lassa fever virus nucleocapsid protein and/or the Lassa fever envelope glycoprotein), a poxvirus immunogen (e.g., a vaccinia virus immunogen, such as the vaccinia L1 or L8 gene product), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpesvirus immunogen (e.g., CMV, EBV, HSV immunogens) a mumps virus immunogen, a measles virus immunogen, a rubella virus immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (Immunity 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al. (1994) *Proc. Natl. Acad. Sci. USA* 91:3515; Kawakami et al. (1994) *J. Exp. Med.,* 180:347; Kawakami et al. (1994) *Cancer Res.* 54:3124), MART-1, gp100 MAGE-1, MAGE-2, MAGE-3, CEA, TRP-1, TRP-2, P-15, tyrosinase (Brichard et al. (1993) *J. Exp. Med.* 178:489); HER-2/neu gene product (U.S. Pat. No. 4,968,603), CA125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (PCT Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Further, regulated expression of the heterologous nucleic acid(s) of interest can be achieved at the post-transcriptional level, e.g., by regulating selective splicing of different introns by the presence or absence of an oligonucleotide, small molecule and/or other compound that selectively blocks splicing activity at specific sites (e.g., as described in PCT Publication No. WO 2006/119137).

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and/or lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present invention can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping [see e.g., PCT Publication No. WO/2003/095647], antisense against U7 snRNAs to induce exon skipping [see e.g., PCT Publication No. WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic disorders, congenital emphysema (al-antitrypsin), Lesch-Nyhan Syndrome (hypoxanthine guanine phosphoribosyl transferase), Niemann-Pick disease (sphingomyelinase), Tays Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1) and fragments thereof (e.g., I1C), serca2a, zinc finger proteins that regulate the phospholamban gene, Barkct, β2-adrenergic receptor, (32-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

The invention can also be used to produce induced pluripotent stem cells (iPS). For example, a virus vector of the invention can be used to deliver stem cell associated nucleic acid(s) into a non-pluripotent cell, such as adult fibroblasts, skin cells, liver cells, renal cells, adipose cells, cardiac cells, neural cells, epithelial cells, endothelial cells, and the like. Nucleic acids encoding factors associated with stem cells are known in the art. Nonlimiting examples of such factors associated with stem cells and pluripotency include Oct-3/4, the SOX family (e.g., SOX1, SOX2, SOX3 and/or SOX15), the Klf family (e.g., Klf1, Klf2, Klf4 and/or Klf5), the Myc family (e.g., C-myc, L-myc and/or N-myc), NANOG and/or LIN28.

The invention can also be practiced to treat and/or prevent a metabolic disorder such as diabetes (e.g., insulin), hemophilia (e.g., Factor IX or Factor VIII), a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylgl ucosaminidase], C [acetyl-CoA:α-glucosaminide acetyltransferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase).

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present invention permit the treatment and/or prevention of genetic diseases.

The virus vectors according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

In addition, virus vectors according to the instant invention find use in diagnostic and screening methods, whereby a nucleic acid of interest is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present invention may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid can be administered in an immunogenically effective amount, as described herein.

The virus vectors of the present invention can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein. Alternatively, the cancer antigen can be expressed as part of the virus capsid or be otherwise associated with the virus capsid (e.g., as described above).

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector expressing a cancer cell antigen according to the instant invention. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration.

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles, adults and geriatric subjects.

In representative embodiments, the subject is "in need of" the methods of the invention and thus in some embodiments can be a "subject in need thereof.".

In particular embodiments, the present invention provides a pharmaceutical composition comprising a virus vector and/or capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, optionally at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendricytes), lung cells, cells of the eye (including retinal cells, retinal pigment epithelium, and corneal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further embodiment, the cell can be a stem cell (e.g., neural stem cell, liver stem cell). As still a further embodiment, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo nucleic acid delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vector and/or virus capsid to a subject. Administration of the virus vectors and/or capsids according to the present invention to a human subject or an animal in need thereof can be by any means known in the art. Optionally, the virus vector and/or capsid can be delivered in a treatment effective or prevention effective dose in a pharmaceutically acceptable carrier.

The virus vectors and/or capsids of the invention can further be administered to elicit an immunogenic response (e.g., as a vaccine). Typically, immunogenic compositions of the present invention comprise an immunogenically effective amount of virus vector and/or capsid in combination with a pharmaceutically acceptable carrier. Optionally, the dosage is sufficient to produce a protective immune response (as defined above).

Dosages of the virus vector and/or capsid to be administered to a subject depend upon the mode of administration, the disease or condition to be treated and/or prevented, the individual subject's condition, the particular virus vector or capsid, the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^3$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis *brevis*, abductor pollicis longus, adductor *brevis*, adductor hallucis, adductor longus, adductor magnus, adductor pollicis, anconeus, anterior scalene, articularis genus, biceps brachii, biceps femoris, *brachialis*, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis *brevis*, extensor carpi radialis longus, extensor carpi ulnaris, extensor digiti minimi, extensor digitorum, extensor digitorum *brevis*, extensor digitorum longus, extensor hallucis *brevis*, extensor hallucis longus, extensor indicis, extensor pollicis *brevis*, extensor pollicis longus, flexor carpi radialis, flexor carpi ulnaris, flexor digiti minimi *brevis* (in the hand), flexor digiti minimi *brevis* (in the foot), flexor digitorum *brevis*, flexor digitorum longus, flexor digitorum *profundus*, flexor digitorum superficialis, flexor hallucis *brevis*, flexor hallucis longus, flexor pollicis *brevis*, flexor pollicis longus, *frontalis*, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris *brevis*, palmaris longus, pectineus, *pectoralis* major, *pectoralis* minor, peroneus *brevis*, peroneus longus, peroneus tertius, *piriformis*, plantar interossei, plantaris, platysma, popliteus, posterior scalene, pronator quadratus, pronator *teres*, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, *teres* major, *teres* minor, thoracis, thyrohyoid, tibialis anterior, tibialis posterior, trapezius, triceps brachii, vastus *intermedius*, vastus lateralis, vastus *medialis*, zygomaticus major, and zygomaticus minor, and any other suitable skeletal muscle as known in the art.

The virus vector and/or capsid can be delivered to skeletal muscle by intravenous administration, intra-arterial administration, intraperitoneal administration, limb perfusion, (optionally, isolated limb perfusion of a leg and/or arm; see e.g. Arruda et al. (2005) *Blood* 105:3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration). In embodiments of the invention, the virus vectors and/or capsids of the invention can advantageously be administered without employing "hydrodynamic" techniques. Tissue delivery (e.g., to muscle) of vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Delivery to a target tissue can also be achieved by delivering a depot comprising the virus vector and/or capsid. In representative embodiments, a depot comprising the virus vector and/or capsid is implanted into skeletal, cardiac and/or diaphragm muscle tissue or the tissue can be contacted with a film or other matrix comprising the virus vector and/or capsid. Such implantable matrices or substrates are described, e.g., in U.S. Pat. No. 7,201,898.

In particular embodiments, a virus vector and/or virus capsid according to the present invention is administered to skeletal muscle, diaphragm muscle and/or cardiac muscle (e.g., to treat and/or prevent muscular dystrophy, heart disease [for example, PAD or congestive heart failure]).

In representative embodiments, the invention is used to treat and/or prevent disorders of skeletal, cardiac and/or diaphragm muscle.

In a representative embodiment, the invention provides a method of treating and/or preventing muscular dystrophy in a subject in need thereof, the method comprising: administering a treatment or prevention effective amount of a virus vector of the invention to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-α2, α-sarcoglycan, β-sarcoglycan, γ-sarcoglycan, δ-sarcoglycan, IGF-1, an antibody or antibody fragment against myostatin or myostatin propeptide, and/or RNAi against myostatin. In particular embodiments, the virus vector can be administered to skeletal, diaphragm and/or cardiac muscle as described elsewhere herein.

Alternatively, the invention can be practiced to deliver a nucleic acid to skeletal, cardiac or diaphragm muscle, which is used as a platform for production of a polypeptide (e.g., an enzyme) or functional RNA (e.g., RNAi, microRNA, antisense RNA) that normally circulates in the blood or for systemic delivery to other tissues to treat and/or prevent a disorder (e.g., a metabolic disorder, such as diabetes [e.g., insulin], hemophilia [e.g., Factor IX or Factor VIII], a mucopolysaccharide disorder [e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.] or a lysosomal storage disorder such as Gaucher's disease [glucocerebrosidase] or Fabry disease [α-galactosidase A] or a glycogen storage disorder such as Pompe disease [lysosomal acid α glucosidase]). Other suitable proteins for treating and/or preventing metabolic disorders are described herein. The use of muscle as a platform to express a nucleic acid of interest is described in U.S. Patent Publication No. 20020192189.

Thus, as one aspect, the invention further encompasses a method of treating and/or preventing a metabolic disorder in a subject in need thereof, the method comprising: administering a treatment or prevention effective amount of a virus vector of the invention to skeletal muscle of a subject, wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory of the invention, according to this embodiment, administration to the skeletal muscle can result in secretion of the polypeptide into the systemic circulation and delivery to target tissue(s). Methods of delivering virus vectors to skeletal muscle are described in more detail herein.

The invention can also be practiced to produce antisense RNA, RNAi or other functional RNA (e.g., a ribozyme) for systemic delivery.

The invention also provides a method of treating and/or preventing congenital heart failure or PAD in a subject in need thereof, the method comprising administering a treatment or prevention effective amount of a virus vector of the invention to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor I (I-1) and fragments thereof (e.g., I1C), RNAi against phospholamban; a phospholamban inhibitory or dominant-negative molecule such as phospholamban S16E, a zinc finger protein that regulates the phospholamban gene, β2-adrenergic receptor, (32-adrenergic receptor kinase (BARK), PI3 kinase, calsarcan, a β-adrenergic receptor kinase inhibitor (βARKct), inhibitor 1 of protein phosphatase 1 and fragments thereof (e.g., I1C), S100A1, parvalbumin, adenylyl cyclase type 6, a molecule that effects G-protein coupled receptor kinase type 2 knockdown such as a truncated constitutively active bARKct, Pim-1, PGC-1α, SOD-1, SOD-2, EC-SOD, kallikrein, HIF, thymosin-β4, mir-1, mir-133, mir-206, mir-208 and/or mir-26a.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. 20040013645).

The virus vectors and/or virus capsids disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See e.g., U.S. Pat. No. 4,501,729. Aerosols of solid particles comprising the virus vectors and/or capsids may likewise be produced with any solid particulate medicament aerosol generator, by techniques known in the pharmaceutical art.

The virus vectors and virus capsids can be administered to tissues of the central nervous system (CNS) (e.g., brain, eye) and may advantageously result in broader distribution of the virus vector or capsid than would be observed in the absence of the present invention.

In particular embodiments, the delivery vectors of the invention may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive delivery vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence and/or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid sequences (e.g., GenBank Accession No. J00306) and amino acid sequences (e.g., GenBank Accession No. P01166; contains processed active peptides somatostatin-28 and somatostatin-14) of somatostatins are known in the art.

In particular embodiments, the vector can comprise a secretory signal as described, e.g., in U.S. Pat. No. 7,071,172.

In representative embodiments of the invention, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes. cortex, basal ganglia, hippocampus and portaamygdala), limbic system, neocortex, corpus striatum, cerebrum, and/or inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intracerebral, intraventricular, intravenous (e.g., in the presence of a sugar such as mannitol), intranasal, intra-aural, intra-ocular (e.g., intravitreous, sub-retinal, anterior chamber) and peri-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye may be by topical application of liquid droplets. As a further alternative, the virus vector and/or capsid may be administered as a solid, slow-release formulation (see, e.g., U.S. Pat. No. 7,201,898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

Having described the present invention, the same will be explained in greater detail in the following examples, which are included herein for illustration purposes only and are not intended to be limiting to the invention.

EXAMPLES

Example 1

Engineering Liver-Detargeted AAV9 Vectors for Cardiac and Musculoskeletal Gene Transfer Aspects of the present invention are directed to the development of a new class of AAV9-derived vectors displaying selective loss of liver tropism and demonstrating potential for cardiac and musculoskeletal gene transfer applications. Random mutagenesis of residues within a surface-exposed region of the major AAV9 capsid protein yielded a capsid library with mutations clustered at the icosahedral three-fold symmetry axes. Using a combination of sequence analysis, structural models, and in vivo screening, several functionally diverse AAV9 variants were identified. The latter were classified into three functional subgroups, with respect to parental AAV9 displaying: (I) decreased transduction efficiency across multiple tissues; (II) a selective decrease in liver transduction, or (III) a similar transduction profile. Notably, variants 9.45 and 9.61 (subgroup II) displayed 10 to 25-fold lower gene transfer efficiency in liver, while transducing cardiac and skeletal muscle as efficiently as AAV9. These results were further corroborated by quantitation of vector genome copies and histological analysis of reporter (tdTomato) gene expression. The study highlights the feasibility of generating AAV vectors with selectively ablated tissue tropism, which when combined with other targeting strategies could allow sharply segregated gene expression.

Generation of AAV9 Capsid Library.

The AAV9 helper plasmid, pXR9, containing AAV2 Rep and AAV9 Cap genes was obtained from the UNC Vector Core. A random plasmid library was generated by subjecting the capsid region encoding amino acids 390 to 627 (VP1 numbering; Genbank® Database Accession No. AY530579.1) [43] to error-prone PCR using forward 5'-GGT CGT TCG TCC TTT TAC TGC CTG GAA-3' (SEQ ID NO:134) and reverse 5'-GCC GTC CGT GTG AGG AAT TTT GGC CCA-3' (SEQ ID NO:135) primers (Integrated DNA Technologies). Cycling was carried out as per manufacturer instructions outlined in the GeneMorph II EZ Clone® domain mutagenesis kit (Agilent Technologies). Sequencing of individual clones was carried out by the UNC Genome Analysis facility and capsid sequences were analyzed using VectorNTI® software (Invitrogen).

Molecular Modeling Studies.

Homology models of the VP3 monomer of AAV9 and different variants were generated using the SWISS-MODEL online 3D model building server [44] with the crystal structure of AAV8 as template (PDB ID: 2QA0) [26]. VP3 trimer models were obtained using the online oligomer generator tool in the VIPERdb2 database[45]. Surface rendered depictions of amino acid positions and cartoon models were generated using the program Pymol (The PyMOL Molecular Graphics System, Schrödinger LLC). Lastly, "roadmap" projections of the AAV9 capsid surface highlighting different amino acid residues were constructed using the RIVEM program [46].

Cell Lines, Plasmids and Viruses.

HEK 293 cells were maintained at 37° C. in 5% $CO_2$ in Dulbecco's modified Eagle's medium supplemented with 10% fetal bovine serum and penicillin-streptomycin-amphotericin B. Parental and variant pXR9 plasmid stocks were obtained from the randomized library described herein. The plasmid pXX6-80, containing adenoviral helper genes, was obtained from the UNC vector core. Vector cassettes, pTR-CBA-Luc, containing the chicken beta-actin (CBA) promoter-driven luciferase transgene and pTR-CBA-Tom, encoding tdTomato, a red fluorescent protein, were generated by ligating Luc/Tom inserts flanked by BamHI-NotI sites into the pTR-CBA backbone. Parental and variant AAV9 vectors were produced by the triple-transfection method followed by cesium chloride gradient ultracentrifugation and dialysis as described elsewhere [47]. Viral titers were determined by qPCR using a Roche Lightcycler® with primers specific for the CBA promoter (forward 5'-CGT CAA TGG GTG GAG TAT TT-3' (SEQ ID NO:136); reverse 5'-GCG ATG ACT MT ACG TAG ATG-3' (SEQ ID NO:137)) or Luc transgene region (forward 5'-AAA AGC ACT CTG ATT GAC AAA TAC-3' (SEQ ID NO:138); reverse 5'-CCT TCG CTT CAA MA ATG GM C-3' (SEQ ID NO:139)).

Animal Studies.

At 8-10 weeks of age, animals were injected via the tail vein with a dose of $5 \times 10^{10}$ vector genome-containing particles of AAV9 and related variants packaging CBA-luc or CBA-tom vector cassettes. Luciferase expression in animals was imaged at different time intervals using a Xenogen IVIS Lumina® imaging system (Caliper Lifesciences) following intraperitoneal injection of D-luciferin substrate (120 mg/kg; Nanolight, Pinetop, Ariz.). Bioluminescent image analysis was carried out using the Living Image® software.

Quantitation of Luciferase Expression.

The same group of animals utilized for imaging studies were sacrificed at 4 weeks post-injection and the following organs collected: brain, heart, lung, liver and skeletal muscle (gastrocnemius). Approximately 50 mg of each tissue was homogenized in 150 µl of passive lysis buffer (Promega) using a Tissue lyser II® system (Qiagen). Tissue lysates were centrifuged at 8000 rpm for 2 min to pellet debris and 50 µl of the supernatant transferred to 96-well plates for luminometric analysis (Promega) using a Victor2® luminometer (Perkin Elmer). Total protein concentration in tissue lysates was determined using the Bradford assay (BioRad). For monitoring time course of gene expression, AAV9 and AAV9.45 vectors were administered at a dose of $5 \times 10^{10}$ vg/mouse to three different groups of animals. After being sacrificed at 1, 2 and 4 weeks, heart and liver tissue from each group were processed for quantitation of luciferase transgene expression as described herein. In order to determine the effect of vector dose on transgene expression level, AAV9 and AAV9.45 vectors were administered at three different doses: low ($1 \times 10^{10}$ vg per mouse), medium ($5 \times 10^{10}$ vg per mouse) and high ($1 \times 10^{11}$ vg per mouse). Animals were sacrificed at 2 weeks post-administration, following which heart and liver tissue were processed further for determination of luciferase transgene expression levels.

Quantitation of Vector Genomes.

Approximately 100 µl of supernatant from tissue lysates obtained as described herein was processed using a DNeasy® kit (Qiagen) to extract host and vector genomic DNA. Vector genome (Luc) and mouse lamin gene (internal standard) copy numbers were determined from 100 ng of total extracted DNA using quantitative polymerase chain reaction (qPCR). Vector genome copy numbers in blood were determined at different time intervals following intravenous administration of $1 \times 10^{10}$ particles of AAV9 and related variants packaging the CBA-luc cassette. At 1, 24 and 48 hrs post-injection, 10 µl of whole blood was collected from the tail vein in heparinized capillary tubes (Fisherbrand Hematocrit®) and viral DNA was quantified by qPCR.

Histological Analysis.

Two weeks after intravenous administration of $5 \times 10^{10}$ particles of AAV9 and related variants packaging the CBA-tom cassette, mice were overdosed with intraperitoneal avertin (0.2 mL/10 g of a 1.25% solution) and perfused transcardially with ice-cold phosphate buffered saline (PBS), then freshly prepared 4% paraformaldehyde in PBS. Heart and liver tissues were then fixed overnight at 4° C. and 40 µm thick sections cut using a Leica® vibrating blade microtome. Tissue sections were then imaged using an Olympus fluorescence microscope equipped with a rhodamine filter (emission max: 580 nm) and images were collected using a Hamamatsu digital camera.

Structural Models Reveal Mutations Clustered within the AAV9 VP3 Trimer.

Figure 1C:
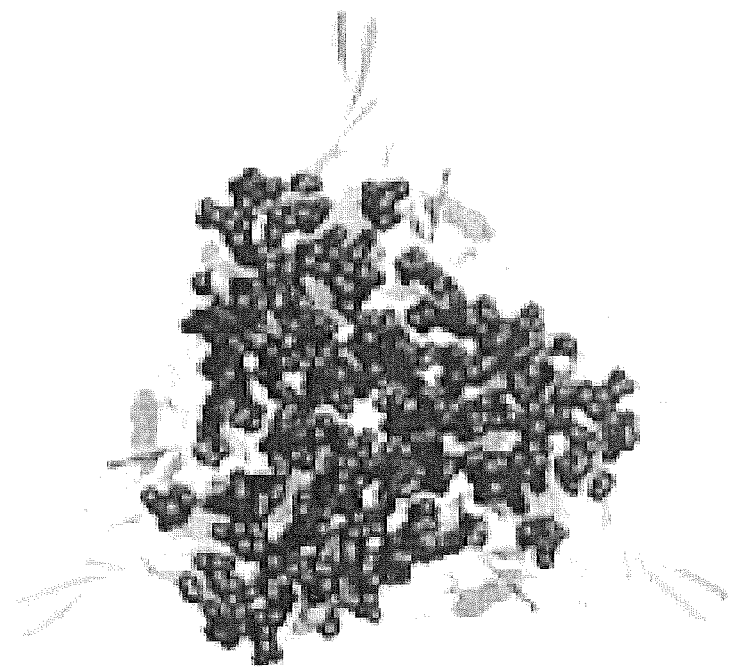
Figure 1D:
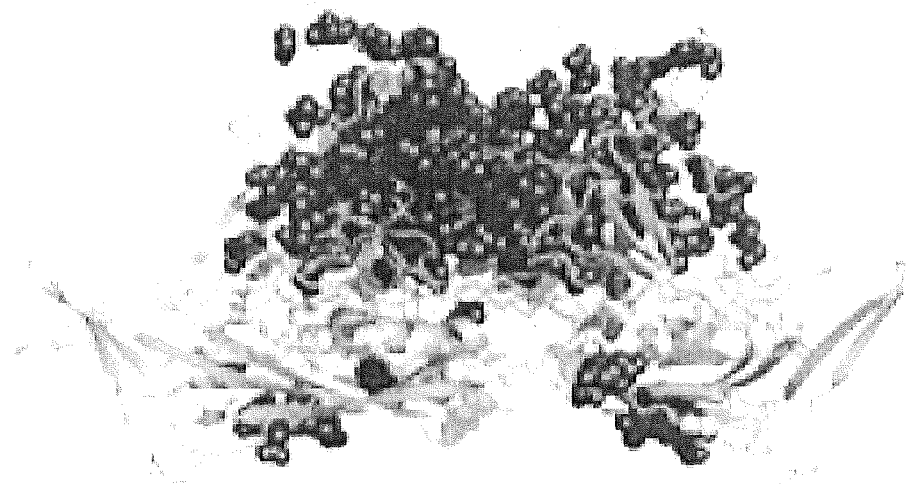
Figure 1E:
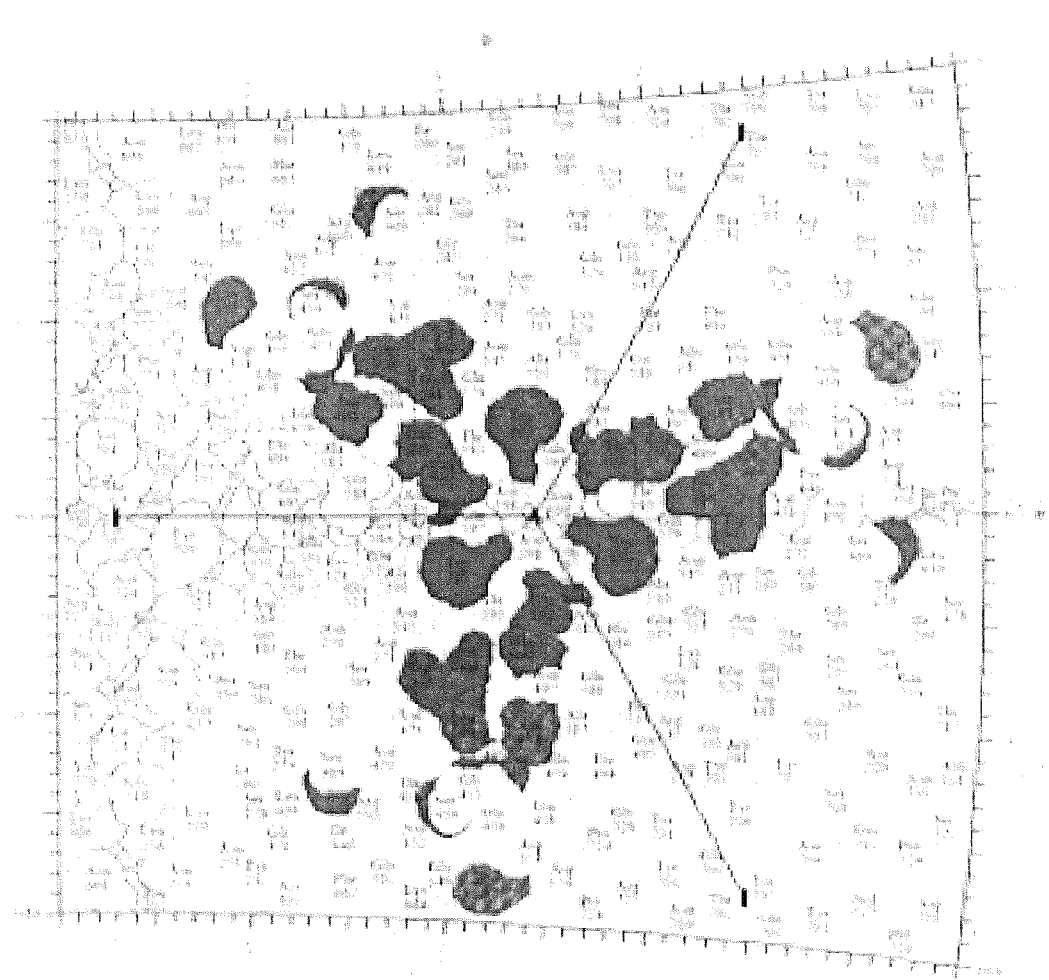

Using error-prone PCR, a diverse AAV9 capsid library with focused mutations on the GH loop spanning amino acids 390-627 (AAV9 VP1 numbering) was generated. A total of 96 variants were sequenced, following which 43 viable clones were obtained (Table 6). Variants with stop codons, frame shift mutations and deletions/insertions were triaged. The variable loop region subjected to mutagenesis is highlighted in red in a model of the VP3 subunit and VP3 trimer of AAV9 (FIGS. 1A,B). Mapping of individual amino acid changes (red spheres) pertaining to each of the 43 different clones onto an AAV9 trimer model revealed clustering of mutations predominantly on the outer surface of VP3 (FIGS. 1C,D). Following this visualization, amino acid changes within beta strands and other regions that are highly conserved among different AAV strains where eliminated from further analysis. Lastly, a schematic "roadmap" projection of the AAV9 capsid model was generated to map the location of surface-exposed mutations (FIG. 1E). Through this combination of sequence analysis and structural analysis, a subset of ten structurally diverse AAV9 surface variants (Table 1) were selected for vector production and characterization in vivo.

AAV9 Variants Display Two Distinct Systemic Transduction Profiles.

Figure 2A:
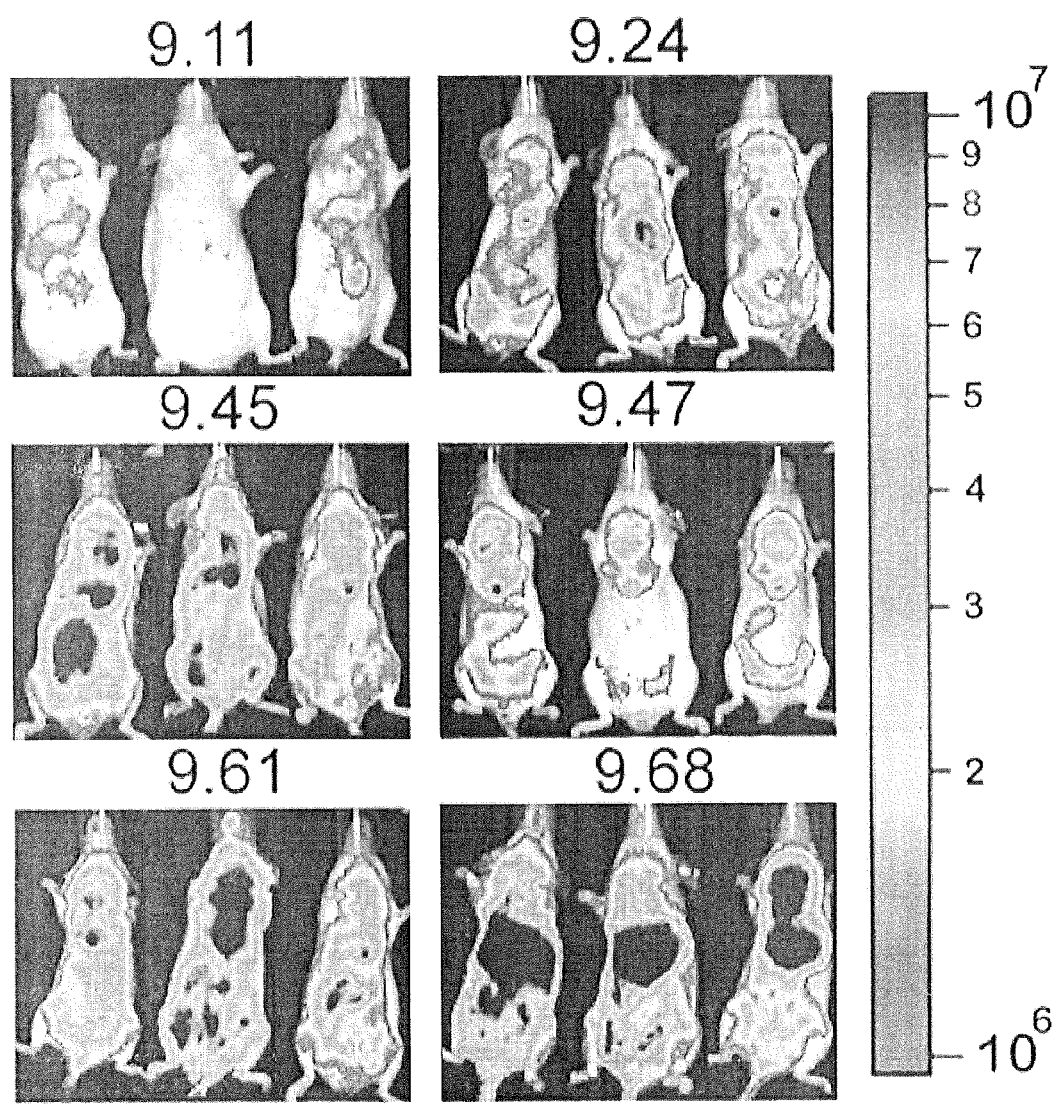
FIGS. 2A-B. Bioluminescent live animal images at 4 weeks post-administration of vectors packaging the CBA-luc transgene cassette. Panels of mice treated with AAV9 variants displaying (A) altered and (B) unaltered transduction profiles relative to parental AAV9 vectors are shown. Images (n=3 each) were obtained at 1 min exposure using a Xenogen IVIS Lumina system equipped with a CCD camera. Scale represents relative light units as determined using the Living Image® software.
Figure 2B:
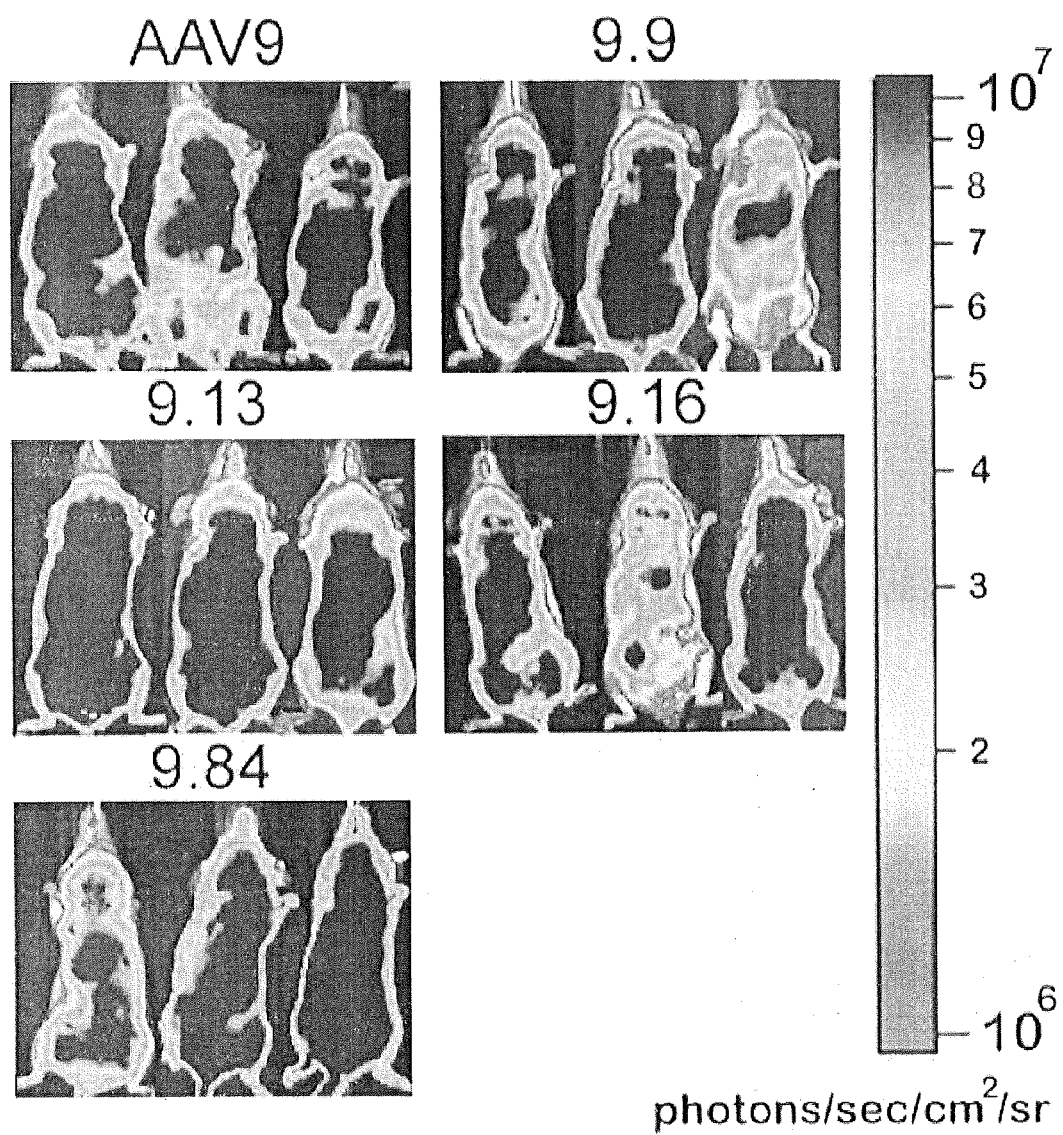

Ten AAV9 variants packaging the chicken beta-actin (CBA) promoter-driven firefly luciferase transgene were generated at titers within 2 to 3-fold that of parental AAV9 vectors. Bioluminescent images of mice injected through the tail vein with different AAV9 variants ($5 \times 10^{10}$ vg/animal) were obtained at 4 weeks post-administration. A qualitative analysis of transduction patterns revealed two distinct profiles, i.e., altered or unaltered when compared to parental AAV9 vectors (FIG. 2A,B). First, as seen in FIG. 2A, variant AAV9.11 appears to be a transduction-deficient variant. Marked changes in transduction profiles along with decreased transduction efficiencies in the liver region are also observed for variants 9.24, 9.45, 9.47 and 9.61. In addition, variant AAV9.68 appears to display a transduction profile favoring the liver. Secondly, as seen in FIG. 2B, variants 9.9, 9.13, 9.16 and 9.84 display transduction profiles that remain largely unaltered compared to AAV9 vectors.

Transgene Expression and Biodistribution Studies Reveal Three Different Functional Phenotypes.

Figure 3:
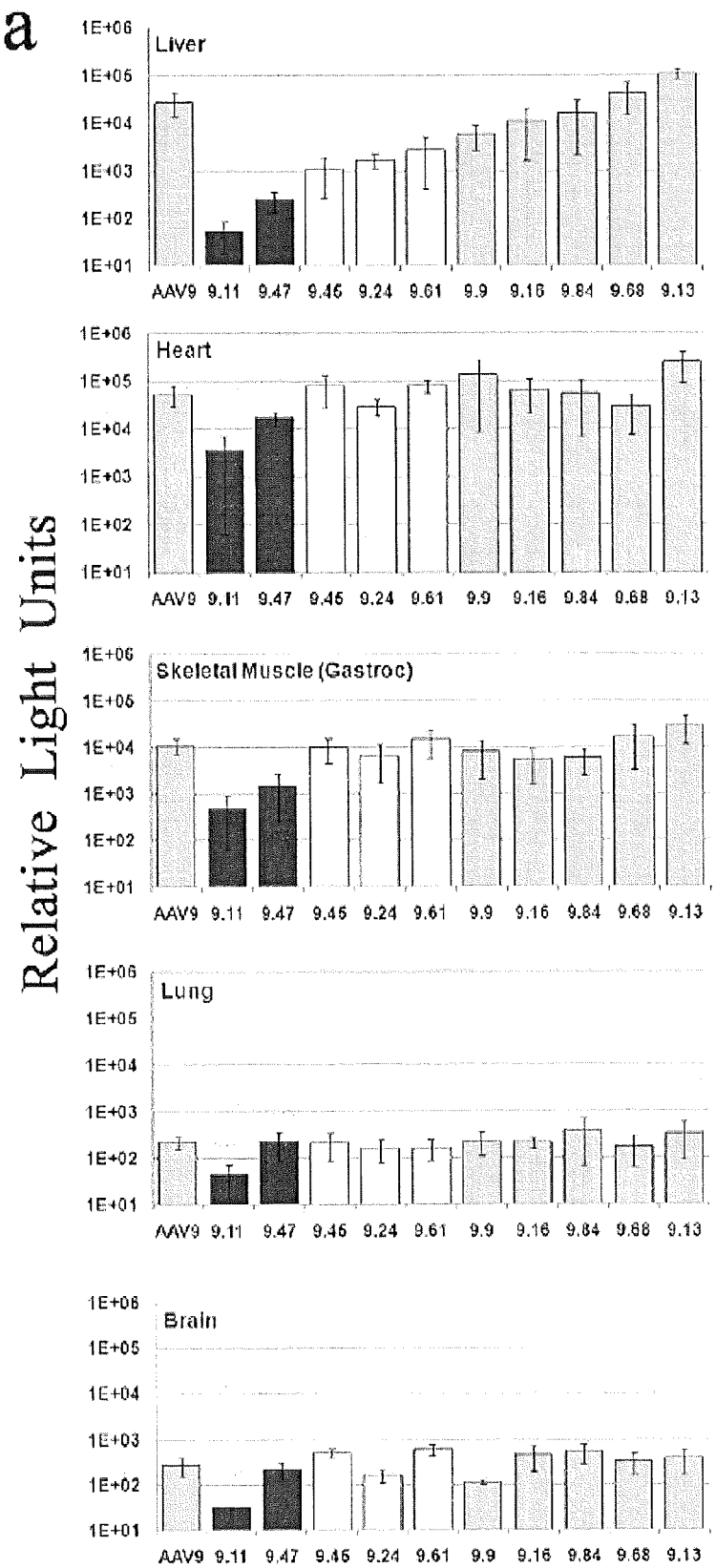
FIGS. 3A-B. Quantitation of luciferase transgene expression levels (A) and vector genome copy numbers (B) at 4 weeks post-injection in different tissue types; heart, liver, skeletal muscle (gastrocnemius), lung and brain. Defective variants 9.11 and 9.47 (black bars) are categorized under functional subtype I; liver-detargeted variants 9.24, 9.45 and 9.61 (white bars) under functional subtype II; and variants largely similar to AAV9 (gray bars) assigned to functional subtype III. Luciferase expression levels were normalized for total tissue protein concentration and data are represented as relative light units. Vector genome copy numbers are normalized per µg of genomic DNA. All experiments were carried out in triplicate. Error bars represent standard deviation.
Figure 3:
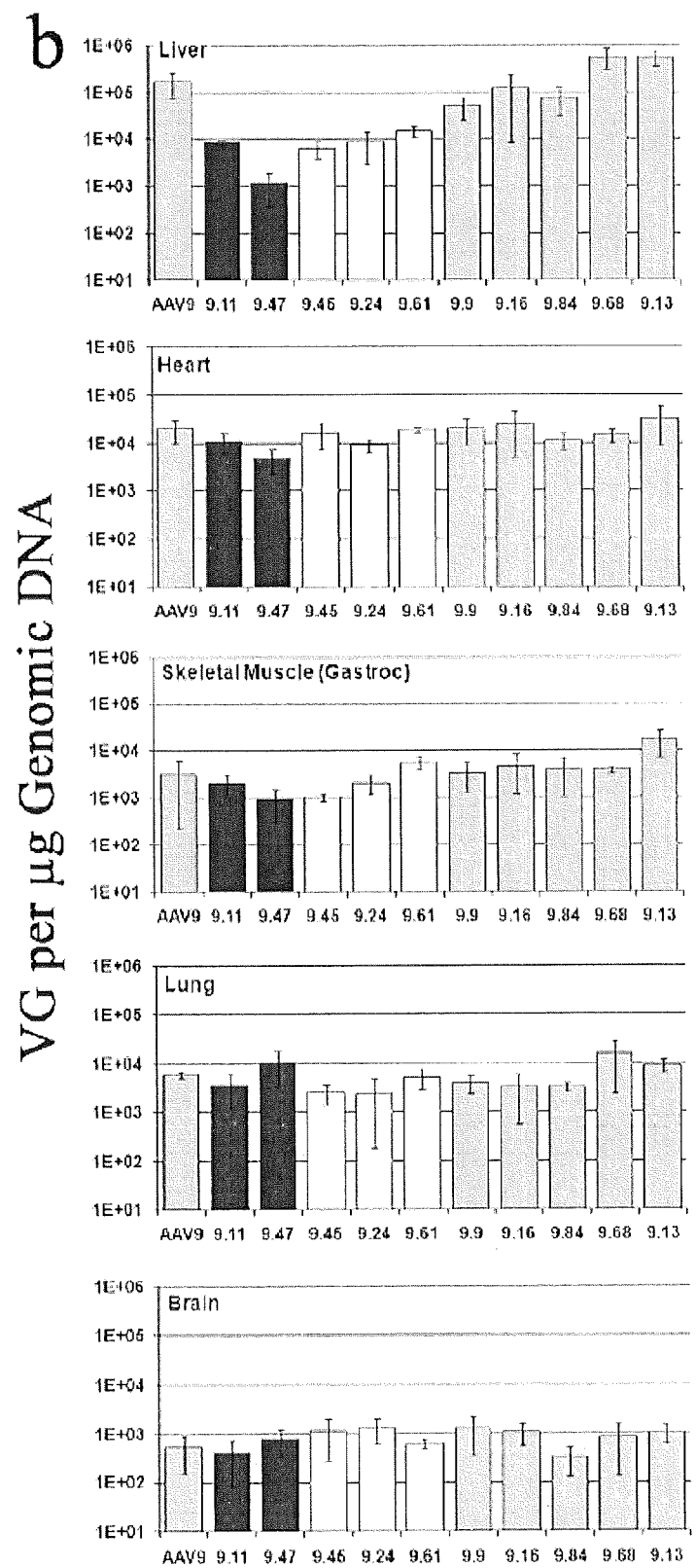

Luciferase activities and vector genome copy numbers in tissue lysates were analyzed to compare transduction efficiencies of AAV9 and the variants in major organs including brain, heart, lung, liver and skeletal muscle. Consistent with previous reports, AAV9 displayed robust transduction in heart, liver, skeletal muscle and modest transgene expression levels in brain and lung [3, 4, 6]. In comparison, several variants displayed transduction efficiencies that ranged from several orders of magnitude lower than AAV9 within the liver to ~1 log unit lower in heart and skeletal muscle (FIG. 3A). A similar trend was noted when comparing the vector genome copy numbers of variants with parental AAV9 in liver, with modest decrease in vector genome copies (5-fold or lower) within other tissues (FIG. 3b). A specific functional subtype was assigned to each individual variant on the basis of their corresponding transduction efficiency and biodistribution profile as detailed herein.

Functional Subtype I.

Variants displaying a defective phenotype were assigned to functional subtype I (black bars, FIG. 3A,B). First, AAV9.11 displayed a significant decrease in transduction efficiency across multiple organs ranging from 5-fold (lung) to 500-fold (liver). For this variant, decrease in vector genome copy numbers within respective tissue types was disproportionate, ranging from no significant change in skeletal muscle to ~1 log unit within the liver. Thus, in agreement with image analysis, AAV9.11 appears to be transduction-deficient. Variant AAV9.47 displays defective transduction levels ranging from 3-fold (heart) and 7-fold (skeletal muscle) to 110-fold (liver). A concomitant decrease in vector genome copy numbers (~4 to 140-fold) is seen in respective tissues. These results support the notion that AAV9.47 might display a defective biodistribution profile, which in turn adversely affects transduction efficiency. Taken together, these results indicate that AAV9.11 and 9.47 constitute the functionally defective subtype I.

Functional Subtype II.

Variants significantly deficient in liver transduction, but showing modest-to-no change (~2-fold or lesser) in other tissue types were assigned to functional subtype II (white bars, FIG. 3A,B). Specifically, variants 9.24, 9.45 and 9.61 displayed ~10 to 25-fold decrease in transduction levels within the liver. A corresponding decrease in vector genome copy numbers ranging from ~10 to 25 fold is also observed within the liver. The AAV9.24 variant displayed a modest, yet significant decrease (~2-fold) in transgene expression levels within the heart and brain. No marked changes in vector genome copy numbers within tissue types other than the liver were observed. Thus, variants 9.24, 9.45 and 9.61 were categorized as liver-detargeted AAV9 variants under the functional subtype II.

Functional Subtype III.

Figure 6:
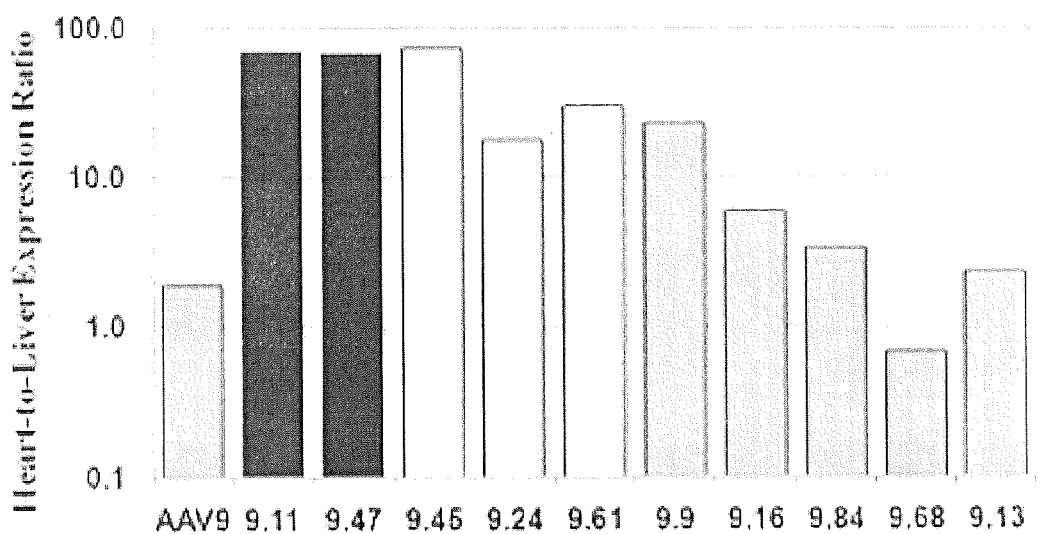
FIGS. 6A-C. Comparison of transduction profiles of parental AAV9 and variants in heart and liver. Heart-to-liver ratios for luciferase expression levels (A) and vector genome copy numbers (B) were derived from average values. Variant 9.45 (white bars) demonstrates high heart-to-liver expression and vg ratios and correspondingly high liver-detargeting efficiency. Variant 9.68 displays heart-to-liver ratios lower than parental AAV9 vectors and hence preferential liver transduction. (C) Fluorescence micrographs of heart, liver and skeletal muscle (gastrocnemius) tissue sections from mice injected with AAV9 or AAV9.45 vectors packaging the CBA-tdTomato cassette. Images were obtained at 20× (liver) or 10× (heart and skeletal muscle) magnification using an Olympus microscope equipped with a Hamamatsu digital camera. Tissue sections from untreated mice are shown as control. All experiments were carried out in duplicate.
Figure 6:
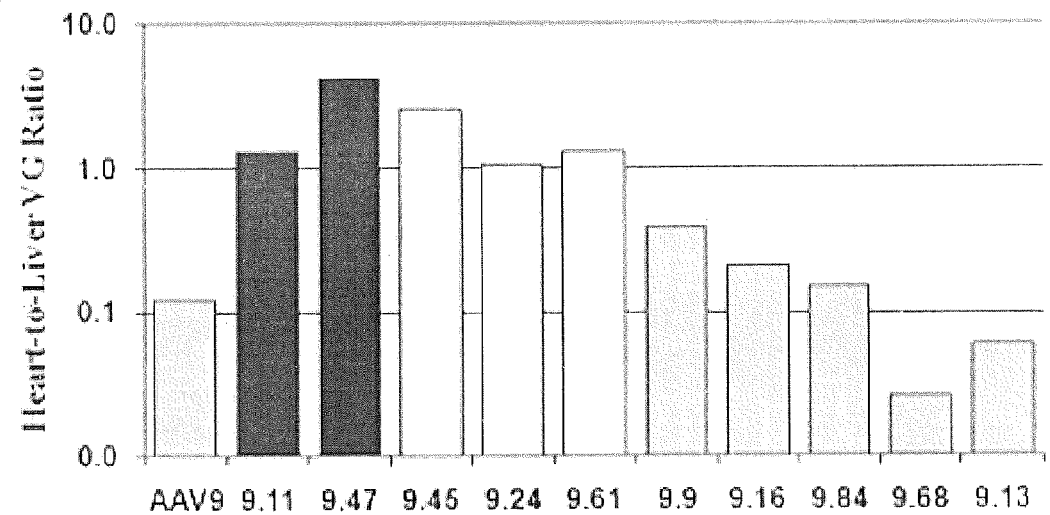
Figure 6:
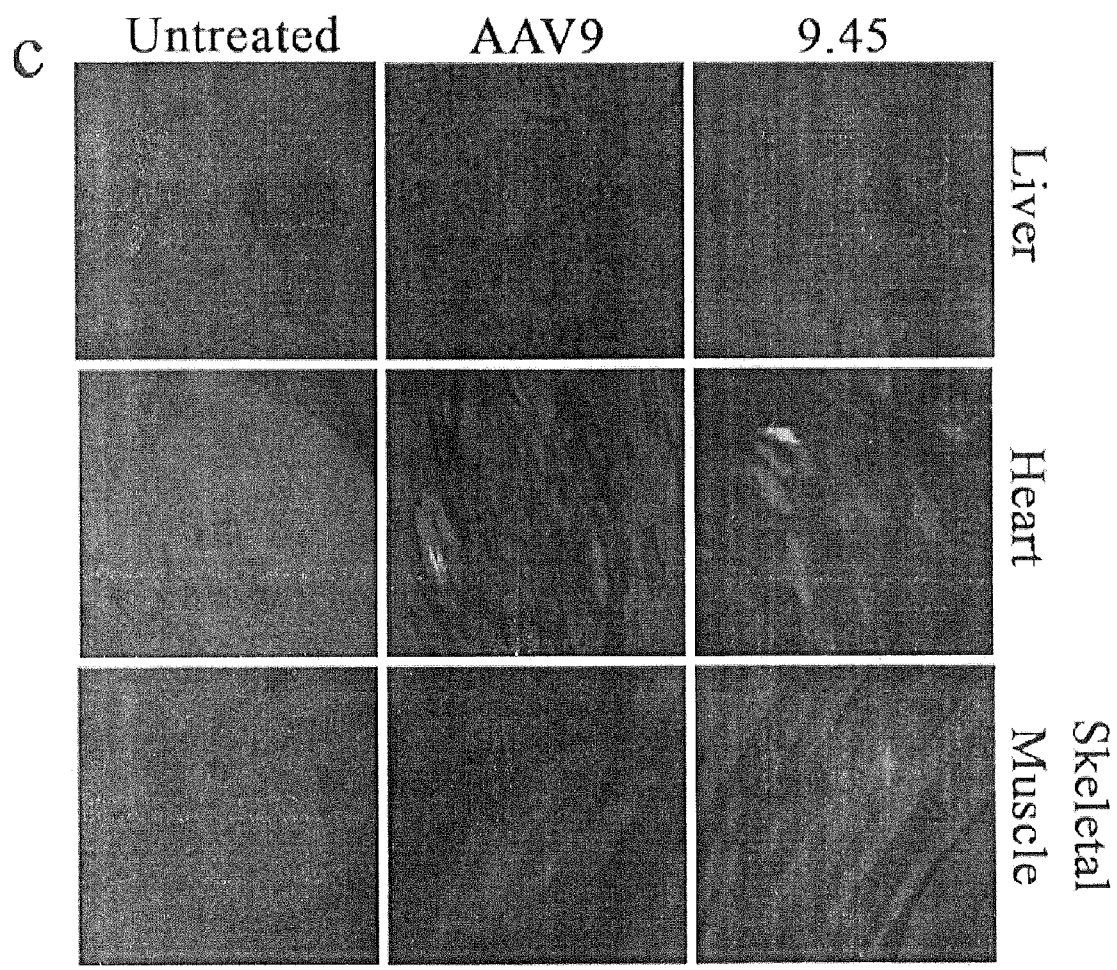

Variants displaying a transduction profile and biodistribution largely similar to AAV9 in multiple tissue types were assigned to functional subtype III (gray bars, FIG. 3A,B). Specifically, AAV9.13 and 9.68 displayed a modest increase (~3 to 5-fold) in transduction efficiency as well as vector genome copy number within different tissue types. Interestingly, AAV9.68 displayed a slightly increased propensity for liver transduction in comparison with AAV9 and other variants as demonstrated by the lower heart-to-liver ratio for gene expression (~3-fold) and vector genome copy number (~5-fold) (FIG. 6A,B). Variants 9.9, 9.16 and 9.84 transduced most tissue types as efficiently as parental AAV9 vectors. The latter subset of AAV9 variants displayed ~2 to 5-fold decrease in transduction levels within the liver and a concomitant decrease in vector genome copy numbers (~2 to 3-fold). Taken together, AAV9.13 and 9.68 were assigned under functional subtype III, while AAV9.9, 9.16 and 9.84 appear to overlap between functional subtypes II and III.

Kinetics of Transgene Expression and Dose Response Profile of AAV9.45 is Distinct from AAV9.

Figure 4:
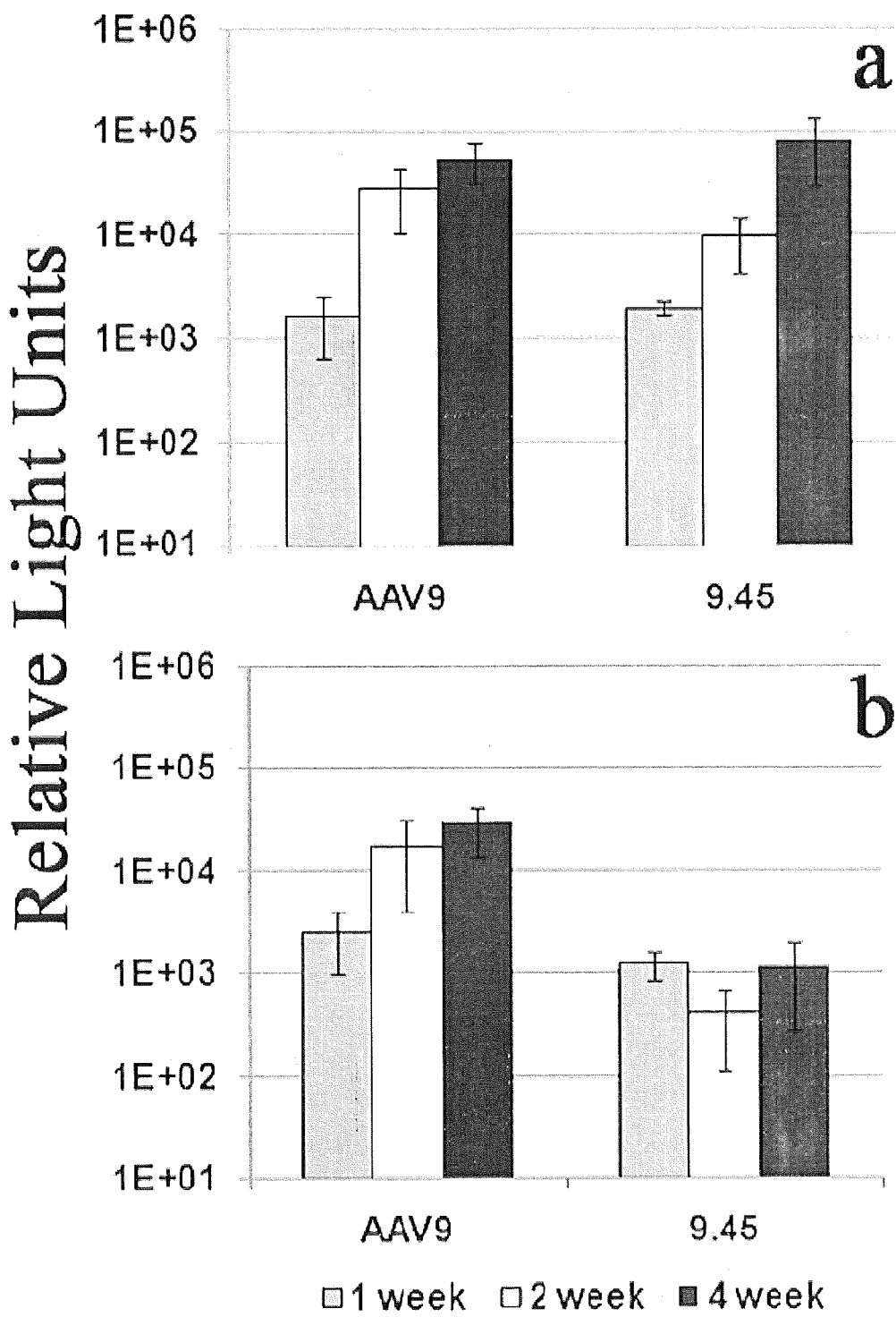
FIGS. 4A-B. Time course of luciferase transgene expression levels following intravenous administration of AAV9 and AAV9.45 vectors ($5 \times 10^{10}$ vg/mouse) in heart (A) and liver (B). Luciferase expression levels determined at 1 week (gray bar), 2 weeks (white bar) and 4 weeks (dark gray bar) were normalized for total tissue protein concentration and data are represented as relative light units. All experiments were carried out in triplicate. Error bars represent standard deviation.
Figure 5:
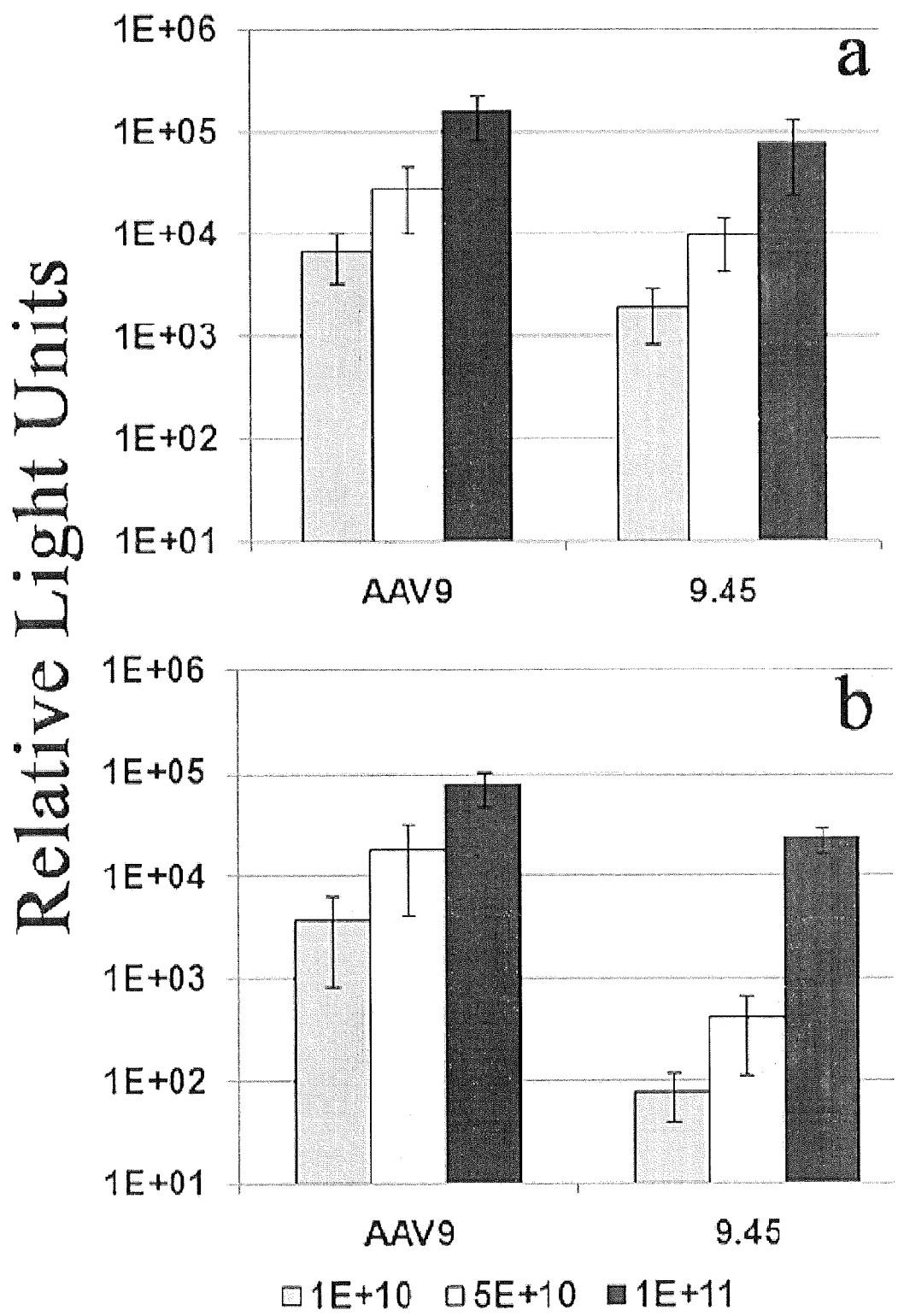
FIGS. 5A-B. Effect of vector dose on luciferase transgene expression levels in heart (A) and liver (B). Parental AAV9 and AAV9.45 vectors were administered intravenously at low (1×low vg/mouse), medium ($5 \times 10^{10}$ vg/mouse) and high ($1 \times 10^{11}$ vg/mouse) dose. Luciferase expression assays were carried out at 2 weeks post-administration and normalized for total tissue protein concentration. Data are represented as relative light units and all experiments were carried out in triplicate. Error bars represent standard deviation.

The effects of vector dose and time course of transgene expression on AAV9 and AAV9.45 vectors were determined. As shown in FIG. 4A, both AAV9 and AAV9.45 demonstrate similar kinetics of transgene expression in the heart. However, in the case of liver, transduction levels achieved by AAV9.45 appear to reach a maximum after 1 week, while AAV9 continues to increase by >1 log unit over 4 weeks (FIG. 4B). In order to gather further insight into the biology of functional subtype II vectors, the effect of increasing vector dose on transduction efficiency of AAV9 and AAV9.45 following intravenous administration was analyzed. Although the dose response profile appears similar between AAV9 and AAV9.45 in heart (FIG. 5A), the latter displays consistently lower transgene expression (~3 to 45-fold) in comparison with AAV9 in the liver (FIG. 5B). A potential explanation for this phenomenon is the saturation of peripheral organs with AAV9.45 vectors at high dose resulting in increased uptake within the liver.

Variant AAV9.45 is Muscle-Tropic and Efficiently Detargeted from the Liver.

The relative tropism of different AAV9 variants for the heart when compared to liver was analyzed. Briefly, ratios of transgene expression levels as well as vector genome copy numbers in heart and liver tissue lysates were obtained and plotted as shown (FIG. 6A,B). Variants 9.16, 9.24, 9.9, 9.61, 9.47, 9.11 and 9.45 displayed heart-to-liver ratios for gene expression ~4 to 40-fold higher than parental AAV9 vectors (FIG. 6A). A concomitant increase in heart-to-liver ratio for vector genome copy number ranging from ~3 to 35-fold was observed (FIG. 6B). Since 9.11 and 9.47 are classified under defective subtype I, variant AAV9.45 appears to display the highest preference for cardiac transduction. The aforementioned results were further corroborated by histological analysis (FIG. 6C). Briefly, AAV9 and AAV9.45 vectors packaging a CBA promoter-driven tdTomato reporter transgene were injected through the tail vein, following which liver, cardiac and skeletal muscle tissue were harvested at 2 weeks post-administration. Fluorescence microscopy of fixed tissue sections confirms that AAV9.45 is cardiac- and skeletal muscle-tropic, while being efficiently detargeted from the liver. In contrast, AAV9 vectors demonstrate robust transduction in all three tissue types as reported previously [3].

An important finding in the current study is the discovery of mutations that result in defective phenotypes. Subtype I includes two variants, AAV9.11 and 9.47 with distinct defects. Mutant 9.11 carries two mutations, T568P and Q590L, which results in a transduction-deficient phenotype. The T568P mutation is buried within the AAV9 trimer and does not appear to impact capsid assembly or packaging efficiency as indicated by viral titers (Table 7). The Q590L mutation is located within the variable region VIII described by Govindasamy et al. [24]. Other variants carrying mutations in the AAV9 inner loop region (residues 590-595, VP1 numbering) include AAV9.9 (W595C) and AAV9.16 (Q592L), which display a modest decrease in transduction efficiency within the liver in comparison with the parental AAV9.

Figure 8:
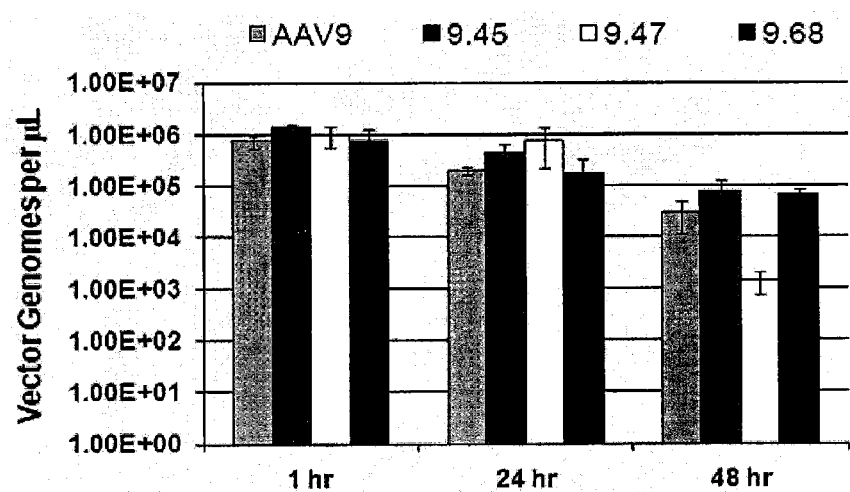
FIG. 8. Blood circulation profiles of AAV9 and representative variants from each functional subtype; AAV9.47 (I), AAV9.45 (II) and AAV9.68 (III). Vector genome copy numbers in blood were determined at different time intervals following intravenous administration of $1 \times 10^{10}$ particles of AAV9 and related variants packaging the CBA-luc cassette. At 1, 24 and 48 hrs post-injection, 10 µl of whole blood was collected from the tail vein in heparinized capillary tubes and viral DNA quantified by qPCR. Vector genome copy numbers are normalized per mL of whole blood. All experiments were carried out in triplicate. Error bars represent standard deviation.
Figure 9A:
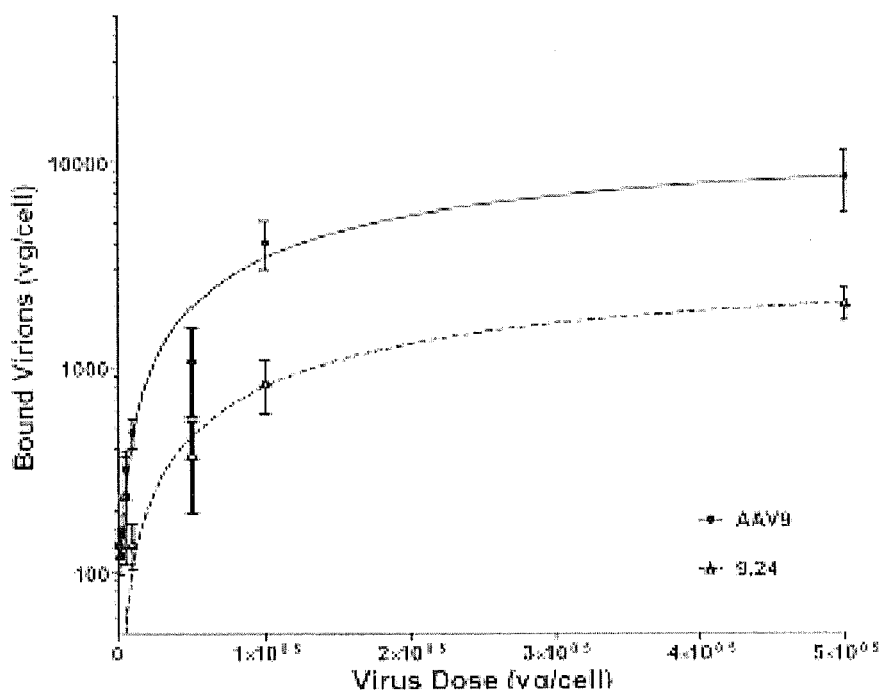
FIGS. 9A-D. Binding curves of AAV9 mutants on Lec2 cell surface. (A) AAV9 vs. 9.24. (B) AAV9 vs. 9.45. (C) AAV9 vs. 9.61. (D) AAV9 vs. 9.98.
Figure 9B:
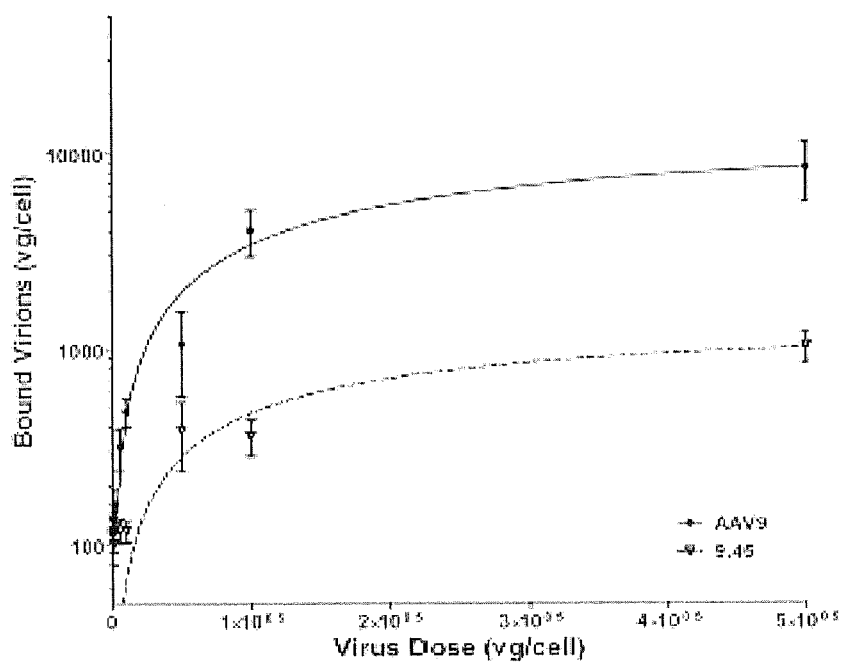
Figure 9C:
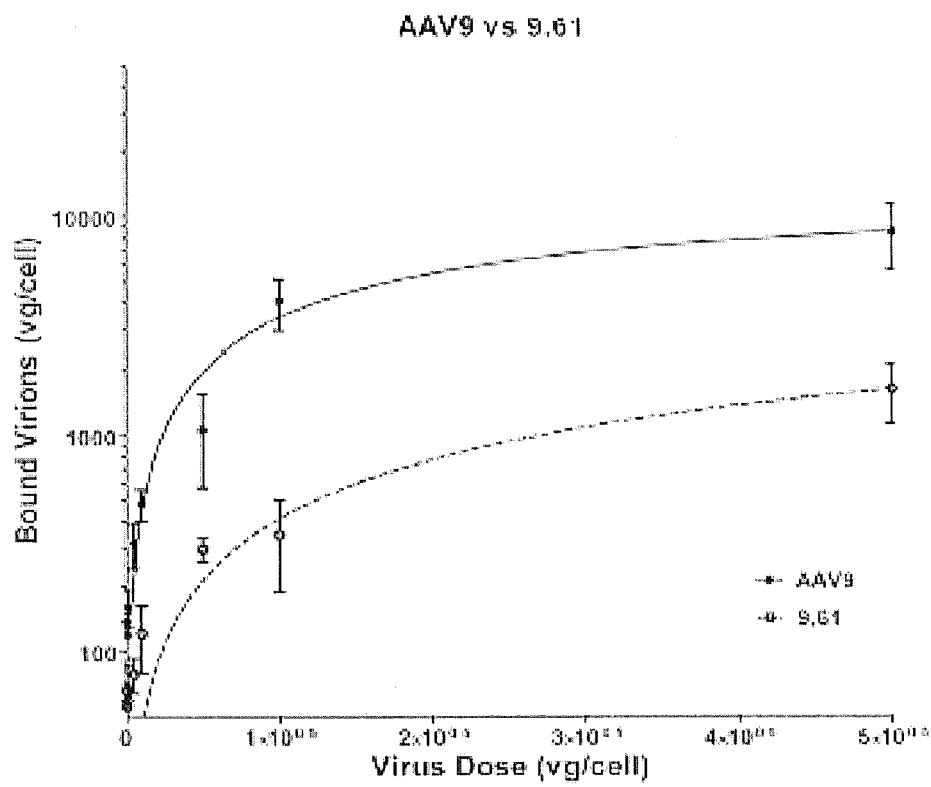
Figure 9D:
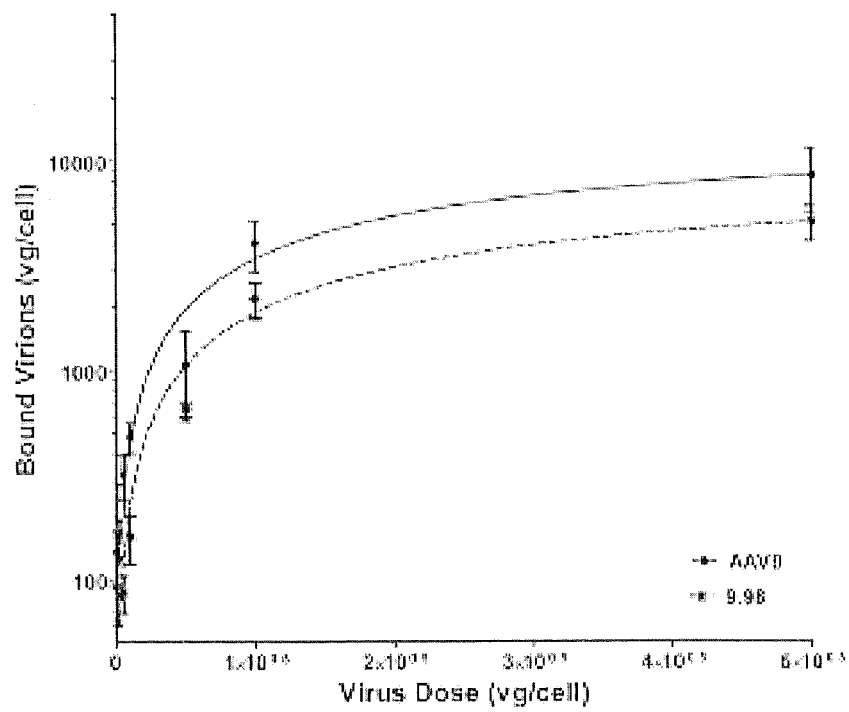

Variant AAV9.47 displayed a defective biodistribution profile, which in turn adversely affected transduction efficiency. Consistent with this defective profile, AAV9.47 is rapidly eliminated from blood circulation when compared to AAV9, AAV9.45 and AAV9.68 vectors (FIG. 8). One plausible explanation for the latter phenotype is the contribution of G453D and K557E mutations to negatively charged clusters on the AAV9.47 surface (FIG. 1E), thereby making the capsid prone to rapid blood clearance.

The current study revealed the role played by specific amino acid residues in conferring liver tropism to AAV9 vectors. Specifically, subtype II variants 9.24, 9.45 and 9.61 appear to possess mutations (at positions N498 and W503) that cluster within variable region V. Further, AAV9.68, a subtype III variant containing a P504I mutation showed preferential liver tropism as demonstrated by a decrease in heart-to-liver transgene expression ratio when compared to AAV9. This region (residues 498-504) is located behind the inner loop residues 590-595 at the three-fold symmetry axis (FIG. 1E). Further optimization of AAV9-derived vectors by varying amino acid residues at different positions and/or combining multiple point mutations (e.g., N498, W503 and W595) onto a single AAV9 capsid template could improve liver detargeting efficiency.

Figure 7:
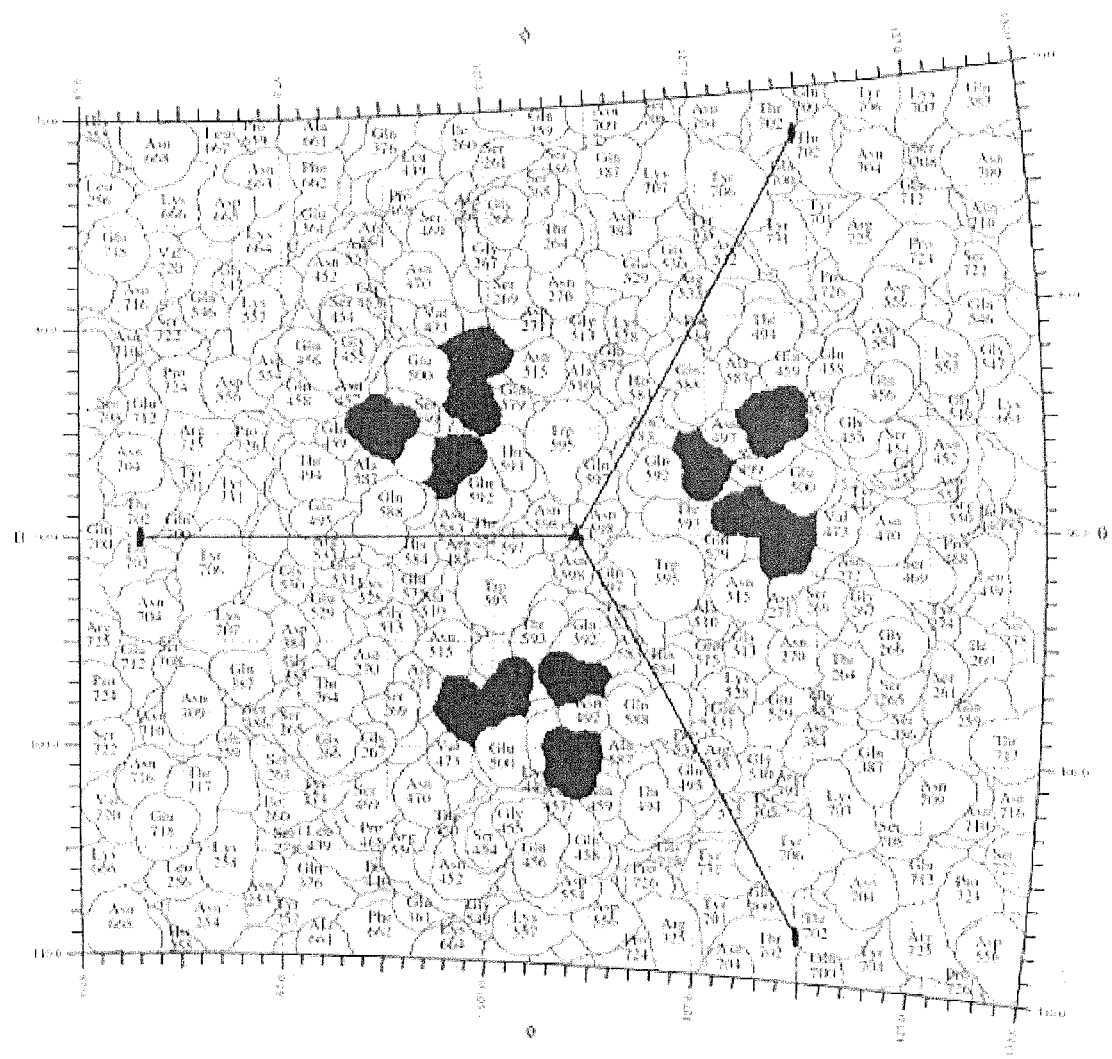
FIG. 7. Putative cluster of residues implicated in AAV9 liver tropism. A spherical roadmap projection of surface residues within the AAV9 capsid trimer region was created as described herein. Key residues, highlighted in red, include N498, W503 (9.45/9.61, 9.24); Q590L (9.11) and P504 (9.68), each derived from mutants categorized under different subtypes. Manipulation of this cluster of residues alters AAV9 liver tropism and might constitute a partial receptor footprint on the AAV9 capsid surface.

Analysis of structural features of different variants in this study suggests that residues 498-504 taken together with the adjacent 590-595 cluster contain key residues (N498, W503, P504, Q590L) that might constitute a partial receptor footprint on the AAV9 capsid (FIG. 7). Consequently, one explanation is that altered affinity for an AAV9 receptor could, in turn, affect liver tropism.

Liver-detargeted AAV9 variants demonstrate significant potential for gene transfer in the treatment of cardiac and musculoskeletal diseases. Further optimization of liver-detargeted AAV9 vectors with transcriptional targeting elements such as cardiac or muscle-specific promoters [39, 40] or microRNA-122 target sequences [41, 42] would allow selective delivery of therapeutic transgenes to heart and/or skeletal muscle.

Studies on Binding Affinity of AAV9 Mutants to Galactosylated Glycans on Chinese Hamster Ovary (CHO) Cells.

The experiments of FIGS. 9 and 10 were carried out to evaluate the binding of different AAV9 mutants to galactosylated glycans on CHO cells. Briefly, cells were incubated with different titers of virus particles at 4° C. and the amount of virus bound was calculated (after washing off unbound virus) using quantitative PCR. The data obtained were then fit to a single site binding model and binding parameters calculated as described in FIG. 10. The results confirm that AAV9 mutants detargeted from the liver display low glycan binding potential. AAV9 vectors comprising capsid proteins comprising one or more mutations resulting in reduced glycan binding affinity have utility in gene transfer protocols in therapeutic applications where the liver is not the primary organ of interest.

The foregoing is illustrative of the present invention, and is not to be construed as limiting thereof. The invention is defined by the following claims, with equivalents of the claims to be included therein.

REFERENCES

1. Herzog R W, Cao O, Srivastava A (2010) Two decades of clinical gene therapy—success is finally mounting. *Discov. Med.;* 9: 105-111
2. Mitchell A M, Nicolson S C, Warischalk J K, Samulski R J (2010) AAV's Anatomy: Roadmap for Optimizing Vectors for Translational Success. *Curr. Gene Ther.;* 10: 319-340
3. Zincarelli C, Soltys S, Rengo G, Rabinowitz J E (2008) *Analysis of M V serotypes* 1-9 mediated gene expression and tropism in mice after systemic injection. *Mol. Ther.;* 16: 1073-1080
4. Inagaki K, Fuess S, Storm T A, Gibson G A, Mctiernan C F, Kay M A, et al. (2006) Robust systemic transduction with AAV9 vectors in mice: efficient global cardiac gene transfer superior to that of AAV8. *Mol. Ther.;* 14: 45-53
5. Pacak C A, Mah C S, Thattaliyath B D, Conlon T J, Lewis M A, Cloutier D E, et al. (2006) Recombinant adeno-associated virus serotype 9 leads to preferential cardiac transduction in vivo. *Circ. Res.;* 99: e3-9
6. Yang L, Jiang J, Drouin L M, Agbandje-McKenna M, Chen C, Qiao C, et al. (2009) A myocardium tropic adeno-associated virus (AAV) evolved by DNA shuffling and in vivo selection. *Proc. Natl. Acad. Sci. U.S.A;* 106: 3946-3951
7. Foust K D, Nurre E, Montgomery C L, Hernandez A, Chan C M, Kaspar B K (2009) Intravascular AAV9 preferentially targets neonatal neurons and adult astrocytes. *Nat. Biotechnol.;* 27: 59-65
8. Kornegay J N, Li J, Bogan J R, Bogan D J, Chen C, Zheng H, et al. (2010) Widespread muscle expression of an AAV9 human mini-dystrophin vector after intravenous injection in neonatal dystrophin-deficient dogs. *Mol. Ther.;* 18: 1501-1508
9. Lipskaia L, Chemaly E R, Hadri L, Lompre A M, Hajjar R J. (2010) Sarcoplasmic reticulum Ca(2+) ATPase as a therapeutic target for heart failure. *Expert Opin Biol Ther.;* 10: 29-41
10. Hasbrouck N C, High K A (2008) AAV-mediated gene transfer for the treatment of hemophilia B: problems and prospects. *Gene Ther.;* 15: 870-875
11. Brantly M L, Chulay J D, Wang L, Mueller C, Humphries M, Spencer L T, et al. (2009) Sustained transgene expression despite T lymphocyte responses in a clinical trial of rAAV1-AAT gene therapy. *Proc. Natl. Acad. Sci. U.S.A;* 106: 16363-16368
12. Halbert C L, Madtes D K, Vaughan A E, Wang Z, Storb R, Tapscott S J, et al. (2010) Expression of human alpha1-antitrypsin in mice and dogs following AAV6 vector-mediated gene transfer to the lungs. *Mol. Ther.;* 18: 1165-1172
13. Salve M Z, Himeda C L, Tai P W, Nishiuchi E, Gregorevic P, Allen J M, et al. (2007) Design of tissue-specific regulatory cassettes for high-level rAAV-mediated expression in skeletal and cardiac muscle. Mol. Ther.; 15: 320-329
14. Wang B, Li J, Fu F H, Chen C, Zhu X, Zhou L, et al. (2008) Construction and analysis of compact muscle-specific promoters for AAV vectors. *Gene Ther.;* 15: 1489-1499
15. Brown B D, Naldini L (2009) Exploiting and antagonizing microRNA regulation for therapeutic and experimental applications. *Nat. Rev. Genet.;* 10: 578-585
16. Michelfelder S, Kohlschutter J, Skorupa A, Pfennings S, Muller O, Kleinschmidt J A, et al. (2009) Successful expansion but not complete restriction of tropism of adeno-associated virus by in vivo biopanning of random virus display peptide libraries. *PLoS One;* 4: e5122
17. Ying Y, Muller O J, Goehringer C, Leuchs B, Trepel M, Katus H A, at al. (2010) Heart-targeted adeno-associated viral vectors selected by in vivo biopanning of a random viral display peptide library. *Gene Ther.;* 17: 980-990
18. Excoffon K J, Koerber J T, Dickey D D, Murtha M, Keshavjee S, Kaspar B K, et al. (2009) Directed evolution of adeno-associated virus to an infectious respiratory virus. *Proc. Natl. Acad. Sci. U.S.A;* 106: 3865-3870
19. Koerber J T, Klimczak R, Jang J H, Dalkara D, Flannery J G, Schaffer D V (2009) Molecular evolution of adeno-associated virus for enhanced glial gene delivery. *Mol. Ther.;* 17: 2088-2095
20. Opie S R, Warrington K H, Jr, Agbandje-McKenna M, Zolotukhin S, Muzyczka N (2003) Identification of amino acid residues in the capsid proteins of adeno-associated virus type 2 that contribute to heparan sulfate proteoglycan binding. *J. Virol.;* 77: 6995-7006
21. Kern A, Schmidt K, Leder C, Muller O J, Wobus C E, Bettinger K, at al. (2003) Identification of a heparin-binding motif on adeno-associated virus type 2 capsids. *J. Virol.;* 77: 11072-11081
22. Asokan A, Hamra J B, Govindasamy L, Agbandje-McKenna M, Samulski R J (2006) Adeno-associated virus type 2 contains an integrin alpha5beta1 binding domain essential for viral cell entry. *J. Virol*.; 80: 8961-8969
23. Xie Q, Bu W, Bhatia S, Hare J, Somasundaram T, Azzi A, at al. (2002) The atomic structure of adeno-associated virus (AAV-2), a vector for human gene therapy. *Proc. Natl. Acad. Sci. U.S.A;* 99: 10405-10410
24. Govindasamy L, Padron E, McKenna R, Muzyczka N, Kaludov N, Chiorini J A, et al. (2006) Structurally mapping the diverse phenotype of adeno-associated virus serotype 4. *J. Virol*.; 80: 11556-11570
25. Wu Z, Asokan A, Grieger J C, Govindasamy L, Agbandje-McKenna M, Samulski R J (2006) Single amino acid changes can influence titer, heparin binding, and tissue tropism in different adeno-associated virus serotypes. *J. Virol*.; 80: 11393-11397
26. Nam H J, Lane M D, Padron E, Gurda B, McKenna R, Kohlbrenner E, et al. (2007) Structure of adeno-associated virus serotype 8, a gene therapy vector. *J. Virol*.; 81: 12260-12271
27. Asokan A, Conway J C, Phillips J L, Li C, Hegge J, Sinnott R, et al. (2010) Reengineering a receptor footprint of adeno-associated virus enables selective and systemic gene transfer to muscle. *Nat. Biotechnol.;* 28: 79-82

28. Bish L T, Morine K, Sleeper M M, Sanmiguel J, Wu D, Gao G, et al. (2008) Adeno-associated virus (AAV) serotype 9 provides global cardiac gene transfer superior to AAV1, AAV6, AAV7, and AAV8 in the mouse and rat. *Hum. Gene Ther.;* 19: 1359-1368
29. Levy H C, Bowman V D, Govindasamy L, McKenna R, Nash K, Warrington K, et al. (2009) Heparin binding induces conformational changes in Adeno-associated virus serotype 2. *J. Struct. Biol.;* 165: 146-156
30. Lerch T F, Xie Q, Chapman M S (2010) The structure of adeno-associated virus serotype 3B (AAV-3B): insights into receptor binding and immune evasion. *Virology;* 403: 26-36
31. Molenaar T J, Michon I, de Haas S A, van Berkel T J, Kuiper J, Biessen E A (2002) Uptake and processing of modified bacteriophage M13 in mice: implications for phage display. *Virology;* 293: 182-191
32. Prasuhn D E, Jr, Singh P, Strable E, Brown S, Manchester M, Finn M G (2008) Plasma clearance of bacteriophage Qbeta particles as a function of surface charge. *J. Am. Chem. Soc.;* 130: 1328-1334
33. Michelfelder S, Trepel M (2009) Adeno-associated viral vectors and their redirection to cell-type specific receptors. *Adv. Genet;* 67: 29-60
34. Lochrie M A, Tatsuno G P, Christie B, McDonnell J W, Zhou S, Surosky R, et al. (2006) Mutations on the external surfaces of adeno-associated virus type 2 capsids that affect transduction and neutralization. *J. Virol.;* 80: 821-834
35. Akache B, Grimm D, Pandey K, Yant S R, Xu H, Kay M A (2006) The 37/67-kilodalton laminin receptor is a receptor for adeno-associated virus serotypes 8, 2, 3, and 9. *J. Virol.;* 80: 9831-9836
36. Rubio M P, Lopez-Bueno A, Almendral J M (2005) Virulent variants emerging in mice infected with the apathogenic prototype strain of the parvovirus minute virus of mice exhibit a capsid with low avidity for a primary receptor. *J. Virol.;* 79: 11280-11290
37. Nam H J, Gurda-Whitaker B, Gan W Y, Ilaria S, McKenna R, Mehta P, et al. (2006) Identification of the sialic acid structures recognized by minute virus of mice and the role of binding affinity in virulence adaptation. *J. Biol. Chem.;* 281: 25670-25677
38. Kalyuzhniy O, Di Paolo N C, Silvestry M, Hofherr S E, Barry M A, Stewart P L et al. (2008) Adenovirus serotype 5 hexon is critical for virus infection of hepatocytes in vivo. *Proc Natl Acad Sci USA.;* 105(14): 5483-5488
39. Boecker W, Bernecker O Y, Wu J C, Zhu X, Sawa T, Grazette L, et al. (2004) Cardiac-specific gene expression facilitated by an enhanced myosin light chain promoter. *Mol. Imaging;* 3: 69-75
40. Wang B, Li J, Fu F H, Chen C, Zhu X, Zhou L, et al. (2008) Construction and analysis of compact muscle-specific promoters for AAV vectors. *Gene Ther.;* 15: 1489-1499
41. Qiao C, Yuan Z, Li J, He B, Zheng H, Mayer C, et al. (2010) Liver-specific microRNA-122 target sequences incorporated in AAV vectors efficiently inhibits transgene expression in the liver. *Gene Ther.* [Epub ahead of print]
42. Geisler A, Jungmann A, Kurreck J, Poller W, Katus H A, Vetter R, et al. (2010) microRNA122-regulated transgene expression increases specificity of cardiac gene transfer upon intravenous delivery of AAV9 vectors. *Gene Ther.* [Epub ahead of print]
43. Gao G, Vandenberghe L H, Alvira M R, Lu Y, Calcedo R, Zhou X, et al. (2004) Clades of adeno-associated viruses are widely disseminated in human tissues. *J. Virol.;* 78: 6381-6388
44. Arnold K, Bordoli L, Kopp J, Schwede T (2006) The SWISS-MODEL workspace: a web-based environment for protein structure homology modelling. *Bioinformatics;* 22: 195-201
45. Carrillo-Tripp M, Shepherd C M, Borelli I A, Venkataraman S, Lander G, Natarajan P, et al. (2009) VIPERdb2: an enhanced and web API enabled relational database for structural virology. *Nucleic Acids Res.;* 37: D436-42
46. Xiao C, Rossmann M G (2007) Interpretation of electron density with stereographic roadmap projections. *J. Struct. Biol.;* 158: 182-187
47. Grieger J C, Choi V W, Samulski R J (2006) Production and characterization of adeno-associated viral vectors. *Nat. Protoc.;* 1: 1412-1428

TABLE 1

| Complete Genomes | GenBank ® Database Accession Number |
|---|---|
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |

TABLE 1-continued

| Complete Genomes | GenBank ® Database Accession Number |
|---|---|
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

TABLE 2

| Amino Acid Residue | Three-Letter Code | One-Letter Code (can be upper or lower case) |
|---|---|---|
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 3

| Modified Amino Acid Residue | Abbreviation |
|---|---|
| Amino Acid Residue Derivatives | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | alle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |

TABLE 3-continued

| Modified Amino Acid Residue | Abbreviation |
|---|---|
| Amino Acid Residue Derivatives | |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

TABLE 4

| Serotype | Position 1 | Position 2 |
|---|---|---|
| AAV1 | A263X | T265X |
| AAV2 | Q263X | -265X |
| AAV3a | Q263X | -265X |
| AAV3b | Q263X | -265X |
| AAV4 | S257X | -259X |
| AAV5 | G253X | V255X |
| AAV6 | A263X | T265X |
| AAV7 | E264X | A266X |

TABLE 4-continued

| Serotype | Position 1 | Position 2 |
|---|---|---|
| AAV8 | G264X | S266X |
| AAV9 | S263X | S265X |

Where,
(X) → mutation to any amino acid
(-) → insertion of any amino acid
Note:
Position 2 inserts are indicated by the site of insertion

TABLE 5

| Point Mutations | Functional Subtype* |
|---|---|
| W595C | II/III |
| T568P, Q590L | I |
| N457H, T574S | III |
| Q592L | II/III |
| W503R | II |
| N498Y, L602F | II |
| S414N, G453D, K557E, T582I | I |
| N498I | II |
| P504T | III |
| P468T, E500D | II/III |
| R514A | I |

*I - transduction-deficient; II - liver-detargeted; III - similar to AAV9

TABLE 6

List of variants*

| | | | | | | | |
|---|---|---|---|---|---|---|---|
| 9.1 | G1594C - D532H | | | | | | |
| 9.2 | T1418A - V473D | T1436 - I479K | | | | | |
| 9.3 | T1238A - F413Y | | | | | | |
| 9.4 | T1250C - F417S | A1617T - NC | | | | | |
| 9.5 | A1235G - Q412R | A1314T - NC | A1642G - T548A | C1760T - A587V | | | |
| 9.6 | T1231A - F411I | | | | | | |
| 9.9 | G1203A - NC | G1785T - W595C | | | | | |
| 9.10 | A1500G - NC | T1676C - M559T | | | | | |
| 9.11 | A1425T - NC | A1702C - T568P | A1769T - Q590L | | | | |
| 9.13 | A1369C - N457H | A1720T - T574S | | | | | |
| 9.14 | T1340A - L447H | T1362C - NC | T1560C - NC | G1713A - NC | | | |
| 9.16 | A1775T - Q592L | | | | | | |
| 9.24 | T1507C - W503R | T1521G - NC | | | | | |
| 9.26 | A1337G - Y446C | A1769C - Q590P | | | | | |
| 9.33 | A1667C - D556A | | | | | | |
| 9.34 | A1534G - N512D | C1794T - NC | | | | | |
| 9.35 | A1289T - Q430L | T1450A - Y484N | C1494T - NC | A1515T - NC | C1794A - N598K | G1816A - V606I | |
| 9.40 | A1694T - E565V | | | | | | |
| 9.41 | A1348T - T450S | T1362C - NC | | | | | |
| 9.44 | A1684C - N562H | A1701T - K567N | A1737G - NC | | | | |
| 9.45 | A1492T - N498Y | C1804T - L602F | | | | | |
| 9.46 | G1441C - G481R | T1525C - W509R | T1549G - L517V | | | | |
| 9.47 | G1241A - S414N | G1358A - G453D | A1669G - K557E | C1745T - T582I | | | |
| 9.48 | C1445T - P482L | A1736T - Q579L | | | | | |
| 9.50 | A1638T - Q546H | C1683T - NC | T1805A - L602H | | | | |
| 9.53 | G1301A - R434Q | A1405C - S469R | C1664T - A555V | G1811T - G604V | | | |
| 9.54 | C1531A - L511I | T1609A - L537M | | | | | |
| 9.55 | T1605A - F535L | | | | | | |
| 9.58 | C1475T - T492I | C1579A - H527N | | | | | |
| 9.59 | T1336C - Y446H | | | | | | |
| 9.61 | A1493T - N498I | | | | | | |
| 9.64 | C1531A - L511I | A1617T - NC | | | | | |
| 9.65 | C1335T - NC | T1530C - NC | C1568A - A523D | | | | |
| 9.68 | C1510A - P504T | | | | | | |
| 9.80 | G1441A - G481R | | | | | | |
| 9.83 | A1314T - NC | A1694G - E565G | A1751T - H584L | | | | |
| 9.84 | C1402A - P468T | A1500T - E500D | | | | | |
| 9.87 | T1464C - NC | T1468C - S490P | | | | | |
| 9.90 | A1196T - Y399F | | | | | | |
| 9.91 | T1316G - L439R | A1583T - K528I | C1782G - NC | T1806C - NC | | | |
| 9.93 | A1273G - S425G | A1421G - Q474R | A1638C - Q546H | C1712T - P571L | G1732A - G578R | A1744T - T582S | A1832T - D611V |

TABLE 6-continued

List of variants*

| | |
|---|---|
| 9.94 | A1675T - M559L |
| 9.95 | T1605A - F535L |

*List of point mutations in 43 viable AAV9 variants obtained after screening 95 clones. The remaining clones had stop codons, silent mutations, insertions and deletions leading to frame shift. NC—no change of amino acid (silent mutation)

TABLE 7

Vector Genome Titers

| Variant | vg/μl* |
|---|---|
| AAV9 | 3.36E+08 |
| 9.9 | 9.41E+08 |
| 9.11 | 7.33E+08 |
| 9.13 | 6.56E+08 |
| 9.16 | 6.27E+08 |
| 9.24 | 3.09E+08 |
| 9.45 | 2.38E+08 |
| 9.47 | 3.41E+08 |
| 9.61 | 3.49E+08 |
| 9.68 | 2.13E+08 |
| 9.84 | 5.47E+08 |

*Titers are average of two sample titers

VARIANT: 9.24/MUTATION SHOWN: W503R

| Serotype | Position | Residue |
|---|---|---|
| AAV9 | 503 | W |
| AAV1 | 503 | W |
| AAV2 | 502 | W |
| AAV3 | 503 | W |
| AAV4 | 502 | I |
| AAV5 | 489 | F |
| AAV6 | 503 | W |
| AAV7 | 505 | W |
| AAV8 | 505 | W |
| AAV10 | 505 | W |
| AAV11 | 501 | L |
| AAV12 | 510 | L |

VARIANT: 9.45/MUTATIONS SHOWN: N498Y, L602F

| Serotype | Position | Residue | Serotype | Position | Residue |
|---|---|---|---|---|---|
| AAV9 | 498 | N | AAV9 | 602 | L |
| AAV1 | 498 | N | AAV1 | 602 | L |
| AAV2 | 497 | N | AAV2 | 601 | L |
| AAV3 | 498 | N | AAV3 | 602 | L |
| AAV4 | 497 | G | AAV4 | 600 | V |
| AAV5 | 484 | A | AAV5 | 591 | V |
| AAV6 | 498 | N | AAV6 | 602 | L |
| AAV7 | 500 | N | AAV7 | 603 | L |
| AAV8 | 500 | N | AAV8 | 604 | L |
| AAV10 | 500 | N | AAV10 | 604 | L |
| AAV11 | 496 | G | AAV11 | 599 | L |
| AAV12 | 505 | G | AAV12 | 608 | V |

VARIANT: 9.47/MUTATIONS SHOWN: S414N, K557E, T582I

| Serotype | Position | Residue | Serotype | Position | Residue | Serotype | Position | Residue |
|---|---|---|---|---|---|---|---|---|
| AAV9 | 414 | S | AAV9 | 557 | K | AAV9 | 582 | T |
| AAV1 | 413 | S | AAV1 | 557 | N | AAV1 | 582 | V |
| AAV2 | 412 | S | AAV2 | 556 | K | AAV2 | 581 | T |
| AAV3 | 412 | S | AAV3 | 557 | N | AAV3 | 582 | N |
| AAV4 | 406 | T | AAV4 | 555 | T | AAV4 | 580 | G |
| AAV5 | 405 | T | AAV5 | 546 | N | AAV5 | 571 | T |
| AAV6 | 413 | S | AAV6 | 557 | N | AAV6 | 582 | V |
| AAV7 | 414 | S | AAV7 | 558 | N | AAV7 | 583 | S |
| AAV8 | 415 | T | AAV8 | 559 | D | AAV8 | 584 | D |
| AAV10 | 415 | S | AAV10 | 559 | S | AAV10 | 584 | D |
| AAV11 | 405 | A | AAV11 | 554 | N | AAV11 | 579 | D |
| AAV12 | 414 | S | AAV12 | 563 | N | AAV12 | 588 | D |

That which is claimed is:

1. A Clade F adeno-associated virus (AAV) capsid protein, wherein the capsid protein comprises a substitution in one or more of amino acids N498, S499, E500, F501, A502, W503 and P504 (according to AAV9 VP1 numbering), in any combination, wherein the substitution in the capsid protein results in a Clade F viral phenotype of decreased transduction of liver cells as compared to a Clade F control or wild-type virus.

2. The Clade F AAV capsid protein of claim 1, comprising a W503R substitution, a N498Y substitution, a E500D substitution, or any combination thereof.

3. The Clade F AAV capsid protein of claim 1, comprising a W503R substitution, a N498I substitution, a E500D substitution, or any combination thereof.

4. A Clade F AAV capsid protein comprising a W503R substitution (according to AAV9 VP1 numbering), wherein the substitution in the capsid protein results in a Clade F viral phenotype of decreased transduction of liver cells as compared to a Clade F control or wild-type virus.

5. A Clade F AAV capsid protein comprising a N498Y substitution (according to AAVP1 numbering), wherein the substitution in the capsid protein results in a Clade F viral phenotype of decreased transduction of liver cells as compared to a Clade F control or wild-type virus.

6. A Clade F AAV capsid protein comprising a N4981 substitution (according to AAV9 VP1 numbering, wherein the substitution in the capsid protein results in a Clade F viral phenotype of decreased transduction of liver cells as compared to a Clade F control or wild-type virus.

7. A Clade F adeno-associated virus (AAV) capsid protein, wherein the capsid protein comprises a substitution in one or more of amino acids N498, S499, E500, F501, A502, W503 and P504 (according to AAV9 VP1 numbering), in any combination, wherein the substitution in the capsid protein results in a Clade F viral phenotype of reduced glycan binding affinity as compared to a Clade F control or wild-type virus.

8. The Clade F AAV capsid protein of claim 7, comprising a W503R substitution, a N498Y substitution, a E500D substitution, or any combination thereof.

9. The Clade F AAV capsid protein of claim 7, comprising a W503R substitution, a N498I substitution, a E500D substitution, or any combination thereof.

10. A Clade F AAV capsid protein comprising a W503R substitution (according to AAV9 VP1 numbering), wherein the substitution in the capsid protein results in a Clade F viral phenotype of reduced glycan binding affinity as compared to a Clade F control or wild-type virus.

11. A Clade F AAV capsid protein comprising a N498Y substitution (according to AAV9 VP1 numbering), wherein the substitution in the capsid protein results in a Clade F viral phenotype of reduced glycan binding affinity as compared to a Clade F control or wild-type virus.

12. The Clade F AAV capsid protein of claim 11, further comprising a L602F mutation.

13. A Clade F AAV capsid protein comprising a N498I substitution (according to AAV9 VP1 numbering), wherein the substitution in the capsid protein results in a Clade F viral phenotype of reduced glycan binding affinity as compared to a Clade F control or wild-type virus.

14. An AAV capsid comprising the AAV capsid protein of claim 1.

15. A virus vector comprising:

(a) the AAV capsid of claim 14; and (b) a nucleic acid comprising at least one terminal repeat sequence, wherein the nucleic acid is encapsidated by the AAV capsid.

16. A composition comprising the virus vector of claim 15 in a pharmaceutically acceptable carrier.

17. A method of introducing a nucleic acid into a cell, comprising contacting the cell with the virus vector of claim 15.

18. A method of delivering a nucleic acid to a subject in need thereof, comprising administering to the subject the virus vector of claim 15.

19. The method of claim 18, wherein the subject is a human subject.

20. The Clade F AAV capsid protein of claim 5, further comprising a L602F mutation.

* * * * *